US008022075B2

(12) United States Patent
Bando et al.

(10) Patent No.: US 8,022,075 B2
(45) Date of Patent: Sep. 20, 2011

(54) DIAGNOSTIC AND REMEDY FOR DISEASE CAUSED BY AMYLOID AGGREGATION AND/OR DEPOSITION

(75) Inventors: Kazunori Bando, Sanmu (JP); Kazumi Taguchi, Sanmu (JP)

(73) Assignees: Fujifilm Ri Pharma Co., Ltd., Tokyo (JP); Daiichi Sankyo Company, Limited, Tokyo (JP)

( * ) Notice: Subject to any disclaimer, the term of this patent is extended or adjusted under 35 U.S.C. 154(b) by 58 days.

(21) Appl. No.: 12/095,320

(22) PCT Filed: Nov. 30, 2006

(86) PCT No.: PCT/JP2006/323955
§ 371 (c)(1),
(2), (4) Date: May 29, 2008

(87) PCT Pub. No.: WO2007/063946
PCT Pub. Date: Jun. 7, 2007

(65) Prior Publication Data
US 2009/0162283 A1 Jun. 25, 2009

(30) Foreign Application Priority Data
Nov. 30, 2005 (JP) ................................ 2005-346676

(51) Int. Cl.
*A61K 31/4184* (2006.01)
*A61K 31/423* (2006.01)
*A61K 31/428* (2006.01)
*A61K 31/437* (2006.01)
*A61K 31/5025* (2006.01)
*C07D 471/04* (2006.01)
*C07D 487/04* (2006.01)
*C07D 235/18* (2006.01)
*C07D 263/57* (2006.01)
*C07D 277/66* (2006.01)

(52) U.S. Cl. .................. 514/259.1 ; 514/300; 514/394; 514/375; 514/367; 548/304.7; 548/152; 548/217; 548/224; 546/121; 544/282

(58) Field of Classification Search .................. None
See application file for complete search history.

(56) References Cited

U.S. PATENT DOCUMENTS

| 3,803,162 | A | | 4/1974 | Aebli et al. |
| 3,843,632 | A | * | 10/1974 | Matsuo et al. ................ 548/235 |
| 3,978,071 | A | | 8/1976 | Nakanishi et al. |
| 5,360,809 | A | | 11/1994 | Axelsson et al. |
| 7,270,800 | B2 | | 9/2007 | Klunk et al. |
| 7,351,401 | B2 | | 4/2008 | Klunk et al. |
| 2004/0037883 | A1 | | 2/2004 | Zhou et al. |
| 2005/0038067 | A1 | * | 2/2005 | Wang et al. ................ 514/301 |
| 2008/0075774 | A1 | | 3/2008 | Williams et al. |

FOREIGN PATENT DOCUMENTS

| DE | 24 32 410 A1 | 1/1975 |
| DE | 198 08 634 | 3/2008 |
| GB | 1 403 564 | 8/1975 |
| JP | 48-12401 A | 4/1973 |
| JP | 51-12841 A | 1/1976 |
| JP | 6-49037 A | 2/1994 |
| JP | 2002-511889 A | 4/2002 |
| JP | 2002523383 T | 7/2002 |
| JP | 2004 506723 | 3/2004 |
| JP | 2005-512945 | 5/2005 |
| JP | 2005 523903 | 8/2005 |
| JP | 2005-526802 | 9/2005 |
| JP | 2008-518016 A | 5/2008 |
| WO | WO 99/11627 A1 | 3/1999 |
| WO | WO 99/57114 A1 | 11/1999 |
| WO | WO 0010614 | 3/2000 |
| WO | WO0200655 A1 * | 6/2001 |
| WO | WO 02085903 | 10/2002 |
| WO | WO 03/080610 A1 | 10/2003 |

(Continued)

OTHER PUBLICATIONS

Byrn et al. Solid-State Chemistry of Drugs, 2d, Chapter 11 Hydrates and Solvates/hydrates, 233-247 (1999).*

(Continued)

*Primary Examiner* — Yong Chu
*Assistant Examiner* — Michael Barker
(74) *Attorney, Agent, or Firm* — Oblon, Spivak, McClelland, Maier & Neustadt, L.L.P.

(57) ABSTRACT

To provide a diagnostic drug which binds specifically to an amyloid aggregate and/or an amyloid deposit, to thereby realize imaging and quantification of a disease caused by amyloid aggregation and/or deposition.

The invention provides a compound represented by formula (1):

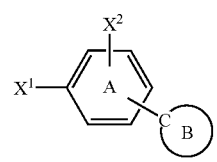

(1)

(wherein $X^1$ represents an optionally substituted bicyclic heterocyclic group;
$X^2$ represents a hydrogen atom, a halogen atom, or a chelate-forming group;
ring A represents a benzene ring or a pyridine ring; and
ring B represents an optionally substituted 5-membered aromatic heterocyclic group which is bonded to the benzene ring or the pyridine ring via a carbon atom of ring B), a salt thereof, a solvate of any of these, or a transition metal coordination compound of any of these, and a diagnostic, preventive, or therapeutic drug containing the same.

15 Claims, 6 Drawing Sheets

FOREIGN PATENT DOCUMENTS

| WO | 2004 032975 | 4/2004 |
|---|---|---|
| WO | 2004 058176 | 7/2004 |
| WO | 2004 064869 | 8/2004 |
| WO | 2004/083195 | 9/2004 |
| WO | 2004 094388 | 11/2004 |
| WO | WO 2004/110350 A2 | 12/2004 |
| WO | 2005 002503 | 1/2005 |
| WO | 2005/042461 | 5/2005 |
| WO | WO 2006/047516 A2 | 5/2006 |
| WO | 2006 113140 | 10/2006 |
| WO | WO 2007034278 A2 * | 3/2007 |
| WO | 2007/078895 | 7/2007 |
| WO | 2007/143959 | 12/2007 |
| WO | 2008/064163 | 5/2008 |

OTHER PUBLICATIONS

A.M. Rouhi, Chem. & Eng. News, Feb. 24, 2003, 81(8), 32-35.*

Morissette et al. Adv. Drug Delivery Rev. 2004, 56, 275-300.*

Hawkins. Philip N. et al., "Evaluation of Systemic Amyloidosis by Scintigraphy with $^{123}$I-Labeled Serum Amyloid P Component", The New England Journal of Medicine, Aug. 23, 1990, vol. 323, No. 8, pp. 508-513.

Kung, Mei-Ping et al., "Characterization of IMPY as a potential imaging agent for β-amyloid plaques in double transgenic PSAPP mice", European Journal of Nuclear Medicine and Molecular Imaging, vol. 31, No. 8, Aug. 2004, pp. 1136-1145.

Sugai, Yuichi et al., "Nihon Rinsho 61 Kan Zokango 9 Chihoshogaku (1)—Koreika Shakai to No Kagaku no Shinpo-", Dai 1 pan, pp. 571-574, (2003), (with partial English translation).

Habu, Haruo et al., "Nihon Rinsho 61 Kan Zokango 9 Chihoshogaku (1)—Koreika Shakai to No Kagaku no Shinpo-", Dai 1 pan, pp. 575-578, (2003), (with partial English translation).

Miyakawa, Koichi et al., "Nihon Rinsho 61 Kan Zokango 9 Chihoshogaku (1)—Koreika Shakai to No Kagaku no Shinpo-", Dai 1 pan, pp. 579-583, (2003), (with partial English translation).

Mitagawa, Noriyuki et al., "Nihon Rinsho 61 Kan Zokango 9 Chihoshogaku (1)—Koreika Shakai to No Kagaku no Shinpo-", Dai 1 pan, pp. 584-587, (2003), (with partial English translation).

Nanaba, Yoshio, "Nihon Rinsho 61 Kan Zokango 9 Chihoshogaku (1)—Koreika Shakai to No Kagaku no Shinpo-", Dai 1 pan, pp. 593-596, (2003), (with partial English translation).

Notice of Reasons for Rejection mailed Sep. 28, 2010 in Japanese Patent Application No. 2007-548001 (w/English Translation).

Richard M. Carr, et al., "Synthesis of Radiolabelled Versions of Angiotensin II Receptor Antagonists GR117289 and GR138950", Synthesis and Applications of Isotopically Labeled Compounds 1994, proceedings of the International Symposium, 5$^{th}$, Strasbourg, Jun. 20-24, 1994, 1995, pp. 635-639.

Rodney C. Young, et al., Development of a New Physiocochemical Model for Brain Penetration and Its Application to the Design of Centrally Acting $H_2$ Receptor Histamine Antagonists, J. Med. Chem. 1988, vol. 31, pp. 656-671.

Notice of Reasons for Rejection mailed Sep. 22, 2010 for Japanese Patent Application No. 2010-179093 (w/English Translation).

L. Racane, et al., Synthesis and Fluorescent Properties of Some New Unsymmetric bis-Benzothiazolyl Furans and Thiophenes, Monatshefte Für Chemie, 1995, vol. 126, pp. 1375-1381.

L. Racane, et al., Synthesis and Fluorescent Properties of Some New Unsymmetric bis-Benzothiazolyl Furans and Thiophenes, Monatshefte Für Chemie, 1995, vol. 127, p. 579.

Extended European Search Report mailed Jun. 20, 2011 in European Patent Application No. 06833758.3 filed Nov. 30, 2006.

* cited by examiner

B) Aqueous amyloid β (1-40) solution (corrected)

A) Amyloid β (1-40) aggregate suspension (corrected)

DIAGNOSTIC AND REMEDY FOR DISEASE CAUSED BY AMYLOID AGGREGATION AND/OR DEPOSITION

TECHNICAL FIELD

The present invention relates to a diagnostic drug or therapeutic drug for diseases caused by amyloid aggregation and/or deposition.

BACKGROUND ART

Amyloid is a specific protein having a fibrous structure. Amyloid exhibits weak acidophilic characteristics in hematoxylin-eosin staining, and assumes homogeneous and amorphous. Amyloid stains orange-red with alkaline Congo red staining, and shows green birefringence under a polarizing microscope. As observed under an electron microscope, amyloid is composed of non-branching fibrils having a width of 7 to 15 nm. Although amyloid seems to have a single morphology, amyloid is conceived to be composed of at least 20 types of proteins. Such proteins, in a monomeric state, do not exhibit toxicity, but cause organ dysfunction when aggregated. A common feature of aggregates of these proteins resides in that they are rich in β-sheet structure and are hard to dissolve.

Amyloidosis is a group of diseases in which dysfunction is caused by extracellular deposition or accumulation of amyloid fibrils in various organs in the whole body. As described below, amyloidosis is classified into systemic and localized forms according to the new classification by the Specified Disease Research Group of the Japanese Ministry of Health, labor and Welfare.

I. Systemic Amyloidosis
1. Immunocytic Amyloidosis

Deposition of immunoglobulin-derived (X- or K-light-chain-derived, or heavy-chain-derived) amyloid in organs of the whole body.

2. Reactive AA Amyloidosis (Secondary Amyloidosis)

Secondary to chronic inflammatory diseases (e.g., rheumatoid arthritis, tuberculosis, leprosy, and bronchiectasis), and deposition of amyloid derived from serum amyloid A (SAA), which is an acute-phase protein.

3. Familial Amyloidosis (Hereditary Amyloidosis)

Familial amyloid polyneuropathy (classified into types I to IV) causes specific sensory disorder or dyskinetic neuropathy, or autonomic neuropathy (variant transthyretin). Other examples of familial amyloidosis include familial Mediterranean fever and Muckle-Wells syndrome.

4. Dialysis Amyloidosis

Some long-term dialysis patients may exhibit β2-microglobulin-derived amyloidosis.

5. Senile Amyloidosis

Accumulation of wild-type transthyretin in the heart, and pulmonary or gastrointestinal vascular walls.

II. Localized Amyloidosis
1. Cerebral Amyloidosis

Alzheimer's disease, Down syndrome, cerebrovascular amyloidosis, hereditary cerebral amyloid angiopathy, British familial dementia, and Creutzfeldt-Jakob disease.

2. Endocrine Amyloidosis

Amyloidosis associated with medullary thyroid cancer, type-II diabetes/insulinoma, and localized atrial amyloidosis.

3. Cutaneous Amyloidosis
4. Localized Nodular Amyloidosis

Since amyloid can accumulate in any organ of the body, systemic amyloidosis causes a variety of symptoms. In an early stage, systemic amyloidosis causes non-specific initial symptoms, including general malaise, weight loss, edema, and anemia. Known symptoms during the course of systemic amyloidosis include congestive heart failure, nephrotic syndrome, malabsorption syndrome, peripheral neuropathy, orthostatic hypotension, carpal tunnel syndrome, and enlarged liver. In a clinical examination of systemic amyloidosis, amyloid-constituent proteins are detected through a hematological and serological assay. Meanwhile, $^{99m}$Tc-pyrophosphate scintigraphy is effective, but not specific for detection of cardiac amyloid, since $^{99m}$Tc-pyrophosphate may also accumulate in an ischemic site.

Established diagnosis of amyloidosis requires collection, through biopsy, of a tissue from an organ suspected of having amyloid deposition, followed by confirming amyloid deposition. After a pathological examination of the tissue collected by biopsy, an amyloid precursor protein is specified through combination of an immunohistological test, a serological test, and a genetic test, leading to established diagnosis. Diagnosis of amyloidosis requires determination of a site where a large amount of amyloid is accumulated, and biopsy for collecting tissue from the site. Therefore, such a diagnosis may require a highly invasive test at a certain biopsy site.

Now will be described reactive AA amyloidosis, which is a typical example of systemic amyloidosis. Reactive AA amyloidosis is a disease caused by deposition of amyloid derived from serum amyloid A (SAA) (i.e., an acute-phase reactive protein), and is secondary to a chronic inflammatory disease. For example, rheumatoid arthritis, whose prevalence is 0.3 to 0.8% of the population in Japan, is a primary disease of AA amyloidosis, and complication occurs in about 10% of AA amyloidosis cases. This amyloidosis is a disease (complication) with very poor prognosis, in which various organ dysfunctions are caused by extracellular deposition of amyloid, and the 50% survival time of patients with this disease is two to four years. In general, diagnosis of the disease is limited to only a method for confirming amyloid accumulation through biopsy. Although this method targets the kidney or the gastrointestinal tract where AA amyloid is accumulated, the method is invasive, and is particularly difficult to perform in the kidney. Recently, imaging of peripheral amyloid accumulation has been successfully performed by use of SAP (serum amyloid P component) labeled with $^{123}$I (Non-Patent Document 1). However, SAP, which is a glycoprotein having a molecular weight of 250 kDa, cannot pass through the blood-brain barrier (BBB), and thus imaging of cerebral amyloid accumulation fails to be performed. As has been reported, SAP is accumulated specifically in the liver, the spleen, the kidney, the adrenal glands, the bone marrow, or joints, but is not accumulated in the heart.

Alzheimer's disease is a type of localized amyloidosis, and has become a serious social issue with aging of the population. In Japan, the number of dementia patients has been rapidly increasing in accordance with aging of the population, and thus treatment and care of dementia patients are imminent issues which must be rapidly solved from the viewpoint of health economics. The number of dementia patients is estimated to reach three million in 2050, and patients with Alzheimer's disease are expected to account for the majority of the dementia patients. In the United States, the number of Alzheimer's disease patients is currently four million, whereas in Japan, the number is estimated to be one million. Alzheimer's disease is a poor-prognosis disease which is associated with continuous progression and results in certain death; i.e., a half of Alzheimer's disease patients die within three to eight years after the onset of the disease.

Diagnostic imaging is an important examination for differentiating Alzheimer's disease from another amyloid disease. However, no evidence is obtained through contrast between autopsy and imaging. Attempts have been made to diagnose Alzheimer's disease in its early stage by means of CT or MRI for detecting cerebral atrophy, or PET or SPECT for measuring change in glucose metabolism or cerebral blood flow, so as to provide typical findings of Alzheimer's disease. However, such findings are not necessarily obtained from some Alzheimer's disease patients.

Established diagnosis of Alzheimer's disease requires pathological diagnosis, which is generally based on distribution of senile plaques, or Alzheimer neurofibrillary tangle; for example, according to CERAD (Consortium to Establish a Registry for Alzheimer's Disease), or the staging by Braak, et al. Of these, in CERAD pathological diagnostic criteria, the number of typical senile plaques stained with silver impregnation is semi-quantified, followed by classification into "sparse" ($2/mm^2$), "moderate" ($6/mm^2$), and "frequent" ($35/mm^2$) at the neocortex with the most severe Alzheimer's lesion; and the level of Alzheimer's disease is evaluated as being "definite," "probable," or "normal" through comparison with the number of senile plaques normalized according to stratification of age.

As described above, established diagnosis of Alzheimer's disease requires data on distribution of senile plaques in the brain, or neurofibrillary tangle. Particularly, senile plaques are considered to have been accumulated for several decades before the onset of Alzheimer's disease, and detection of this amyloid accumulation meets the purpose of early diagnosis of Alzheimer's disease. In recent years, attempts have been made to capture such senile plaques in the form of an image. A nuclear medicine technique employing nuclear magnetic resonance or a radioisotope is considered a technique for in vivo imaging of cerebral senile plaques. Particularly, attempts have been made to directly image senile plaques through a nuclear magnetic resonance technique in APP-overexpressed transgenic mice (Tg mice). However, such a technique requires a high magnetic field of 7 T or higher, and provides low contrast with respect to senile plaques.

Furthermore, attempts have been made to develop a drug which binds specifically to amyloid for imaging thereof, for the purpose of enhancing sensitivity by increasing contrast between the normal tissue and amyloid. Recently, Higashi, et al. have developed a drug which passes through the blood-brain barrier (BBB) and binds to amyloid (Patent Document 1). However, clinical application thereof requires a ligand exhibiting higher activity.

Many attempts have been made to visualize amyloid aggregates by binding a radionuclide to a ligand which binds to the amyloid aggregates, and reconstituting an image by means of a γ-ray-detecting apparatus. Imaging of senile plaques in the brain of an Alzheimer's disease (AD) patient was first successfully performed in the world by use of [$^{18}$F]-FDDNP, which is a radioactive drug developed by a group of UCLA. This drug realizes imaging of both senile plaques and neurofibrils (Patent Document 2). In addition, a significant difference was observed in retention time of the drug in the brain between AD patients and control subjects, and the retention time was found to be correlated with cognitive function. However, as shown in an image obtained in a late stage after administration of the drug, only a small difference (about 10 to about 30%) is found in radioactivity retention in the brain of an AD patient between the cerebral cortex where many senile plaques are present and the pons where few senile plaques are present; i.e., a large background is provided.

A new amyloid imaging agent having a thioflavin structure has been developed in the University of Pittsburgh, and is named Pittsburgh Compound-B ($^{11}$C-PIB) (Patent Documents 3 and 4). As has been reported, when $^{11}$C-PIB is administered to a mild AD patient, considerable retention of the agent is observed in an amyloid-accumulated cortex region, as compared with the control, and thus the agent realizes clear distinction between an Alzheimer's disease patient and a normal subject. However, a difference in retention of $^{11}$C-PIB between AD patient groups is at most about two-fold. Therefore, demand has arisen for a diagnostic drug which can achieve a higher contrast for examining the degree of amyloid accumulation in more detail. Such a drug is essential for determining whether or not a patient with a symptom which is more difficult to diagnose (e.g., mild cognitive impairment (MCI)) will develop Alzheimer's disease. As has also been reported, when $^{11}$C-PIB is administered to mice in which APP is overexpressed so as to generate amyloid aggregates (PS1/APP mice), and then the mice are tested by means of an animal PET scanner, no difference is observed in retention time of $^{11}$C-PIB between PS1/APP mice and normal mice; i.e., $^{11}$C-PIB exhibits considerably low affinity to amyloid aggregates of PS1/APP mice, and thus imaging of amyloid accumulation fails to be attained in vivo animal experiments by use of $^{11}$C-PIB. Furthermore, $^{11}$C, which is a labeling nuclide of $^{11}$C-PIB, has a half-life of 20 minutes. In general, such a positron-emitting nuclide employed for imaging has a very short half-life. In view that a compound is labeled with a radionuclide produced by means of a cyclotron, the compound must be capable of being labeled within a short period of time, and the cyclotron must be placed in the vicinity a PET apparatus. In addition, the thus-labeled compound must be under strict quality control, since the compound is administered in vivo. Therefore, in Japan, there are only a few facilities which can perform labeling with a positron-emitting nuclide, as well as imaging of amyloid in vivo.

Commercially suppliable and industrially useful means is a drug product labeled with a nuclide which has a longer half-life (about 6 to about 72 hours) and emits γ-rays. Examples of the nuclide which meets this requirement include $^{123}$I and $^{99m}$Tc. The University of Pennsylvania has reported that $^{123}$I-IMPY, which has been studied for the purpose of $^{123}$I labeling, exhibits high affinity to amyloid accumulated in the brain of AD patients or Tg mice (Patent Document 5). The amyloid-binding probe having a thioflavin skeleton labeled with a radioisotope has an N-alkylamine structure. In general, an N-alkylamine structure undergoes in vivo metabolism. Therefore, an N-dealkylated radioactive ligand metabolite having no amyloid-binding property and exhibiting lipid solubility passes through the blood-brain barrier, and enters the brain, whereby the metabolite is accumulated therein regardless of amyloid (Non-Patent Document 2). Therefore, keen demand has arisen for development of a derivative, a metabolite of which is not detected in the brain.

Conceivably, a substance which inhibits aggregation and/or deposition of amyloid (including amyloid protein and amyloid-like protein) is effective for prevention or treatment of amyloidosis. Prevention or treatment of cerebral amyloidosis (e.g., Alzheimer's disease) requires a diagnostic drug or therapeutic drug which can pass through the blood-brain barrier.

Patent Document 1: WO 2005/042461 pamphlet
Patent Document 2: Japanese Kohyo Patent Publication No.
Patent Document 3: WO 2004/083195 pamphlet
Patent Document 4: Japanese Kohyo Patent Publication No.
Patent Document 5: Japanese Kohyo Patent Publication No.

Non-Patent Document 1: Hawkins P. N., Lavender J. P., Pepys M. B., N. Engl. J. Med. 1990 Aug. 23; 323(8): 508-13.
Non-Patent Document 2: Kung M. P., Hou C., Zhuang Z. P., Cross A. J., Maier D. L., Kung H. F., Eur. J. Nucl. Med. Mol. Imaging. 2004 August; 31(8): 1136-45. Epub 2004 March 9.

DISCLOSURE OF THE INVENTION

Problems to be Solved by the Invention

An object of the present invention is to provide a diagnostic drug which binds specifically to an amyloid aggregate and/or an amyloid deposit, to thereby realize imaging and quantification of a disease caused by amyloid aggregation and/or deposition.

Another object of the present invention is to provide a preventive and/or therapeutic drug for a disease caused by amyloid aggregation and/or deposition, which drug inhibits amyloid aggregation and/or deposition.

Yet another object of the present invention is to provide a screening method for determining a preventive and/or therapeutic drug for a disease caused by amyloid aggregation and/or deposition.

Means for Solving the Problems

In order to achieve the aforementioned objects, the present inventors have searched for a substance which binds specifically to amyloid, which passes through the blood-brain barrier, and a metabolite of which is not detected in the brain, and have found that a compound represented by the following general formula (1) exhibits such characteristics, and is useful as a diagnostic drug for a disease caused by amyloid aggregation and/or deposition, or as a preventive and/or therapeutic drug for the disease. The present invention has been accomplished on the basis of this finding.

Accordingly, the present invention provides a compound represented by formula (1):

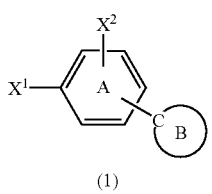

(1)

[F1]

(wherein $X^1$ represents an optionally substituted bicyclic heterocyclic group;

$X^2$ represents a hydrogen atom, a halogen atom, or a chelate-forming group;

ring A represents a benzene ring or a pyridine ring; and ring B represents an optionally substituted 5-membered aromatic heterocyclic group which is bonded to the benzene ring or the pyridine ring via a carbon atom of ring B), a salt thereof, a solvate of any of these, or a transition metal coordination compound of any of these.

The present invention also provides a diagnostic, preventive, and/or therapeutic drug containing a compound represented by formula (1), a salt thereof, a solvate of any of these, or a transition metal coordination compound of any of these.

The present invention also provides use of a compound represented by formula (1), a salt thereof, a solvate of any of these, or a transition metal coordination compound of any of these for producing a drug.

The present invention also provides a pharmaceutical composition comprising a compound represented by formula (1), a salt thereof, a solvate of any of these, or a transition metal coordination compound of any of these, and a pharmaceutically acceptable carrier.

The present invention also provides a method for prevention and/or treatment of a disease caused by amyloid aggregation and/or deposition, characterized in that the method comprises administering, to a subject in need thereof, a compound represented by formula (1), a salt thereof, a solvate of any of these, or a transition metal coordination compound of any of these in an effective amount.

The present invention also provides a method for imaging an amyloid deposit, characterized in that the method comprises administering, to a subject in need thereof, a labeled compound of a compound represented by formula (1), a salt thereof, a solvate of any of these, or a transition metal coordination compound of any of these in a detectable amount, allowing to pass a sufficient period of time for binding the labeled compound to the amyloid deposit, and detecting the labeled compound which has been bound to the amyloid deposit.

The present invention also provides a compound represented by formula (2):

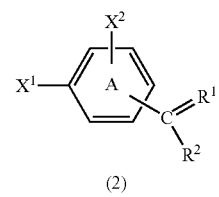

(2)

[F2]

(wherein $R^1$ represents an oxygen atom, a sulfur atom, or $NR^3$ (wherein $R^1$ represents a hydrogen atom, a hydroxy group, or an alkoxy group); $R^2$ represents an optionally substituted alkyl group, an optionally substituted alkenyl group, or an optionally substituted amino group; and $X^1$, $X^2$, and ring A have the same meanings as defined above, which serves as a production intermediate of a compound represented by formula (1), a salt thereof, or a solvate of any of these.

The present invention also provides a screening method for a preventive and/or therapeutic drug for a disease caused by amyloid aggregation or deposition, characterized in that method comprises detecting the binding ability of a specimen to amyloid or determining the degree of amyloid aggregation and/or deposition by use of a compound represented by formula (1), a salt thereof, a solvate of any of these, or a transition metal coordination compound of any of these. The invention also provides a preventive and/or therapeutic drug for a disease caused by amyloid aggregation or deposition, the drug containing a substance selected through the screening method.

Effects of the Invention

The compound (1) of the present invention exhibits high affinity to amyloid aggregates or amyloid deposits and passes through the blood-brain barrier. The compound also exhibits high stability in biological bodies and has high safety due to the absence of a metabolite in the brain. Thus, the compound (1) of the present invention is a useful diagnostic drug for a disease caused by amyloid aggregation or deposition, particularly an image diagnostic drug.

Since the compound (1) of the present invention inhibits aggregation and/or deposition of amyloid, the compound is a useful drug for preventing and/or treating a disease caused by amyloid aggregation and/or deposition; i.e., amyloidosis. The compound (1) of the invention is useful for screening to select a drug for preventing and/or treating a disease caused by amyloid aggregation and/or deposition.

BEST MODES FOR CARRYING OUT THE INVENTION

Figure 1:
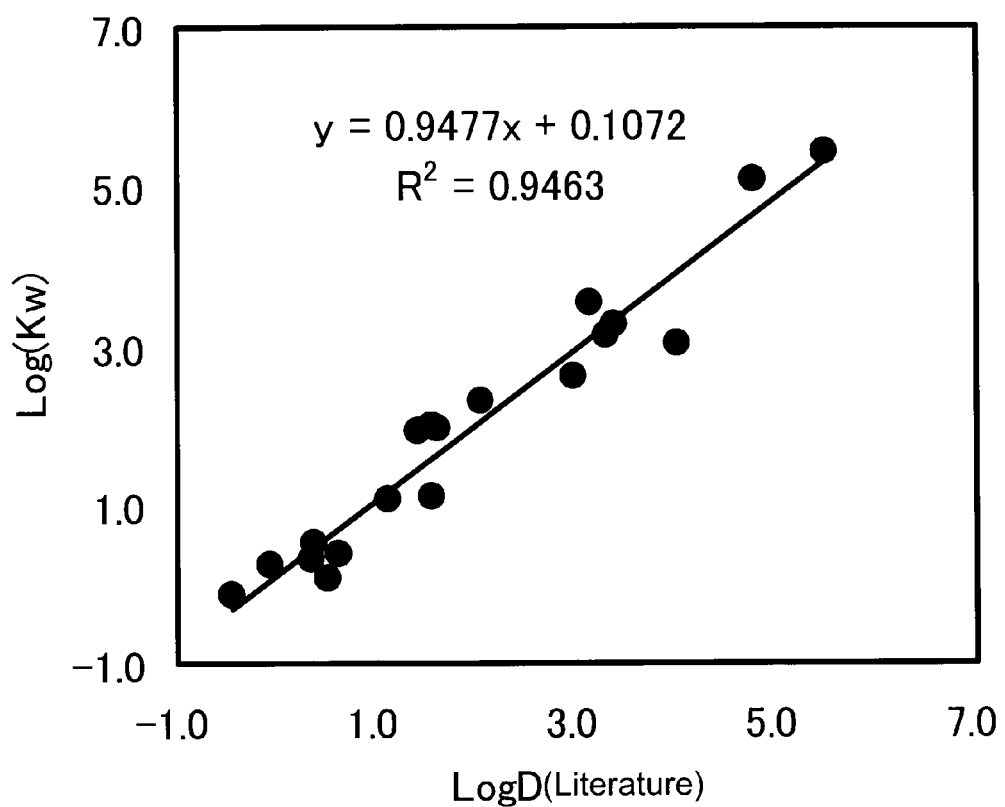
FIG. 1 A graph showing the correlation of log kw of liposolubility standard substance to log D7.4 of the same.

In formula (1), $X^1$ represents an optionally substituted bicyclic heterocyclic group. Examples of the bicyclic heterocyclic group include 5-membered-5-membered bicyclic heterocyclic groups, 6-membered-5-membered heterocyclic groups, and 6-membered-6-membered heterocyclic groups. Of these, 6-membered-5-membered heterocyclic groups are preferred. The bicyclic heterocyclic group is preferably a 6-membered-5-membered heterocyclic group having 2 to 4 heteroatoms selected from among a nitrogen atom, an oxygen atom, and a sulfur atom. Examples of the heterocyclic group include benzothiazolyl, benzisothiazolyl, benzoxazolyl, benzisoxazolyl, benzimidazolyl, benzopyrazolyl, imidazopyridyl, imidazopyrimidyl, thiazolopyridyl, thiazolopyrimidyl, oxazolopyridyl, oxazolopyrimidyl, triazolopyridyl, triazolopyrimidyl, imidazopyridazyl, thienopyridyl, pyrrolopyridyl, and furopyridyl. Of these, benzothiazolyl, benzoxazolyl, imidazopyridyl, imidazopyrimidyl, benzimidazolyl, etc. are particularly preferred.

The group $X^1$ which may serve as a substituent of the bicyclic heterocyclic group may be one to three members selected from among a halogen atom, a hydroxy group, an alkyl group, an alkyltin group, a halogenoalkyl group, a halogenoalkylcarbonylamino group, and a chelate-forming group.

Examples of the halogen atom include fluorine, chlorine, bromine, and iodine. Examples of the alkyl group include C1-C8 alkyl groups. Of these, C1-C6 alkyl groups are preferred. The alkyl group may be linear or branched. Specific examples include methyl, ethyl, propyl, isopropyl, butyl, isobutyl, tert-butyl, and pentyl. Examples of the alkyltin group include tri($C_1$-$C_8$ alkyl)tin groups, with tri($C_1$-$C_6$ alkyl)tin groups being preferred. Specific examples include trimethyltin, triethyltin, and tibutyltin. The halogenoalkyl group is preferably a halogeno-$C_1$-$C_8$ alkyl group, with a halogeno-$C_1$-$C_6$ alkyl group being particularly preferred. Specific examples include chloromethyl, bromomethyl, fluoromethyl, iodomethyl, chloroethyl, bromoethyl, fluoroethyl, iodoethyl, chloropropyl, fluoropropyl, and iodopropyl. Examples of the halogenoalkylcarbonylamino group include halogeno($C_1$-$C_8$ alkyl)carbonylamino groups. Of these, halogeno($C_1$-$C_6$ alkyl)carbonylamino groups are preferred. Specific examples include chloroacetamino, fluoroacetamino, iodoacetamino, chloropropanoylamino, fluoropropanoylamino, iodopropanoylamino, chlorobutanoylamino, fluorobutanoylamino, and iodobutanoylamino.

Examples of the chelate-forming group include the following (note that the following structures also include chelate-forming transition metal atoms):

[F3]

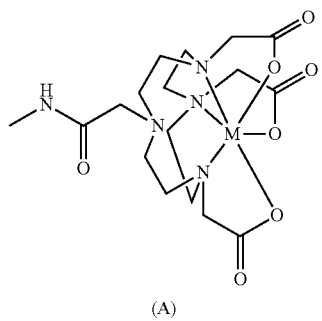

(A)

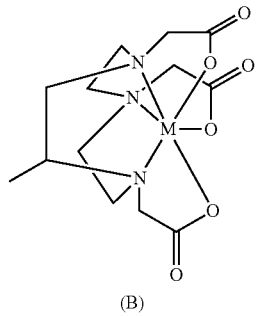

(B)

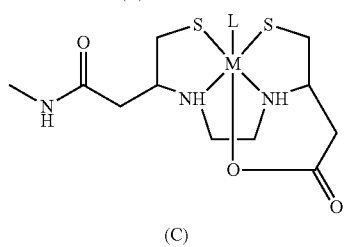

(C)

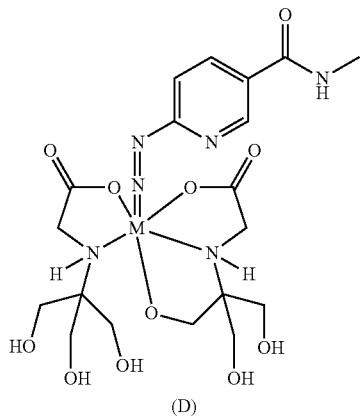

(D)

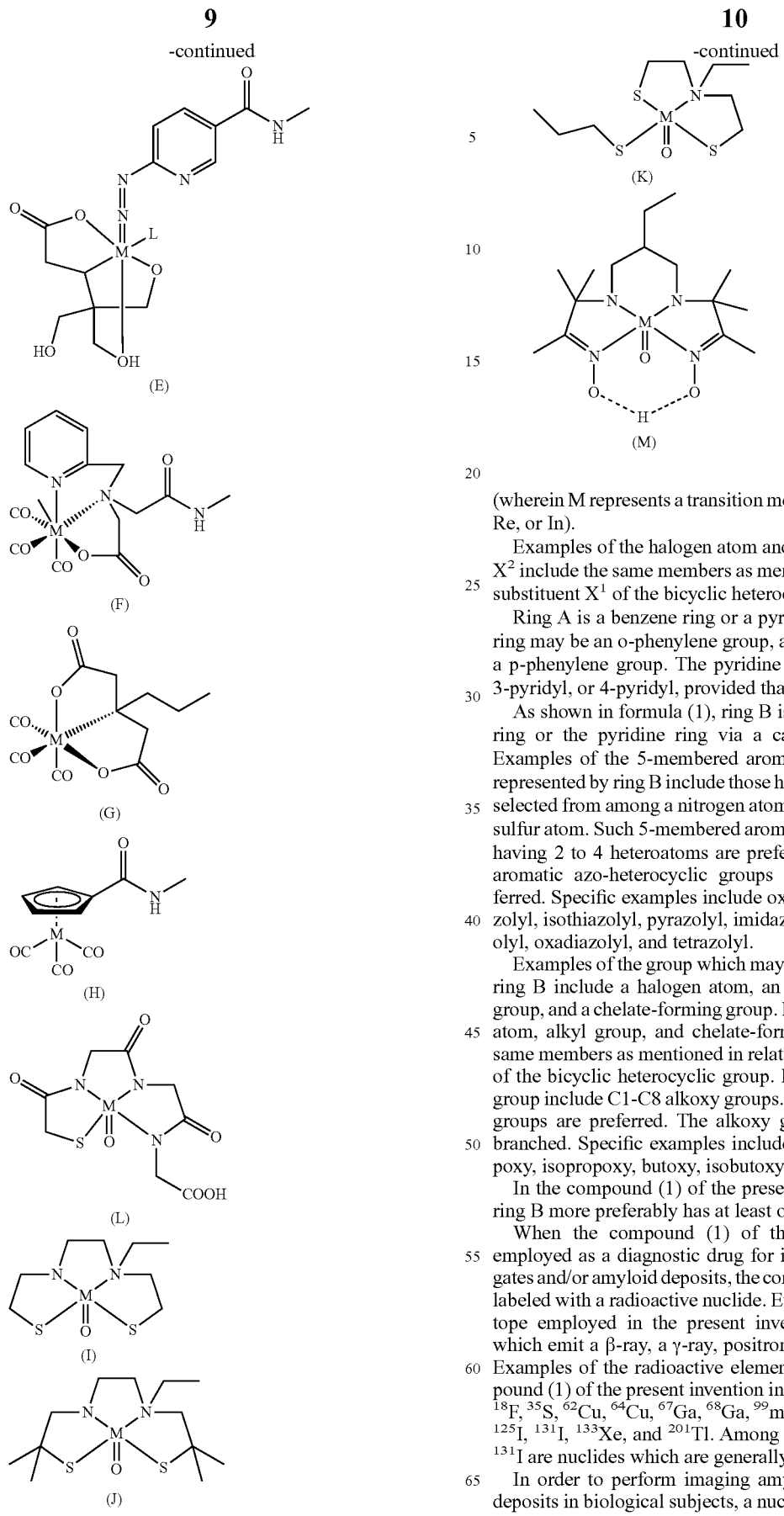

(wherein M represents a transition metal atom such as Ga, Tc, Re, or In).

Examples of the halogen atom and chelate-forming group $X^2$ include the same members as mentioned in relation to the substituent $X^1$ of the bicyclic heterocyclic group.

Ring A is a benzene ring or a pyridine ring. The benzene ring may be an o-phenylene group, a m-phenylene group, or a p-phenylene group. The pyridine ring may be 2-pyridyl, 3-pyridyl, or 4-pyridyl, provided that the locant of $X^1$ is 1.

As shown in formula (1), ring B is bonded to the benzene ring or the pyridine ring via a carbon atom of ring B. Examples of the 5-membered aromatic heterocyclic group represented by ring B include those having 1 to 4 heteroatoms selected from among a nitrogen atom, an oxygen atom, and a sulfur atom. Such 5-membered aromatic heterocyclic groups having 2 to 4 heteroatoms are preferred, with 5-membered aromatic azo-heterocyclic groups being particularly preferred. Specific examples include oxazolyl, isoxazolyl, thiazolyl, isothiazolyl, pyrazolyl, imidazolyl, triazolyl, thiadiazolyl, oxadiazolyl, and tetrazolyl.

Examples of the group which may serve as a substituent of ring B include a halogen atom, an alkyl group, an alkoxy group, and a chelate-forming group. Examples of the halogen atom, alkyl group, and chelate-forming group include the same members as mentioned in relation to the substituent $X^1$ of the bicyclic heterocyclic group. Examples of the alkoxy group include C1-C8 alkoxy groups. Of these, C1-C6 alkoxy groups are preferred. The alkoxy group may be linear or branched. Specific examples include methoxy, ethoxy, propoxy, isopropoxy, butoxy, isobutoxy, and tert-butoxy.

In the compound (1) of the present invention, $X^1$, $X^2$, or ring B more preferably has at least one halogen atom.

When the compound (1) of the present invention is employed as a diagnostic drug for imaging amyloid aggregates and/or amyloid deposits, the compound (1) is preferably labeled with a radioactive nuclide. Examples of the radioisotope employed in the present invention include nuclides which emit a β-ray, a γ-ray, positron emission, or an X-ray. Examples of the radioactive element for labeling the compound (1) of the present invention include $^3H$, $^{14}C$, $^{11}C$, $^{13}N$, $^{18}F$, $^{35}S$, $^{62}Cu$, $^{64}Cu$, $^{67}Ga$, $^{68}Ga$, $^{99m}Tc$, $^{111}In$, $^{122}I$, $^{123}I$, $^{124}I$, $^{125}I$, $^{131}I$, $^{133}Xe$, and $^{201}Tl$. Among them, $^3H$, $^{14}C$, $^{35}S$, and $^{131}I$ are nuclides which are generally employed in vitro.

In order to perform imaging amyloid aggregates and/or deposits in biological subjects, a nuclide which emits a γ-ray of high bio-transmittance or a positron-emitting nuclide is employed. Through labeling the compound (1) of the present invention with such a nuclide and administering it to a biological body, amyloid can be imaged. This method gives considerably less damage to patients and, therefore, is a non-invasive method. The "positron (positive electron)" is an electron having a positive charge. Since a positively charged positron and a negatively charged electron (i.e., normal electron) attract each other, a positron is readily coupled with an electron. During coupling, two γ-rays are emitted to the directions opposite to each other. The thus-emitted γ-rays are simultaneously detected by a couple of detectors, whereby a PET (Positron Emission Tomography) can be obtained with high resolution and quantitative degree. Examples of the nuclide employed for this purpose include $^{11}$C, $^{13}$N, $^{15}$O, and $^{18}$F. Among them, $^{11}$C and $^{18}$F are preferred. However, since positron-emitting nuclides employed in the imaging generally have a short half life and are generated by means of a cyclotron, the target compound must be labeled with such nuclides for a short period of time. In addition, a cyclotron must be installed near a PET apparatus, and a labeled compound must be quality-controlled. Therefore, in Japan, there are limited numbers of facilities where amyloid in biological bodies can be imaged by use of a compound labeled with a positron-emitting nuclide. One recent simple technique for solving this problem is generation of PET nuclide by means of a $^{68}$Ge/$^{68}$Ga generator. Since $^{68}$Ga is a metallic radionuclide, a chelate moiety containing the radio nuclide must be introduced into a target compound. Typical examples of the $^{68}$Ga-chelate structure include those represented by the aforementioned formulas (A) and (B) (wherein M is Ga).

Generally, in order to obtain commercially useful images, an imaging drug is labeled with a nuclide which emits a γ-ray. A detector detects the γ-ray emitted from the drug compound, whereby a two-dimensional image is obtained. This imaging can be attained through employment of a collimator for detecting a γ-ray only in a specific direction and performing γ-ray detection and positional analysis. Recently, in a general procedure, such an apparatus (e.g., a gamma camera) is rotated to collect data, and a tomographic image is re-constructed from the data. This technique is called SPECT (Single photon emission computed tomography). Generally, since SPECT can detect a γ-ray having relatively low energy as compared with PET, SPECT is greatly affected by absorption and scattering, and therefore is considered to have poor quantitativity as compared with PET. However, through a variety of analysis techniques, quantitation through SPECT has been realized. Examples of the γ-ray-emitting nuclide employed in SPECT include $^{67}$Ga, $^{99m}$Tc, $^{111}$In, $^{123}$I, $^{124}$I, $^{125}$I, $^{133}$Xe, and $^{201}$Tl. Of these, $^{123}$I (half life: 13 hours) and $^{99m}$Tc, which is a generator nuclide and has a half life of 6 hours, are preferred. $^{99m}$Tc is a radionuclide which is readily available by means of a $^{99}$Mo-$^{99m}$Tc generator and is highly suitable for daily examinations. Since $^{99m}$Tc is a metallic radionuclide, a chelate moiety containing the radio nuclide must be introduced into a target compound. Typical examples of the $^{99m}$Tc-chelate structure include those represented by the aforementioned formulas (C) to (J) (wherein M is Tc).

Feasibility studies have been carried out for in vivo imaging according to the present invention through magnetic resonance imaging (MRI) or magnetic resonance spectroscopy (MRS). Examples of the nuclide for use in the imaging include $^{1}$H, $^{31}$P, $^{2}$D, $^{7}$Li, $^{19}$F, and $^{13}$C.

Another example of the imaging is electron paramagnetic resonance (EPR). One labeling agent for use with EPR is nitroxide, which is an EPR probe known in the art.

Examples of the salt of the compound of the present invention include inorganic acid salts and organic acid salts. Examples of the acid of inorganic acid salts include hydrochloric acid, hydrobromic acid, sulfuric acid, sulfamic acid, phosphoric acid, and nitric acid. Examples of the acid of organic acid salts include maleic acid, fumaric acid, benzoic acid, ascorbic acid, succinic acid, oxalic acid, bismethylenesalicylic acid, methanesulfonic acid, ethanedisulfonic acid, acetic acid, propionic acid, tartaric acid, salicylic acid, citric acid, gluconic acid, lactic acid, malic acid, mandelic acid, cinnamic acid, citraconic acid, aspartic acid, stearic acid, palmitic acid, itaconic acid, glycolic acid, p-aminobenzoic acid, glutamic acid, benzenesulfonic acid, theophylline acetic acid, and 8-halotheophylline such as 8-bromotheophylline. Examples of the solvate of the compound of the present invention include hydrates and solvates with organic solvents.

The method for producing the compound (1) of the present invention, which depends on the structure of the heterocyclic group $X^1$ and of ring B, is categorized into two types; i.e. a method in which the heterocycle $X^1$ is formed in a last step and a method in which ring B is formed in a last step. Note that rings A and B are not limited to those shown in the following reaction schemes.

In the case (A) in which ring B is formed in a last step, the compound (1) of the present invention may be produced according to the following reaction scheme:

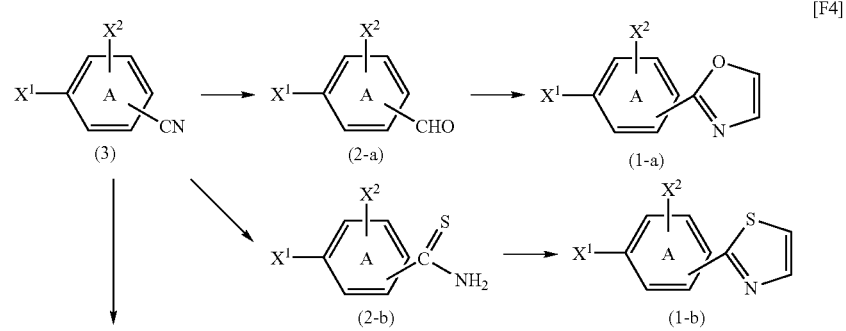

[F4]

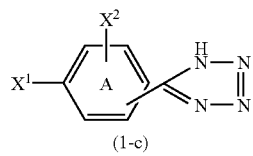

(wherein $X^1$, $X^2$, and ring A have the same meanings as defined above).

Specifically, a nitrile form (3) is reduced to thereby produce an aldehyde form (2-a), which is reacted with a methyl isocyanide to thereby produce an oxazole form (1-a). Reduction of the nitrile form is performed by use of a reducing agent such as dialkylaluminum hydride (e.g., diisobutylaluminum hydride), catecholamine, Raney nickel, or stannous chloride in a halohydrocarbon such as dichloromethane or an ether solvent such as tetrahydrofuran at −10° C. to 50° C.

Examples of the methyl isocyanide employed in conversion of the aldehyde form (2-a) to the oxazole form (1-a) include p-toluenesulfonylmethyl isocyanide, and benzotriazolylmethyl isocyanide. The reaction is performed in an alcoholic solvent such as methanol in the presence of a base such as potassium carbonate, sodium hydrogencarbonate, or sodium hydroxide with heating for 5 to 24 hours.

The nitrile form (3) is reacted with thioacetamide to thereby produce a thioamide form (2-b), which is reacted with a halogenoacetaldehyde, to thereby produce a thiazole form (1-b). The reaction between the nitrile form (3) and thioacetamide is performed in the presence of an acid such as hydrochloric acid or sulfuric acid with heating in a polar solvent such as dimethylformamide, dimethylacetamide, or N-methylpyrrolidone.

Examples of the halogenoacetaldehyde employed in conversion of the thioamide form (2-b) to the thiazole form (1-b) include chloroacetaldehyde, bromoacetaldehyde, and bromoacetaldehyde diethylacetal. The reaction is performed in the presence of a base such as triethylamine or pyridine with heating.

The nitrile form (3) is reacted with an azide compound for ring-closing, to thereby produce a tetrazole form (1-c). Examples of the azide compound employed include azidotrimethylsilane and sodium azide. The ring-closing reaction is preferably performed with heating in the presence of a metallic catalyst such as trimethylaluminum.

Another reaction scheme is as follows:

[F5]

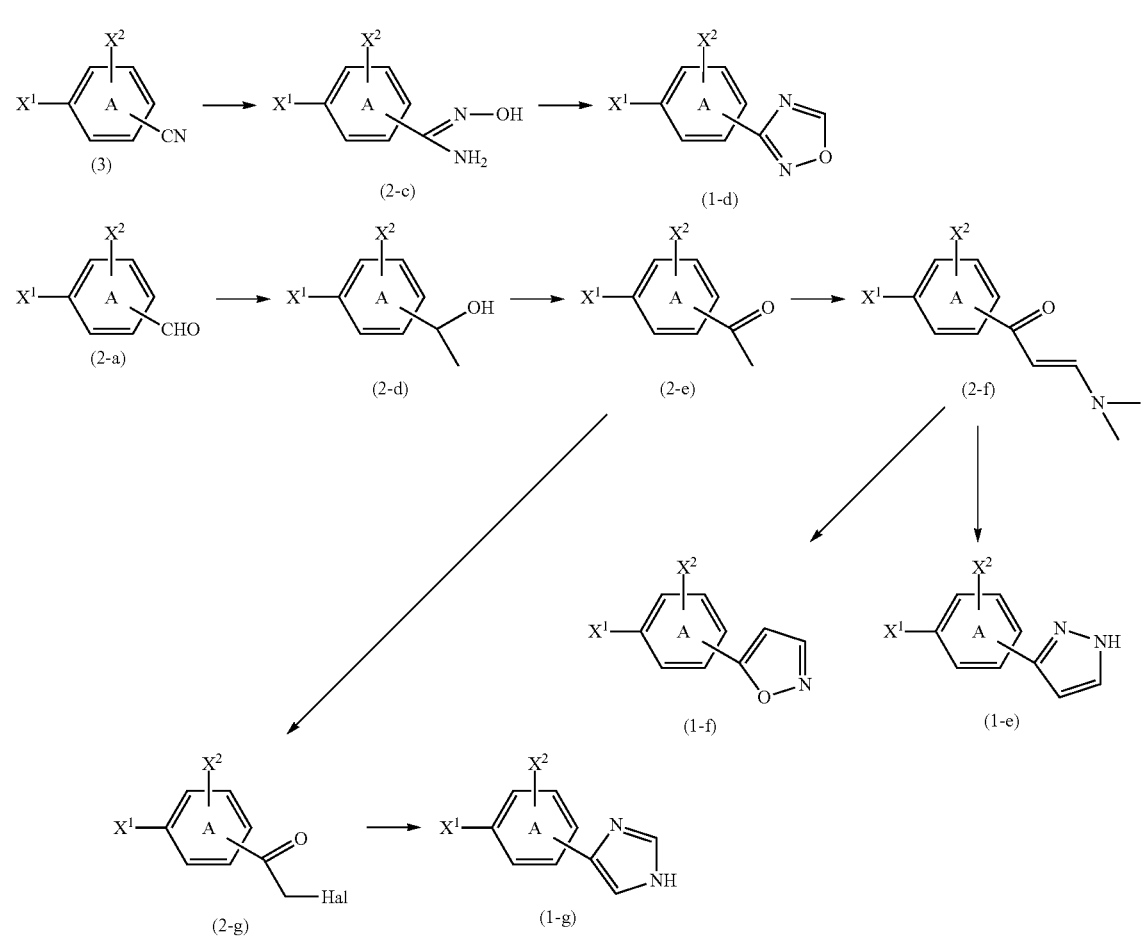

(wherein Hal represents a halogen atom, and X¹, X², and ring A have the same meanings as defined above).

The nitrile form (3) is reacted with hydroxylamine in the presence of a base to thereby produce an amidine form (2-c), which is reacted with a methylating agent such as trimethyl orthoformate, to thereby produce an oxadiazole form (1-d). The reaction between the nitrile form (3) and hydroxylamine is performed in the presence of a base such as potassium carbonate, sodium carbonate, sodium hydrogencarbonate, or sodium hydroxide under heating. Ring-closing reaction of the amidine form (2-c) is performed through reacting with, for example, trimethyl orthoformate under reflux conditions.

The aldehyde form (2-a) is reacted with a Grignard reagent such as methylmagnesium bromide and then with water, to thereby produce a compound (2-d), which is oxidized to thereby produce an acetophenone form (2-e). The acetophenone form (2-e) is reacted with dimethylformamide acetal, to thereby produce a compound (2-f), followed by reacting with hydrazine, to thereby produce a pyrazole form (1-e). When the compound (2-f) is reacted with hydroxylamine, an isoxazole form (1-f) is produced.

The alcohol form (2-d) is oxidized by use of manganese dioxide, chromium trioxide, m-chloroperbenzoic acid, dimethyl sulfoxide, etc. The reaction between the acetophenone form (2-e) and dimethylacetamide acetal is performed through heating at 130 to 160° C. Ring-closing of the compound (2-f) by use of hydrazine is performed through heating in an alcoholic solvent such as ethanol. Ring-closing of the compound (2-f) by use of hydroxylamine is performed through heating in an alcoholic solvent such as ethanol.

The compound (2-e) is reacted with a halogenating agent to thereby produce a compound (2-g), which is reacted with formamide, to thereby produce an imidazole form (1-g). Examples of the halogenating agent employed include N-halogenosuccinimide, tetrabutylammonium tribromide, and bromine. The reaction between the compound (2-g) and formamide is performed under heating.

In the case (B) in which the heterocycle X¹ is formed in a last step, the compound (1) of the present invention may be produced according to the following reaction scheme:

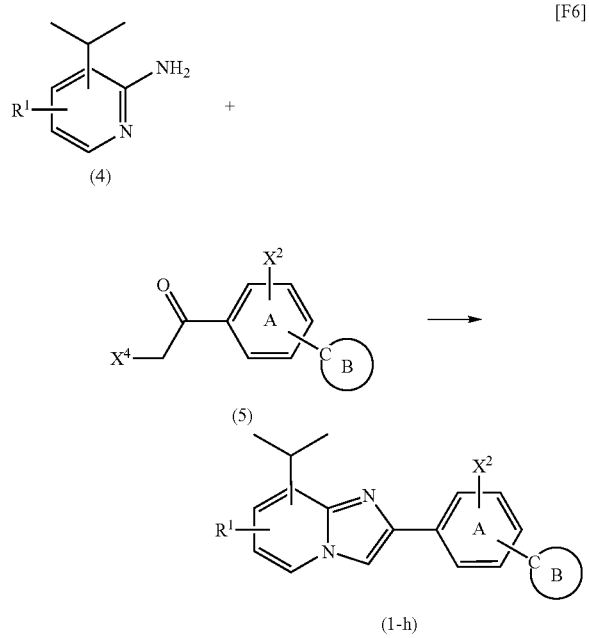

[F6]

(wherein R¹ represents a hydrogen atom or the same substituent as bonded to the heterocyclic group X¹; Y represents a carbon atom or a nitrogen atom; X⁴ represents a halogen atom; and X², ring A, and ring B have the same meanings as defined above).

An aromatic amine (4) is reacted with a compound (5), to thereby produce a compound (1-h). This reaction is generally performed in a solvent in the presence of a base at room temperature or elevated temperature. Depending on the type of the compound (5), high production yield can be attained through this reaction under reflux with heating conditions. Examples of the base which can be employed in the reaction include inorganic bases such as potassium carbonate and sodium hydrogencarbonate and organic bases such as triethylamine. The solvent may be an organic solvent which is not reactive to a substrate, a product, a reagent, etc. Examples of the organic solvent include ethanol, methanol, ethers, tetrahydrofuran, acetone, benzene, and toluene. Of these, ethanol, methanol, and acetone are preferred.

Another reaction scheme is as follows:

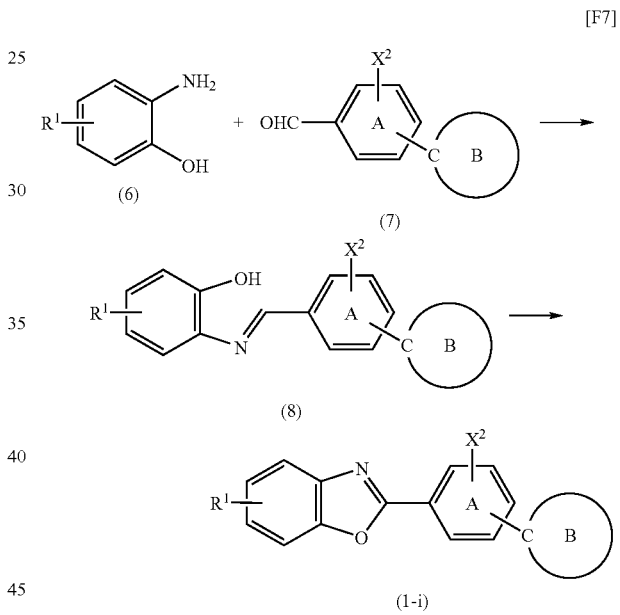

[F7]

(wherein R¹, X², ring A, and ring B have the same meanings as defined above).

Through condensation between a compound (6) and an aldehyde form (7), a compound (8) is produced. Subsequently, through reaction with a condensing agent such as iodobenzene diacetate or triacetoxymanganese, a compound (1-i) is produced. The reaction between the compound (6) and the aldehyde form (7) may be performed in an alcoholic solvent such as ethanol under heating. Ring-closing reaction of the compound (8) may be performed by use of, for example, iodobenzene diacetate at 0 to 60° C.

As is clear from the above reaction scheme, the compound represented by formula (2) is useful as a production intermediate of the compound (1) of the present invention.

The aldehyde form (2-a), the compound (5), and the compound (7) employed in the above reactions may be known compounds, or may be produced through reaction for forming the aforementioned heterocycle X¹ or for forming ring B. For example, a bromoacetophenone compound (5) may be produced from an acetophenone compound through a known method (Synthesis. 1976, 194, 196, or Org. Synth, 1943, I, 127). Among these ring structures, a benzothiazole structure and a benzoxazole structure may be produced through reaction between an aldehyde compound and an aniline compound. The reaction is generally performed in a solvent at room temperature or elevated temperature. Dimethyl sulfoxide may be used as a solvent. The reaction temperature is preferably about 160° C.

The substituent of $X^1$, $X^2$ or ring B may be transformed through a variety of routine methods. For example, a trialkyltin group may be formed through reaction of the corresponding halogen form and a trialkyltin in the presence of a catalyst, for example, tetra(triphenylphosphine)palladium. The trialkyltin group may be transformed into a iodo group through reaction with iodine.

The compound (1) of the present invention produced through the aforementioned methods may be isolated as a free form or a salt thereof, followed by purification. Isolation and purification may be performed through known chemical operations such as extraction, recrystallization, chromatographic processes, etc.

A C-11-labeled compound for use in PET may be produced through, for example, the reactions shown below. Generally, in C-11-labeling reaction, methylation is performed by use of [$^{11}$C]methyl iodide or [$^{11}$C]methyl triflate, which have been produced from [$^{11}$C]CO$_2$ generated by means of a cyclotron as a starting material. When a precursor having an amino group, amido group, a hydroxy group, a thiol group, or the like is methylated, a C-11-labeled compound can be produced. Alternatively, a coupling reaction with an organic tin compound in the presence of a Pd catalyst can also produce a C-11-labeled compound. These methods are described with the following labeling scheme.

[F8]

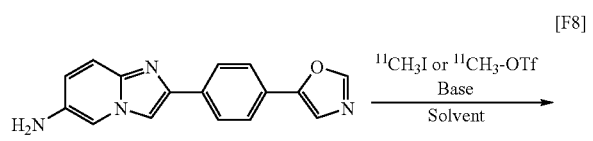

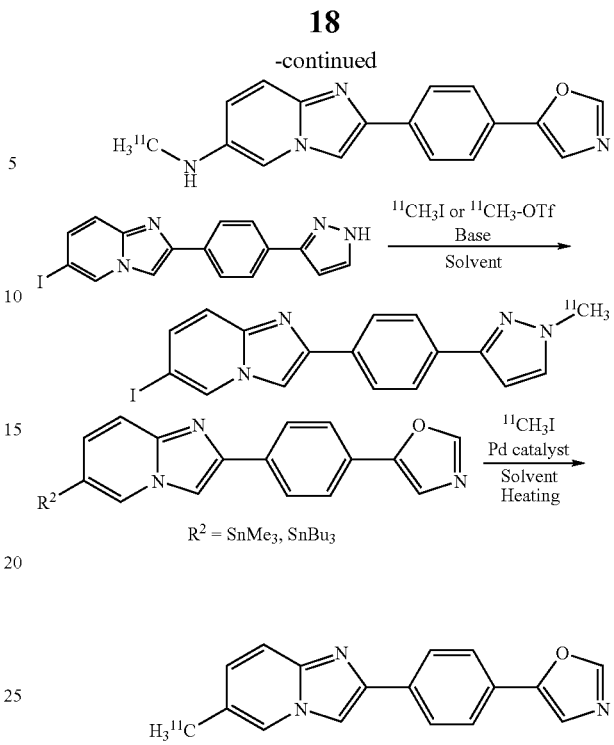

F-18-labeling is attained through the $F_2$ method (electrophilic substitution), the acetyl-hypofluorite method (electrophilic substitution), or the fluoride ion method (nucleophilic substitution). Since the $F_2$ method and the acetyl-hypofluorite method employ [$^{18}$F]F$_2$ with a carrier as a starting material, relative radioactivity tends to be lowered. Since the fluoride ion method employs carrier-less [$^{18}$F]F$^-$ as a starting material, a label compound having high relative radioactivity can be produced. Even though any of the methods is employed, use of a precursor having an appropriate leaving group results in production of a fluorine-labeled compound. These methods are described with the following labeling schemes.

[F9]

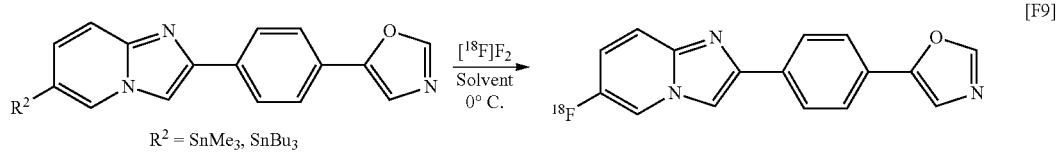

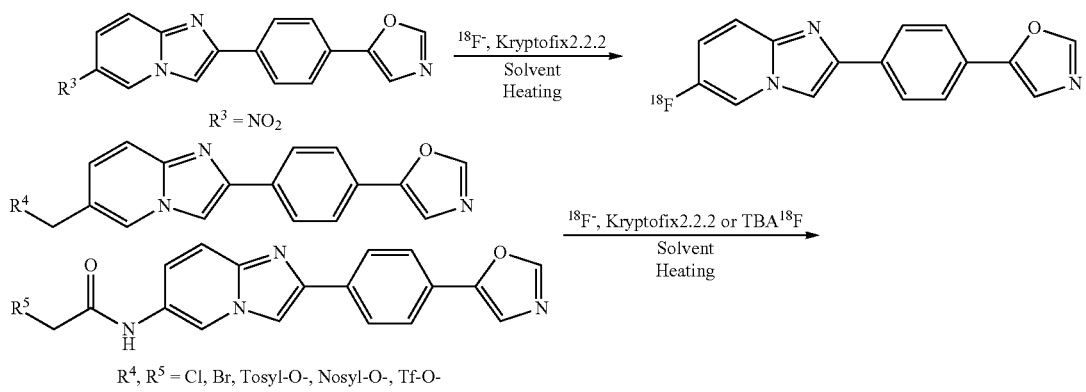

-continued
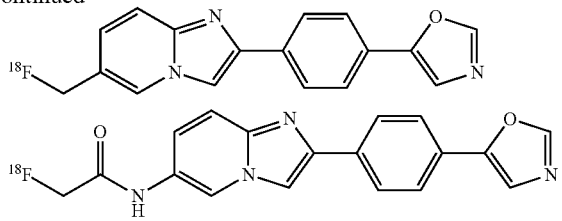
The compound (1) of the present invention having a chelate-forming group may be produced through, for example, the following procedure. The following reaction scheme shows the synthesis of a compound having the aforementioned (J) as a chelate-forming group.
[F10]
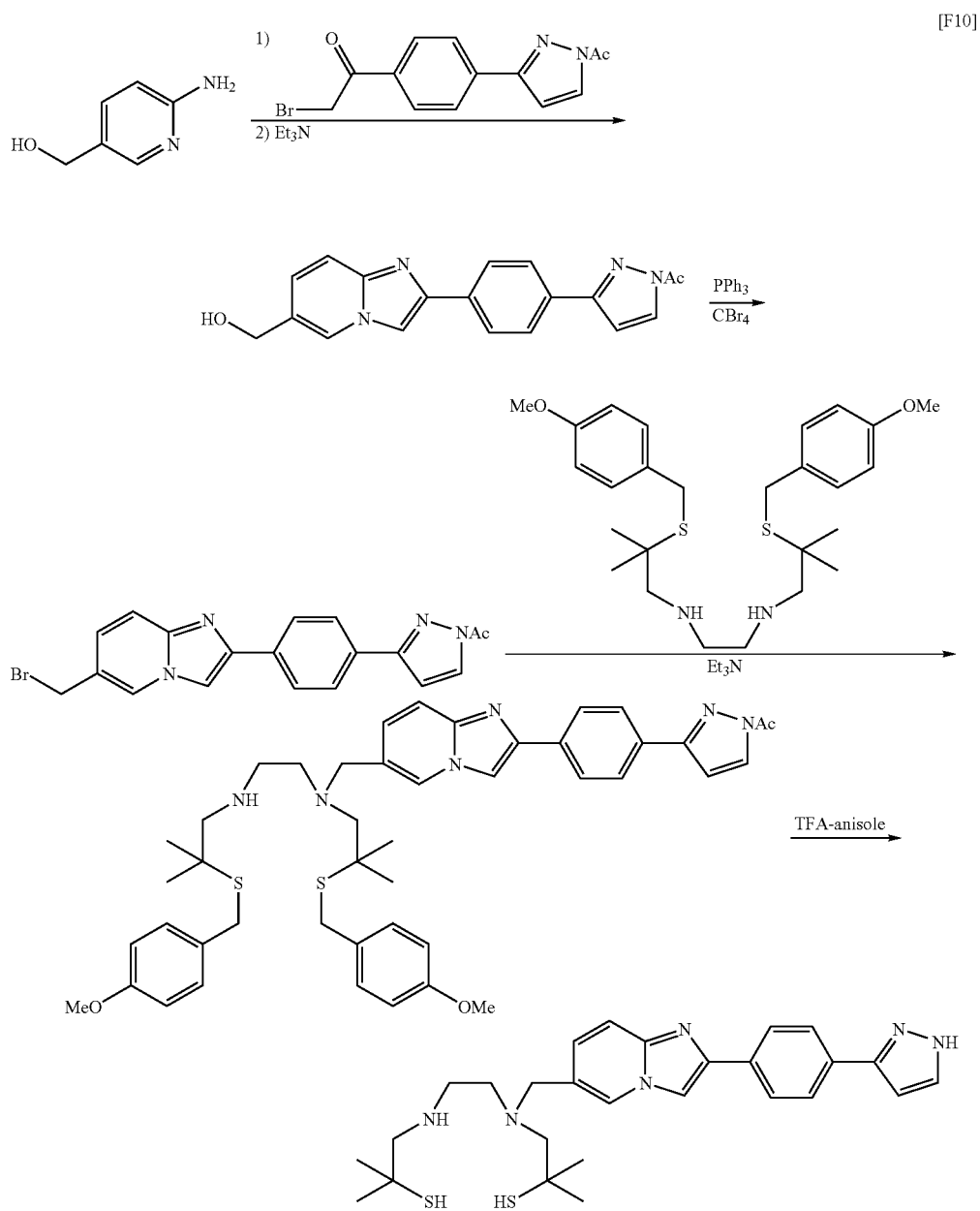

More specifically, (6-amino-3-pyridyl)methanol and 1-[4-(1-acetyl-1H-3-pyrazolyl)phenyl]-2-bromo-1-ethanone are dissolved in dioxane, and the solution is refluxed under heating. After cooling, precipitates are recovered through filtration, to thereby produce a hydrobromic acid salt of the title compound. The thus-obtained solid was dispersed in chloroform, and triethylamine is added to the suspension, followed by stirring at room temperature. The reaction mixture is washed with water and saturated saline and dried over magnesium sulfate, followed by removing the solvent under reduced pressure. The residue is purified through flash column chromatography, to thereby yield 1-(3-{4-[6-(hydroxymethyl)imidazo[1,2-a]pyridin-2-yl]phenyl}-1H-1-pyrazolyl)-1-ethanone. Subsequently, triphenylphosphine is added to a solution of 1-(3-{4-[6-(hydroxymethyl)imidazo[1,2-a]pyridin-2-yl]phenyl}-1H-1-pyrazolyl)-1-ethanone and carbon tetrabromide in tetrahydrofuran, followed by stirring at room temperature and extraction with chloroform. The extract is dried over magnesium sulfate, and the solvent is removed therefrom under reduced pressure. The residue is purified through flash column chromatography, to thereby yield 1-(3-{4-[6-(hydroxymethyl)imidazo[1,2-a]pyridin-2-yl]phenyl}-1H-1-pyrazolyl)-1-ethanone. Subsequently, 1-(3-{4-[6-(hydroxymethyl)imidazo[1,2-a]pyridin-2-yl]phenyl}-1H-1-pyrazolyl)-1-ethanone and N1,N2-di{2-[(4-methoxybenzyl)sulfanyl]-2-methylpropyl}-1,2-ethanediamine are dissolved in acetonitrile, and triethylamine is added to the solution, followed by refluxing under heating. After cooling, the mixture is extracted with chloroform. The extract is dried over magnesium sulfate, and the solvent is removed under reduced pressure. The residue is purified through flash column chromatography, to thereby yield 1-(3-{4-[6-({{2-[(4-methoxybenzyl)sulfanyl]-2-methylpropyl}[2-({2-[(4-methoxybenzylsulfanyl)]-2-methylpropyl}amino)ethyl]amino}methyl)imidazo[1,2-a]pyridin-2-yl]phenyl}-1H-1-pyrazolyl)-1-ethanone. Subsequently, 1-(3-{4-[6-({{2-[(4-methoxybenzyl)sulfanyl]-2-methylpropyl}[2-({2-[(4-methoxybenzylsulfanyl)]-2-methylpropyl}amino)ethyl]amino}methyl)imidazo[1,2-a]pyridin-2-yl]phenyl}-1H-1-pyrazolyl)-1-ethanone is dissolved in trifluoroacetic acid, and the solution is refluxed under heating. After cooling, water is added to a residue recovered through concentration under reduced pressure, followed by washing with dichloromethane. The aqueous layer is concentrated under reduced pressure, to thereby yield 2-methyl-1-[{2-[(2-methyl-2-sulfanylpropyl)amino]ethyl}({2-[4-(1H-3-pyrazolyl)phenyl]imidazo[1,2-a]pyridin-6-yl}methyl)amino]-2-propanethiol di-trifluoroacetic acid salt.

The following reaction scheme shows the synthesis of a compound having the aforementioned (F) as a chelate-forming group.

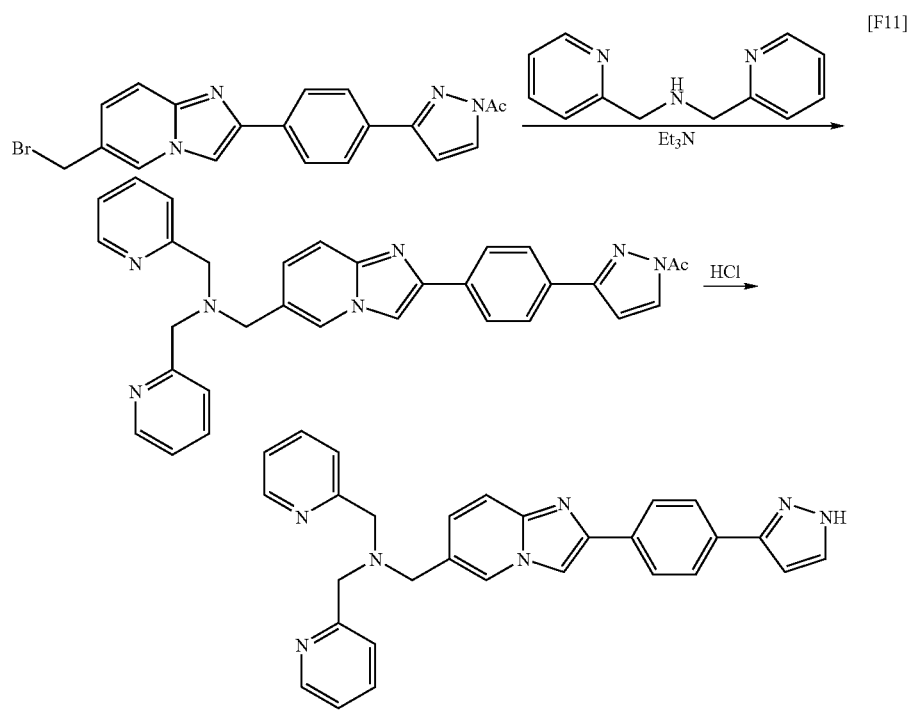

[F11]

More specifically, 1-(3-{4-[6-(hydroxymethyl)imidazo[1,2-a]pyridin-2-yl]phenyl}-1H-1-pyrazolyl)-1-ethanone and 1,2-dipicolylamine are dissolved in acetonitrile, and triethylamine is added to the solution, followed by refluxing. After cooling, the mixture is extracted with chloroform. The extract is dried over magnesium sulfate, and the solvent is removed under reduced pressure. The residue is purified through flash column chromatography, to thereby yield 1-{3-[4-(6-{[di(2-pyridylmethyl)amino]methyl}imidazo[1,2-a]pyridin-2-yl)phenyl]-1H-1-pyrazolyl}-1-ethanone. Subsequently, 1-{3-[4-(6-{[di(2-pyridylmethyl)amino]methyl}imidazo[1,2-a]pyridin-2-yl)phenyl]-1H-1-pyrazolyl}-1-ethanone is dissolved in ethanol, and 3N hydrochloric acid is added to the solution, followed by refluxing under heating. After cooling, the mixture is alkalified with aqueous sodium hydroxide and extracted with chloroform. The extract is dried over magnesium sulfate, and the solvent is removed under reduced pressure. The residue is purified through flash column chromatography, to thereby yield N,N-di(2-pyridylmethyl)-{2-[4-(1H-3-pyrazolyl)phenyl]imidazo[1,2-a]pyridin-6-yl}methanamine.

The following reaction scheme shows the synthesis of a compound having the aforementioned (D) and (E) as a chelate-forming group.

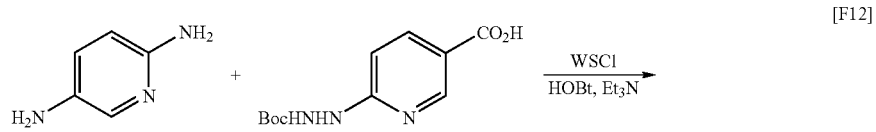

[F12]

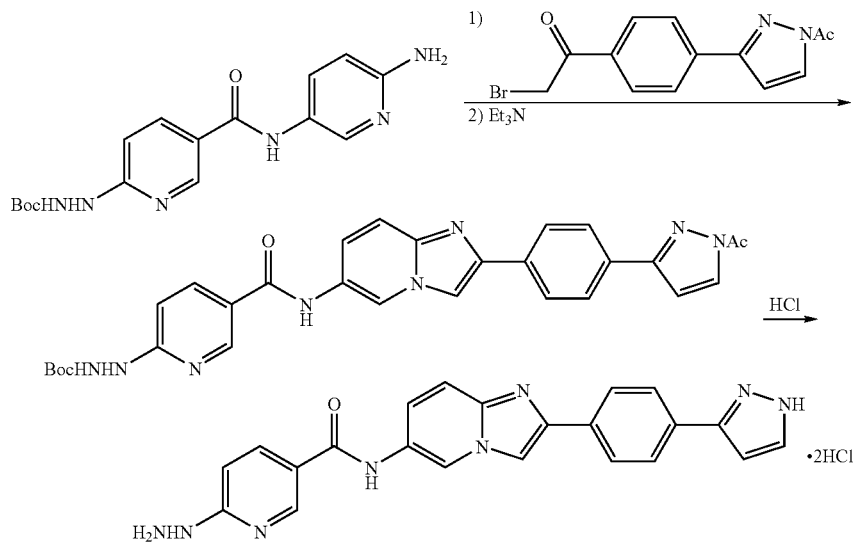

More specifically, 2,5-diaminopyridine and 6-[2-(tert-butoxycarbonyl)hydrazino]nicotic acid and 1-hydroxybenzotriazole are dissolved in N,N-dimethylformamide, and triethylamine and 1-ethyl-3-(3-dimethylaminopropyl)carbodiimide hydrochloride are added to the solution, followed by stirring at room temperature. Water is added to the reaction mixture, followed by extraction with dichloromethane. The extract is dried over magnesium sulfate, and the solvent is removed under reduced pressure. The residue is purified through flash column chromatography, to thereby yield tert-butyl 2-(5-{[(6-amino-3-pyridyl)amino]carbonyl}-2-pyridyl)-1-hydrazinecarboxylate. Subsequently, tert-butyl 2-(5-{[[(6-amino-3-pyridyl)amino]carbonyl}-2-pyridyl)-1-hydrazinecarboxylate and 1-[4-(1-acetyl-1H-3-pyrazolyl)phenyl]-2-bromo-1-ethanone are dissolved in dioxane, and the solution is refluxed under heating. After cooling, precipitates are recovered through filtration, to thereby produce a hydrobromic acid salt. The thus-obtained solid was suspended in chloroform, and triethylamine is added to the suspension, followed by stirring at room temperature. The reaction mixture is washed with water and saturated saline and dried over magnesium sulfate, followed by removing the solvent under reduced pressure. The residue is purified through flash column chromatography, to thereby yield tert-butyl 2-{5-[({2-[4-(1-acetyl-1H-3-pyrazolyl)phenyl]imidazo[1,2-a]pyridin-6-yl}amino) carbonyl]}-1-hydrazinecarboxylate. Subsequently, tert-butyl 2-{5-[({2-[4-(1-acetyl-1H-3-pyrazolyl)phenyl]imidazo[1,2-a]pyridin-6-yl}amino) carbonyl]}-1-hydrazinecarboxylate is dissolved in ethanol, and 3N hydrochloric acid is added to the solution, followed by refluxing under heating. The precipitated solid is recovered through filtration, to thereby yield N-3-{2-[4-(1H-3-pyrazolyl)phenyl]imidazo[1,2-a]pyridin-6-yl}-6-hydrazinonicotinamide dihydrochloride.

Chelate labeling of the compound (1) of the present invention having a chelate-forming group is performed through, for example, the following procedure. Generally, Tc-99m labeling reaction employs sodium pertechnetate as a starting material. In one labeling method, a mixed solution of the Tc source and a ligand compound is allowed to react in the co-presence of a reducing agent. Alternatively, a technetium intermediate compound produced through reduction of a starting sodium pertechnetate is subjected to ligand-exchange reaction, to thereby produce a Tc-99m-labeled compound. These methods are described with the following labeling scheme.

[F13]

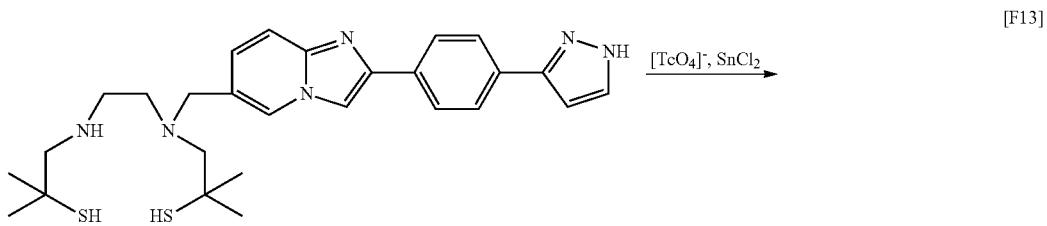

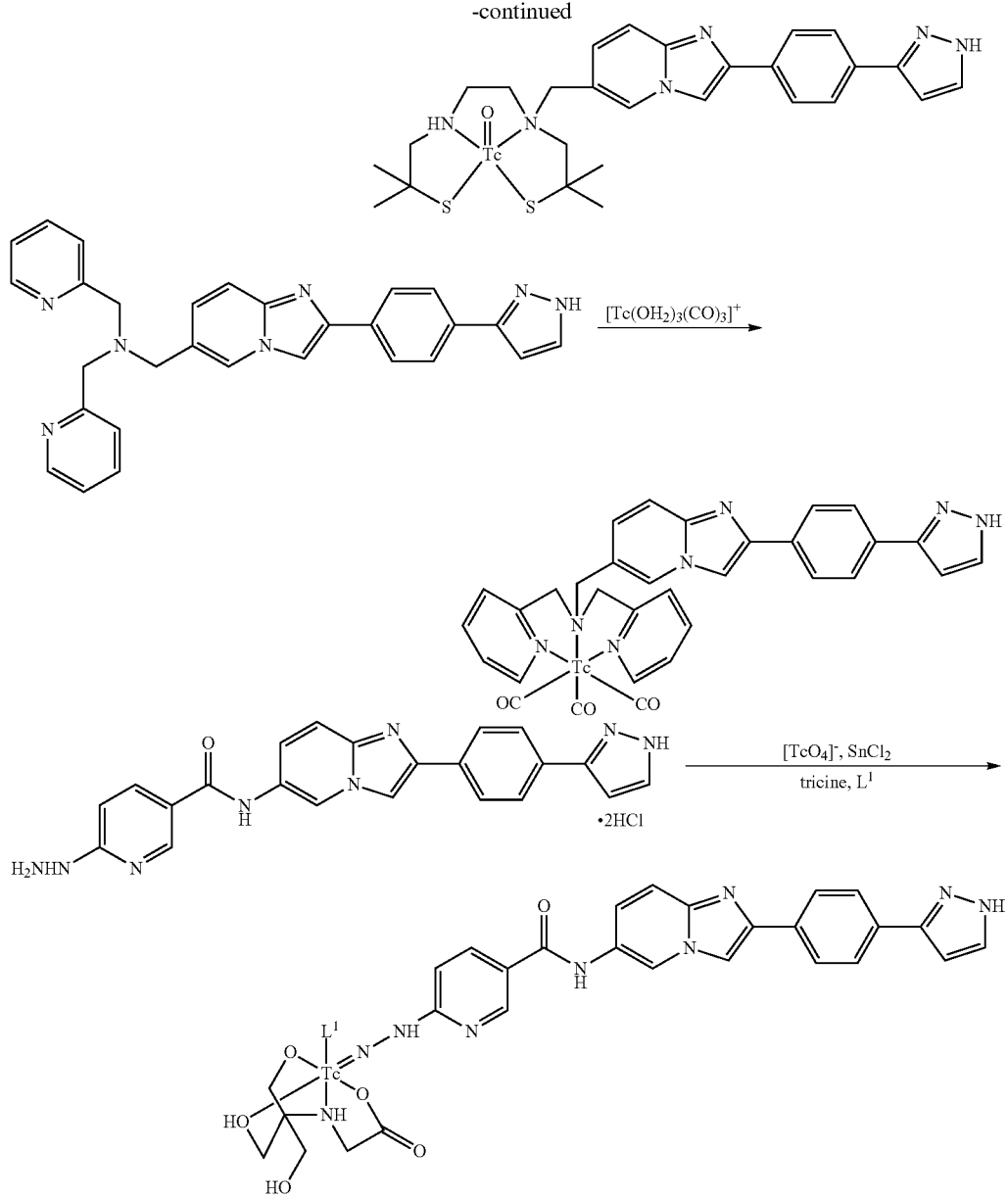

L¹ = TPPTS, TPPDS, TPPMS, NIC, AP

The compound (1) of the present invention passes through the blood-brain barrier to enter the brain, and exhibits high binding affinity to amyloid aggregates or amyloid deposits. Also, since the compound has high metabolism stability, and no metabolite thereof is present in the brain, the compound is useful for specifically imaging amyloid aggregates or amyloid deposits in the brain. In other words, the compound (1) of the present invention is useful as an imaging agent, particularly an amyloid imaging agent. Therefore, when a labeled compound of the compound (1) of the present invention is employed, image diagnosis of a disease caused by amyloid aggregation and/or deposition can be realized. Specifically, amyloidosis such as Alzheimer's disease, Down syndrome, Creutzfeldt-Jakob disease, type-II diabetes, dialysis amyloidosis, AA amyloidosis, Gerstmann-Straeussler-Scheinker syndrome, Muckle-Wells syndrome, localized atrial amyloidosis, medullary thyroid cancer, cutaneous amyloidosis, localized nodular amyloidosis, AL amyloidosis, AH amyloidosis, familial amyloid polyneuropathy, senile systemic amyloidosis, cerebrovascular amyloidosis, familial Mediterranean fever, Parkinson disease, tauopathy, ALS, or CAG repeat disease can be early diagnosed.

Since the compound (1) of the present invention exhibits an inhibitory effect on aggregation and/or deposition of amyloid, the compound is a useful preventive and/or therapeutic drug for a disease caused by aggregation and/or deposition of amyloid; i.e., amyloidosis, for example, Alzheimer's disease, Down syndrome, Creutzfeldt-Jakob disease, type-II diabetes, dialysis amyloidosis, AA amyloidosis, Gerstmann-Straeussler-Scheinker syndrome, Muckle-Wells syndrome, localized atrial amyloidosis, medullary thyroid cancer, cutaneous amyloidosis, localized nodular amyloidosis, AL amyloidosis, AH amyloidosis, familial amyloid polyneuropathy, senile systemic amyloidosis, cerebrovascular amyloidosis, familial Mediterranean fever, Parkinson disease, tauopathy, ALS, or CAG repeat disease. Furthermore, the compound of the invention is a useful screening tool for a preventive and/or therapeutic drug for these diseases.

When employed as a diagnostic drug, the compound (1) of the present invention may be used topically or systemically and may be administered intravenously, intraarterially, intraspinally, or in a similar manner. Any drug form thereof may be selected in accordance with use or a target disease. According to the present invention, amyloid deposits can be imaged by administering, to a subject in need thereof, a labeled compound of the compound (1) in a detectable amount, allowing to pass a sufficient period of time (e.g., 30 minutes to 48 hours) for binding the labeled compound to the amyloid deposits, and detecting the labeled compound which has been bound to the amyloid deposits. In the imaging procedure, the amyloid deposits-bound labeled compound is detected by means of an imaging apparatus (e.g., MRS/MRI, SPECT, planer scintillation imaging, or PET) suitable for detecting a region of a biological subject corresponding to the target disease. The diagnosis protocol varies in accordance with conditions so as to fit the target diseases and patients and a detection device.

Examples of the non-aqueous medium for administration include propylene glycol, vegetable oil, and organic ester. Examples of the aqueous medium include water, an alcoholic solution, an aqueous solution, and physiological saline.

When employed as a pharmaceutical drug, the compound (1) of the present invention may be administered orally or parenterally. Any drug form thereof may be selected in accordance with a use or an object disease. Examples of the oral drug form include tablets, pills, capsules, powders, and oral medicines. Examples of the parenteral drug form include injections, eye-drops, suppositories, suspensions, ointments, cataplasms, liniments, lotions, aerosols, and plasters. During forming these drugs, additives such as a vehicle, a binder, a disintegrant, a fluidizer, a suspending agent, a humectant, and a solubilizing agent may be appropriately added, so long as the effects of the compound (1) of the present invention are not impaired.

The dose of the compound (1) of the present invention may be appropriately determined in accordance with the type and severity of the target disease, administration route, compound to be administered, and the age, sex, and body weight of the patient. For example, in the case of oral administration, the daily does of the compound may be about 0.1 mg to about 1,000 mg for an adult. The timing of administration may be before meal, between meals, after meal, or before sleeping. The administration may be performed singly or at several times in a divided manner. When the compound (1) of the present invention is labeled with a radioactive nuclide, the dose may be appropriately determined in consideration of measurement conditions of a radio-imaging apparatus (e.g., SPECT or PET apparatus) and exposure of a patient. For example, as reduced to radioactivity, the dose is 37 GBq to 37 GBq, preferably 111 MBq to 740 MBq.

When screening for a preventive and/or therapeutic drug for a disease caused by amyloid aggregation and/or deposition is performed by use of the compound (1) of the present invention, binding ability of a specimen to amyloid is detected in vitro or in vivo by use of the compound (1) of the present invention. For example, in the case of in vitro screening, (i) a specimen is brought into contact with amyloid (e.g., amyloid β aggregates), and binding ability of the specimen to amyloid is detected by use of the compound (1) of the present invention, or (ii) a specimen is brought into contact with amyloid, and the degree of amyloid aggregation and/or deposition is determined by use of the compound (1) of the present invention.

In the case of in vivo screening, in one possible approach, a specimen is administered to an animal (human or non-human animal) in which amyloid has been formed, and the degree of amyloid aggregation and/or deposition is determined by use of the compound (1) of the present invention.

When inhibition of binding of a specimen to amyloid (or the like) has been confirmed by use of the compound (1) of the present invention, the specimen can be found to be a useful preventive and/or therapeutic drug for an amyloid-related disease caused by amyloid protein (amyloidosis).

EXAMPLES

The present invention will next be described in detail by way of examples, which should not be construed as limiting the invention thereto.

Referential Example 1

4-(6-Iodoimidazo[1,2-a]pyridin-2-yl)benzonitrile (1)

2-Amino-5-iodopyridine (1.0 g) and 2-bromo-4'-cyanoacetophenone (1.02 g) were dissolved in ethanol (30 mL), and sodium hydrogencarbonate (382 mg) was added to the solution, followed by refluxing for 16 hours. Water (10 mL) was added to the reaction mixture, and the mixture was left to cool. The precipitated matter was recovered through filtration and dried, to thereby yield the title compound (1.27 g).

$^1$H-NMR (400 MHz, DMSO-$d_6$) δ: 7.54 (1H, d, J=9.5 Hz), 7.62 (1H, dd, J=1.2, 9.3 Hz), 7.94 (2H, d, J=8.3 Hz), 8.14 (2H, d, J=8.5 Hz), 8.56 (1H, s), 9.02 (1H, s).

EI-MS m/z: 345 (M)$^+$.

Referential Example 2

4-(6-Iodoimidazo[1,2-a]pyridin-2-yl)benzaldehyde (2)

4-(6-Iodoimidazo[1,2-a]pyridin-2-yl)benzonitrile (1.27 g) was added to a mixture of tetrahydrofuran (15 mL) and dichloromethane (15 mL), followed by stirring under ice cooling. Diisobutylaluminum hydride (7.8 mL) was added dropwise to the reaction mixture, and the resultant mixture was stirred at the same temperature for 15 minutes and then at room temperature for 4 hours. Aqueous saturated ammonium chloride solution (2 mL) was added dropwise to the reaction mixture, followed by stirring at room temperature for 1 hour. Subsequently, magnesium sulfate and diethyl ether were added to the reaction mixture, followed by further stirring for 1 hour. The solvent was evaporated, and the residue was purified through silica gel column chromatography (dichloromethane:methanol=95:5). The purified product was concentrated under reduced pressure, to thereby yield the title compound (1.03 g).

$^1$H-NMR (400 MHz, DMSO-$d_6$) δ: 7.47 (2H, d, J=1.2 Hz) 7.98 (2H, d, J=8.3 Hz), 8.18 (2H, d, J=8.3 Hz), 8.49 (1H, s), 8.95 (1H, t, J=1.2 Hz), 10.02 (1H, s).

Example 1

5-[4-(6-Iodoimidazo[1,2-a]pyridin-2-yl)phenyl]-1,3-oxazole (3)

4-(6-Iodoimidazo[1,2-a]pyridin-2-yl)benzaldehyde (647 mg) and p-toluenesulfonylmethyl isocyanide (454 mg) were dissolved in methanol (10 mL), and potassium carbonate (321 mg) was added to the solution at room temperature, followed by refluxing for 13 hours. The precipitated product was recovered through filtration and dried, to thereby yield the title compound (330 mg).

$^1$H-NMR (400 MHz, DMSO-d$_6$) δ: 7.45 (2H, d, J=1.2 Hz), 7.74 (1H, s), 7.81 (2H, d, J=8.5 Hz), 8.06 (2H, d, J=8.5 Hz), 8.39 (1H, s), 8.47 (1H, s), 8.92 (1H, t, J=1.2 Hz).

EI-MS m/z: 387 (M)$^+$.

Referential Example 3

4-(6-Iodoimidazo[1,2-a]pyridin-2-yl)-1-benzenecarbothioamide (6)

4-(6-Iodoimidazo[1,2-a]pyridin-2-yl)benzonitrile (345 mg) and thioacetamide (150 mg) were added to a saturated solution (5 mL) of hydrogen chloride in dimethylformamide. The mixture was heated at 80° C. for 4 hours, and the solvent was evaporated. Saturated sodium hydrogencarbonate was added to the residue, followed by recovering the solid through filtration and drying, to thereby yield the title compound (269 mg).

$^1$H-NMR (400 MHz, DMSO-d$_6$) δ: 7.45 (2H, d, J=1.0 Hz), 7.98 (4H, s), 8.41 (1H, s), 8.92 (1H, s), 9.52 (1H, s), 9.86 (1H, s).

FAB-MS m/z: 380 (M+H)$^+$.

Example 2

2-[4-(6-Iodoimidazo[1,2-a]pyridin-2-yl)phenyl]-1,3-thiazole (7)

4-(6-Iodoimidazo[1,2-a]pyridin-2-yl)-1-benzenecarbothioamide (249 mg) was dissolved in ethanol (10 mL). Triethylamine (91 μL) and chloroacetaldehyde (155 μL) were added to the solution, and the mixture was refluxed for 18 hours. Water was added to the reaction mixture, followed by extraction with dichloromethane-methanol. The solvent was evaporated, and the residue was purified through silica gel column chromatography (dichloromethane:methanol=100:5), followed by concentration under reduced pressure, to thereby yield the title compound (103 mg).

$^1$H-NMR (400 MHz, DMSO-d$_6$) δ: 7.45 (2H, s), 7.80 (1H, dd, J=0.7, 3.2 Hz) 7.94 (1H, dd, J=0.7, 3.2 Hz), 8.02 (2H, d, J=8.1 Hz), 8.08 (2H, d, J=8.3 Hz), 8.41 (1H, s), 8.93 (1H, d, J=1.0 Hz).

EI-MS m/z: 403 (M)$^+$.

Referential Example 4

1-[4-(6-Iodoimidazo[1,2-a]pyridin-2-yl)phenyl]-1-ethanol (8)

4-(6-Iodoimidazo[1,2-a]pyridin-2-yl)benzaldehyde (820 mg) was dissolved in tetrahydrofuran (25 mL), and the solution was stirred under ice cooling. Methyl magnesium bromide (787 mL) was added dropwise to the reaction mixture, followed by stirring for 15 minutes under ice cooling and then for 5 hours at room temperature. Aqueous saturated ammonium chloride solution (25 mL) was added dropwise to the reaction mixture, and the mixture was stirred at room temperature for 1 hour. Water was added to the reaction mixture, followed by extraction with dichloromethane-methanol. Subsequently, the solvent was evaporated, and the residue was purified through silica gel column chromatography (dichloromethane:methanol=97:3), followed by concentration under reduced pressure, to thereby yield the title compound (579 mg).

$^1$H-NMR (400 MHz, CDCl$_3$) δ: 1.53 (3H, d, J=6.3 Hz), 4.93 (1H, q, J=6.5 Hz), 7.32 (1H, dd, J=1.7, 9.4 Hz), 7.41 (2H, d, J=7.6 Hz), 7.44 (1H, s), 7.78 (1H, s), 7.89 (2H, d, J=8.1 Hz), 8.37 (1H, s).

Referential Example 5

1-[4-(6-Iodoimidazo[1,2-a]pyridin-2-yl)phenyl]-1-ethanone (9)

Manganese dioxide (691 mg) was added to a solution of 1-[4-(6-iodoimidazo[1,2-a]pyridin-2-yl)phenyl]-1-ethanol (579 mg) in chloroform (50 mL), and the mixture was refluxed for 8 hours. The reaction mixture was filtered through Celite, and the mother liquor was concentrated. The residue was purified through silica gel column chromatography (dichloromethane:methanol=95:5), followed by concentration under reduced pressure, to thereby yield the title compound (371 mg).

$^1$H-NMR (400 MHz, DMSO-d$_6$) δ: 2.60 (3H, s), 7.46 (2H, s), 8.03 (2H, d, J=8.3 Hz), 8.09 (2H, J=8.3 Hz), 8.46 (1H, s), 8.93 (1H, s).

EI-MS m/z: 362 (M)$^+$.

Referential Example 6

(E)-3-(Dimethylamino)-1-[4-(6-iodoimidazo[1,2-a]pyridin-2-yl)phenyl]-2-propen-1-one (10)

N,N-dimethylformamide dimethyl acetal (363 μL) was added dropwise to a solution (50 mL) of 1-[4-(6-iodoimidazo[1,2-a]pyridin-2-yl)phenyl]-1-ethanone (495 mg) in dimethylformamide, and the mixture was heated at 150° C. for 16 hours. The reaction mixture was concentrated, and the residue was purified through silica gel column chromatography (dichloromethane:methanol=97:3), followed by concentration under reduced pressure, to thereby yield the title compound (274 mg).

$^1$H-NMR (400 MHz, CDCl$_3$) δ: 2.97 (3H, br), 3.16 (3H, br), 5.77 (1H, d, J=12.4 Hz), 7.35 (1H, dd, J=1.5, 10.9 Hz), 7.44 (1H, d, J=9.3 Hz), 7.83 (1H, d, J=12.4 Hz), 7.86 (1H, s), 7.98 (4H, d, J=0.5 Hz), 8.40 (1H, s).

Example 3

6-Iodo-2-[4-(1H-3-pyrazolyl)phenyl]imidazo[1,2-a]pyridine (11)

Hydrazine monohydrate (100 μL) was added to a solution (30 mL) of (E)-3-(dimethylamino)-1-[4-(6-iodoimidazo[1,2-a]pyridin-2-yl)phenyl]-2-propen-1-one (344 mg) in ethanol, and the mixture was refluxed for 3 hours. The reaction mixture was left to cool, and the precipitated matter was recovered through filtration and dried, to thereby yield the title compound (290 mg).

$^1$H-NMR (400 MHz, DMSO-d$_6$) δ: 6.75 (1H, d, J=1.7 Hz), 7.44 (2H, t, J=9.8 Hz), 7.79 (1H, br), 7.87 (2H, d, J=8.0 Hz), 7.98 (2H, d, J=8.0 Hz), 8.34 (1H, s), 8.91 (1H, s), 12.90 (1H, br).

EI-MS m/z: 386 (M)$^+$.

Referential Example 7

2-Bromo-1-[4-(6-iodoimidazo[1,2-a]pyridin-2-yl)phenyl]-1-ethanone (14)

Dichloromethane (9 mL) and triethylamine (355 µL) were added to 1-[4-(6 iodoimidazo[1,2-a]pyridin-2-yl)phenyl]-1-ethanone (464 mg), and the mixture was stirred under ice cooling.

Bromotrimethylsilane (379 µL) was added dropwise to the reaction mixture, and the mixture was stirred at room temperature for 22 hours. Water was added to the reaction mixture, and the mixture was extracted with dichloromethane, followed by drying over sodium sulfate. The solvent was concentrated under reduced pressure, and the concentration residue was dissolved in tetrahydrofuran (7 mL). N-bromosuccinimide (228 mg) was added to the solution, followed by stirring at room temperature for 1 hour. The solvent was evaporated, and the residue was purified through silica gel column chromatography (dichloromethane:methanol=98:2), followed by concentration under reduced pressure, to thereby yield the title compound (441 mg).

$^1$H-NMR (400 MHz, DMSO-$d_6$) δ: 4.95 (2H, s), 7.47 (2H, s), 8.07 (2H, d, J=8.3 Hz), 8.12 (2H, d, J=8.3 Hz), 8.49 (1H, s), 8.94 (1H, s).

EI-MS m/z: 442 (M+H)$^+$.

Example 4

2-[4-(1H-4-Imidazolyl)phenyl]-6-iodoimidazo[1,2-a]pyridine (15)

A solution (2 mL) of 2-bromo-1-[4-(6-iodoimidazo[1,2-a]pyridin-2-yl)phenyl]-1-ethanone (100 mg) in formamide was heated at 190° C. for 1 hour. The solution was left to cool to room temperature. Subsequently, water and 2N sodium hydroxide solution were added to the reaction mixture, followed by extraction with dichloromethane-methanol. The solvent was evaporated, and the residue was purified through silica gel column chromatography (dichloromethane:methanol=9:1), followed by concentration under reduced pressure, to thereby yield the title compound (81 mg).

$^1$H-NMR (400 MHz, DMSO-$d_6$) δ: 7.42 (2H, s), 7.67 (1H, s), 7.71 (1H, s), 7.85 (2H, d, J=8.3 Hz), 7.92 (2H, d, J=8.1 Hz), 8.30 (1H, s), 8.90 (1H, s), 12.18 (1H, br).

EI-MS m/z: 386 (M)$^+$.

Referential Example 8

N-Hydroxy-4-(6-iodoimidazo[1,2-a]pyridin-2-yl)benzamidine (16)

Hydroxylamine hydrochloride (208 mg) and potassium carbonate (415 mg) were added to a solution (10 mL) of 4-(6-iodoimidazo[1,2-a]pyridin-2-yl)benzonitrile (345 mg) in methanol, followed by refluxing for 14 hours. The mixture was left to cool, and the formed crystals were recovered through filtration. The crystals were washed with water and dried, to thereby yield the title compound (279 mg).

$^1$H-NMR (400 MHz, DMSO-$d_6$) δ: 5.82 (2H, s), 7.43 (2H, s), 7.74 (2H, d, J=8.3 Hz), 7.94 (2H, d, J=8.3 Hz), 8.34 (1H, s), 8.91 (1H, s), 9.65 (1H, s).

EI-MS m/z: 378 (M)$^+$.

Example 5

3-[4-(6-Iodoimidazo[1,2-a]pyridin-2-yl)]-1,2,4-oxadiazole (17)

N-Hydroxy-4-(6-iodoimidazo[1,2-a]pyridin-2-yl)benzamidine (265 mg) was added to trimethyl orthoformate (2.3 mL), followed by refluxing for 18 hours. The mixture was left to cool, and the solvent was concentrated under reduced pressure. Dichloromethane-methanol solution was added to the concentration residue, and the precipitated matter was recovered through filtration and dried, to thereby yield the title compound (217 mg).

$^1$H-NMR (400 MHz, DMSO-$d_6$) δ: 7.46 (2H, s), 8.11 (2H, d, J=8.3 Hz), 8.16 (2H, d, J=8.3 Hz), 8.44 (1H, s), 8.94 (1H, d, J=1.0 Hz), 9.71 (1H, d, J=0.5 Hz).

EI-MS m/z: 388 (M)$^+$.

Example 6

6-Iodo-2-[4-(1H-1,2,3,4-tetrazol-5-yl)phenyl]imidazo[1,2-a]pyridine (19)

Trimethylaluminum (150 µL) and azidotrimethylsilane (42 µL) were added to a solution (1 mL) of 4-(6-iodoimidazo[1,2-a]pyridin-2-yl)benzonitrile (104 mg) in toluene, followed by heating at 80° C. for 2 hours. The mixture was left to cool to room temperature, and 6N hydrochloric acid solution was added thereto. The precipitated matter was recovered through filtration and dried, to thereby yield the title compound (17 mg).

$^1$H-NMR (400 MHz, DMSO-$d_6$) δ: 7.55-7.68 (2H, m), 8.18 (4H, q, J=8.3 Hz), 8.54 (1H, s), 9.05 (1H, s).

Example 7

5-[4-(6-Iodoimidazo[1,2-a]pyridin-2-yl)phenyl]isooxazole (20)

Hydroxylamine hydrochloride (53 mg) was added to a solution (5 mL) of (E)-3-(dimethylamino)-1-[4-(6-iodoimidazo[1,2-a]pyridin-2-yl)phenyl]-2-propen-1-one (104 mg) in ethanol, followed by refluxing for 2 hours. The solvent was evaporated, and the residue was purified through silica gel chromatography (dichloromethane:methanol=97:3), to thereby yield the title compound (24 mg).

$^1$H-NMR (400 MHz, DMSO-$d_6$) δ: 7.09 (1H, dd, J=0.7, 2.0 Hz), 7.47 (2H, s), 7.97 (2H, d, J=7.8 Hz), 8.21 (2H, d, J=8.0 Hz), 8.45 (1H, s), 8.68 (1H, dd, J=1.0, 2.0 Hz), 8.94 (1H, d, J=1.0 Hz).

EI-MS m/z: 387 (M)$^+$.

Referential Example 9

1-[4-(1,3-Oxazol-5-yl)phenyl]-1-ethanone (21)

4-Acetylbenzaldehyde (2.96 g) and p-toluenesulfonylmethylisocyanate (4.69 g) were dissolved in methanol (200 mL). Potassium carbonate (3.32 g) was added to the solution, and the mixture was stirred at room temperature overnight. Water was added to the reaction mixture, followed by extraction with ethyl acetate. The solvent was evaporated, and the residue was purified through silica gel column chromatography (dichloromethane:methanol=100:1), followed by concentration under reduced pressure, to thereby yield the title compound (3.14 g).

$^1$H-NMR (400 MHz, CDCl$_3$) δ: 2.63 (3H, s), 7.49 (1H, s), 7.75 (2H, d, J=8.3 Hz), 7.97 (1H, s), 8.02 (2H, d, J=8.3 Hz).

Referential Example 10

2-Bromo-1-[4-(1,3-oxazol-5-yl)phenyl]-1-ethanone (22)

1-[4-(1,3-Oxazol-5-yl)phenyl]-1-ethanone (2.81 g) and triethylamine (6.27 mL) were dissolved in dichloromethane mL), and bromotrimethylsilane (3.96 mL) was added dropwise to the solution under ice cooling. The mixture was stirred at room temperature overnight under argon. The reaction mixture was washed sequentially with water and saturated saline, followed by drying over magnesium sulfate. The solvent was evaporated under reduced pressure, and the formed brown oily matter was dissolved in tetrahydrofuran mL). Subsequently, N-bromosuccinimide (2.67 g) was added to the solution, followed by stirring at room temperature for 30 minutes. Water was added to the reaction mixture, and the mixture was extracted with ethyl acetate. The solvent was evaporated, and the residue was purified through flash column chromatography (dichloromethane), followed by concentration under reduced pressure. The obtained solid was recovered through filtration by use of n-hexane, to thereby yield the title compound (3.35 g).

$^1$H-NMR (400 MHz, CDCl$_3$) δ: 4.45 (2H, s), 7.52 (1H, s), 7.78 (2H, d, J=8.3 Hz), 7.99 (1H, s), 8.06 (2H, d, J=8.3 Hz).

Referential Example 11

5-[4-(6-Bromoimidazo[1,2-a]pyrimidin-2-yl)phenyl]-1,3-oxazole (23)

2-Amino-5-bromopyrimidine (348 mg) and 2-bromo-1-[4-(1,3-oxazol-5-yl)phenyl]-1-ethanone (532 mg) were suspended in 1,4-dioxane (20 mL), followed by refluxing under heating overnight. Immediately after refluxing, the reaction mixture was filtered without being cooled, followed by washing with heated 1,4-dioxane and drying, to thereby yield the title compound (587 mg).

$^1$H-NMR (400 MHz, DMSO-d$_6$) δ: 7.80 (1H, s), 7.88 (2H, d, J=8.3 Hz), 8.13 (2H, d, J=8.3 Hz), 8.50 (1H, s), 8.51 (1H, s), 8.77 (1H, d, J=2.2 Hz), 9.47 (1H, d, J=2.2 Hz).

EI-MS m/z: 340 (M)$^+$.

Referential Example 12

5-{4-[6-(1,1,1-Tributylstannyl)imidazo[1,2-a]pyrimidin-2-yl]phenyl}-1,3-oxazole (24)

5-[4-(6-Bromoimidazo[1,2-a]pyrimidin-2-yl)phenyl]-1,3-oxazole (171 mg) was suspended in N,N-dimethylformamide (10 mL). Triethylamine (139 μL), bis(tributyltin) (505 μL) and tetrakis(triphenylphosphine)palladium (catalytic amount) were added to the suspension, followed by stirring at 120° C. overnight under argon. The reaction mixture was diluted with methanol (20 mL), and filtered through Celite. The filtrate was concentrated under reduced pressure, and the residue was subjected to flash chromatography. A fraction eluted by use of an eluent of n-hexane-ethyl acetate=1:1 was concentrated under reduced pressure, to thereby yield a pale yellow oily product. The product was purified through NH-silica gel column chromatography (n-hexane:ethyl acetate 2:1), followed by concentration under reduced pressure, to thereby yield the title compound (92 mg).

$^1$H-NMR (400 MHz, CDCl$_3$) δ: 0.91 (9H, t, J=7.3 Hz), 1.16-1.20 (6H, m), 1.36 (6H, q, J=7.3 Hz), 1.54-1.61 (6H, m), 7.40 (1H, s), 7.74 (2H, d, J=8.3 Hz), 7.82 (1H, s), 7.93 (1H, s), 8.11 (2H, d, J=8.3 Hz), 8.29 (1H, d, J=1.5 Hz), 8.49 (1H, d, J=1.5 Hz).

EI-MS m/z: 552 (M)$^+$.

HR-EI-MS m/z: 552.1922 (calcd. for C$_{27}$H$_{36}$N$_4$OSn; 552.1916).

Example 8

5-[4-(6-Iodoimidazo[1,2-a]pyrimidin-2-yl)phenyl]-1,3-oxazole (25)

5-{4-[6-(1,1,1-Tributylstannyl)imidazo[1,2-a]pyrimidin-2-yl]phenyl}-1,3-oxazole (77 mg) was dissolved in tetrahydrofuran (2 mL), and a solution of iodine (36 mg) in tetrahydrofuran (360 μL) was added to the solution, followed by stirring at room temperature for 5 minutes. The solvent was evaporated under reduced pressure, and the solid was recovered through filtration, followed by washing with ethanol, to thereby yield the title compound (40 mg).

$^1$H-NMR (400 MHz, DMSO-d$_6$) δ: 7.76 (1H, s), 7.83 (2H, d, J=8.3 Hz), 8.11 (2H, d, J=8.3 Hz), 8.34 (1H, s), 8.47 (1H, s), 8.62 (1H, d, J=2.2 Hz), 9.33 (1H, d, J=2.2 Hz).

EI-MS m/z: 388 (M)$^+$.

HR-EI-MS m/z: 387.9839 (calcd. for C$_{15}$H$_9$N$_4$OI; 387.9821).

Referential Example 13

4-(6-Bromoimidazo[1,2-a]pyridin-2-yl)benzonitrile (26)

The procedure of Referential Example 1 was repeated, except that 2-amino-5-bromopyridine (692 mg) and 2-bromo-4'-cyanoacetophenone (450 mg) were used, to thereby yield the title compound (500 mg).

$^1$H-NMR (400 MHz, DMSO-d$_6$) δ: 7.46 (1H, dd, J=1.7, 9.5 Hz), 7.63 (1H, d, J=9.8 Hz), 7.91 (2H, d, J=8.3 Hz), 8.15 (2H, d, J=8.3 Hz), 8.56 (1H, s), 8.94 (1H, d, J=1.0 Hz).

Referential Example 14

4-(6-Bromoimdazo[1,2-a]pyridin-2-yl)benzaldehyde (27)

The procedure of Referential Example 2 was repeated, except that 4-(6-bromoimidazo[1,2-a]pyridin-2-yl)benzonitrile mg) was used, to thereby yield the title compound (260 mg).

$^1$H-NMR (400 MHz, DMSO-d$_6$) δ: 7.41 (1H, dd, J=1.5, 9.5 Hz), 7.61 (1H, d, J=9.5 Hz), 7.98 (2H, d, J=8.1 Hz), 8.19 (2H, d, J=8.1 Hz), 8.53 (1H, s), 8.92 (1H, t, J=1.0 Hz), 10.02 (1H, s).

Example 9

5-[4-(6-Bromoimidazo[1,2-a]pyridin-2-yl)phenyl]-1,3-oxazole (28)

The procedure of Example 1 was repeated, except that 4-(6-bromoimidazo[1,2-a]pyridin-2-yl)benzaldehyde (255 mg) and p-toluenesulfonylmethylisocyanide (198 mg) were used, to thereby yield the title compound (227 mg).

¹H-NMR (400 MHz, DMSO-d₆) δ: 7.38 (1H, dd, J=2.0, 9.5 Hz) 7.58 (1H, dd, J=0.7, 9.5 Hz), 7.74 (1H, s), 7.81 (2H, d, J=8.1 Hz), 8.07 (2H, d, J=8.1 Hz), 8.43 (1H, s), 8.47 (1H, s), 8.89 (1H, t, J=0.7 Hz).
EI-MS m/z: 341 (M+H)⁺.

Example 10

5-[4-(6-Chloroimidazo[1,2-a]pyridin-2-yl)phenyl]-1,3-oxazole (29)

The procedure of Referential Example 1 was repeated, except that 2-amino-5-chloropyridine (49 mg) and 2-bromo-1-[4-(1,3-oxazol-5-yl)phenyl]-1-ethanone (100 mg), which had been produced in Referential Example 10 were used, to thereby yield the title compound (30 mg).
¹H-NMR (400 MHz, DMSO-d₆) δ: 7.32 (1H, d, J=9.5 Hz), 7.65 (1H, d, J=9.5 Hz), 7.75 (1H, s), 7.82 (2H, d, J=8.3 Hz), 8.08 (2H, d, J=8.3 Hz), 8.45 (1H, s), 8.48 (1H, s), 8.84 (1H, s).
EI-MS m/z: 295M⁺.

Example 11

5-[4-(6-Methylimidazo[1,2-a]pyridin-2-yl)phenyl]-1,3-oxazole (30)

The procedure of Referential Example 1 was repeated, except that 2-amino-5-methylpyridine (54 mg) and 2-bromo-1-[4-(1,3-oxazol-5-yl)phenyl]-1-ethanone (133 mg), which had been produced in Referential Example 10, were used, to thereby yield the title compound (60 mg).
¹H-NMR (400 MHz, DMSO-d₆) δ: 2.29 (3H, s), 7.13 (1H, d, J=9.3 Hz), 7.50 (1H, d, J=9.3 Hz), 7.73 (1H, s), 7.79 (2H, d, J=8.3 Hz), 8.06 (2H, d, J=8.1 Hz), 8.33 (1H, s), 8.38 (1H, s), 8.47 (1H, s).
EI-MS m/z: 275 (M)⁺.

Referential Example 15

5-{4-[3-Fluoro-6-(1,1,1-tributylstannyl)imidazo[1,2-a]pyridin-2-yl]phenyl}1,3-oxazole (31)

Under a stream of argon, a solution (30 mL) of 5-[4-(6-bromoimidazo[1,2-a]pyridin-2-yl)phenyl]1,3-oxazole (100 mg), which had been produced in Example 9, in anhydrous tetrahydrofuran was added to a solution (10 mL) of sodium hydride (18 mg) in anhydrous tetrahydrofuran, and the mixture was stirred at room temperature for 30 minutes. A solution (10 mL) of Selectfluor (387 mg) in anhydrous acetonitrile was added to the reaction mixture, and the mixture was stirred at room temperature for 3 hours. Saturated aqueous ammonium chloride solution was added to the reaction mixture, followed by extraction with ethyl acetate. The solvent was evaporated, and the residue was purified through silica gel column chromatography (dichloromethane:methanol=98:2), followed by concentration under reduced pressure, to thereby yield pale yellow solid (100 mg). The procedure of Referential Example 12 was repeated, except that the pale yellow solid (100 mg) was used, to thereby yield the title compound (26 mg).
¹H-NMR (400 MHz, CDCl₃) δ: 0.90-0.92 (9H, m), 1.13-1.15 (6H, m), 1.32-1.39 (6H, m), 1.53-1.61 (6H, m), 7.16 (1H, d, J=8.8 Hz), 7.41 (1H, s), 7.50 (1H, d, J=9.0 Hz), 7.75-7.77 (3H, m), 7.94 (1H, s), 8.09 (1H, d, J=8.5 Hz).
EI-MS m/z: 568 (M)⁺.

Example 12

5-[4-(3-Fluoro-6-iodoimidazo[1,2-a]pyridin-2-yl)phenyl]1,3-oxazole (32)

A solution of iodine in chloroform was added to 5-{4-[3-fluoro-6-(1,1,1-tributylstannyl)imidazo[1,2-a]pyridin-2-yl]phenyl}1,3-oxazole (26 mg) until color-fading was terminated, and the mixture was stirred for 1 hour. Saturated aqueous sodium thiosulfate solution was added to the reaction mixture, followed by extraction with dichloromethane. The solvent was evaporated, and the residue was subjected to NH-silica gel column chromatography. Fractions eluted by dichloromethane-methanol (98:2) were concentrated under reduced pressure, to thereby yield the title compound (16 mg).
¹H-NMR (400 MHz, DMSO-d₆) δ: 7.42 (1H, d, J=9.3 Hz), 7.47 (1H, d, J=9.5 Hz), 7.77 (1H, s), 7.87 (2H, d, J=7.8 Hz), 8.02 (2H, d, J=8.8 Hz), 8.49 (1H, s), 8.67 (1H, s).
EI-MS m/z: 405 (M)⁺.

Referential Example 16

N-(4-Bromophenyl)thiourea (33)

4-Bromophenylisothiocyanate (21.4 g) was dissolved in tetrahydrofuran (50 mL), and concentrated aqueous ammonia (28%) (13.7 mL) was added dropwise to the solution, followed by stirring at room temperature for 10 minutes. The solvent was concentrated under reduced pressure, and the crystals were recovered through filtration by use of water, followed by recrystallization from ethanol, to thereby yield the title compound (16.4 g).
¹H-NMR (400 MHz, DMSO-d₆+D₂O) δ: 7.43 (2H, dt, J=2.4, 8.8 Hz), 7.49 (2H, dt, J=2.4, 8.8 Hz). FAB-MS m/z: 233 (M+H)⁺.

Referential Example 17

2-Amino-6-bromobenzothiazole (34)

A solution of N-(4-bromophenyl)thiourea (16.18 g) and magnesium oxide (1.41 g) in chlorobenzene (100 mL) was heated to 50° C., and a solution of sulfuryl chloride (8.43 mL) in chlorobenzene (9 mL) was added dropwise to the solution over 1 hour or longer, followed by stirring at 50° C. overnight. The reaction mixture was returned to room temperature, and water (20 mL) was added thereto. The pH of the mixture was adjusted to about 8 by use of concentrated aqueous ammonia, and the precipitates were recovered through filtration. The obtained solid was recrystallized from 90% ethanol, to thereby yield the title compound (7.95 g).
¹H-NMR (400 MHz, DMSO-d₆+D₂O) δ: 7.26 (1H, d, J=8.5 Hz) 7.35 (1H, dd, J=2.2, 8.5 Hz), 7.90 (1H, d, J=2.2 Hz).
FAB-MS m/z: 231 (M+H)⁺.

Referential Example 18

2 Amino-5-bromobenzenethiol (35)

Potassium hydroxide (39.6 g) was dissolved at 0° C. in water (80 mL), and 2-amino-6-bromobenzothiazole (6.87 g) was added to the solution, followed by refluxing under heating overnight. The mixture was returned to room temperature, and then neutralized with 5N aqueous acetic acid solution.

The precipitated crystals were recovered through filtration, washed with water, and dried under reduced pressure with heating, followed by recrystallization from isopropyl ether, to thereby yield the title compound (3.87 g).

$^1$H-NMR (400 MHz, DMSO-d$_6$+D$_2$O) δ: 6.72 (1H, d, J=8.8 Hz), 7.00 (1H, d, J=2.4 Hz), 7.24 (1H, dd, J=2.4, 8.8 Hz).

FAB-MS m/z: 204 (M+H)$^+$.

Referential Example 19

Methyl 4-(1,3-oxazol-5-yl)benzoate (36)

The procedure of Example 1 was repeated, except that methyl 4-formylbenzoate (4.92 g) and p-toluenesulfonylmethylisocyanate (7.03 g) were used, to thereby yield the title compound (5.28 g).

$^1$H-NMR (400 MHz, CDCl$_3$) δ: 3.94 (1H, s), 7.47 (1H, s) 7.72 (2H, d, J=8.3 Hz), 7.96 (1H, s), 8.09 (2H, d, J=8.3 Hz).

Referential Example 20

[4-(1,3-Oxazol-5-yl)phenyl]methanol (37)

A solution (2.08 mL) of lithium aluminum hydride (2.4 mole) in tetrahydrofuran was added dropwise under ice cooling to a solution of methyl 4-(1,3-oxazol-5-yl)benzoate (1.02 g) in tetrahydrofuran (20 mL), followed by stirring at 0° C. for 30 minutes. Hydrogen fluoride (840 mg) and water (270 mL) were added to the solution, and the mixture was stirred at room temperature for 1 hour. The reaction mixture was filtered, and the filtrate was concentrated under reduced pressure. The residue was purified through flash column chromatography (n-hexane:ethyl acetate=3:2), followed by concentration under reduced pressure, to thereby yield the title compound (321 mg).

$^1$H-NMR (400 MHz, CDCl$_3$) δ: 1.92 (1H, s), 4.73 (2H, s), 7.34 (1H, s), 7.43 (2H, d, J=8.3 Hz), 7.65 (2H, d, J=8.3 Hz), 7.91 (1H, s).

Referential Example 21

4-(1,3-Oxazol-5-yl)benzaldehyde (38)

Pyridinium chlorochromate (517 mg) and Celite (3 g) were suspended in dichloromethane (20 mL), and a solution of [4-(1,3-oxazol-5-yl)phenyl]methanol (280 mg) in dichloromethane (5 mL) was added to the suspension, followed by stirring at room temperature overnight. The reaction mixture was filtered, and the filtrate was concentrated under reduced pressure. The residue was purified through flash column chromatography (n-hexane:ethyl acetate=2:1), followed by concentration, to thereby yield the title compound (115 mg).

$^1$H-NMR (400 MHz, CDCl$_3$) δ: 7.53 (1H, s), 7.82 (2H, d, J=8.3 Hz), 7.95 (2H, d, J=8.3 Hz), 7.99 (1H, s), 10.03 (1H, s).

Referential Example 22

5-[4-(6-Bromo-1,3-benzothiazol-2-yl)phenyl]-1,3-oxazole (39)

2 Amino-5-bromobenzenethiol (102 mg) and 4-(1,3-oxazol-5-yl)benzaldehyde (87 mg) were dissolved in dimethylsulfoxide (1 mL), followed by stirring at 160° C. for 10 minutes. Water (10 mL) was added to the reaction mixture.

The precipitated matter was recovered through filtration, and washed with methanol, to thereby yield the title compound (105 mg).

$^1$H-NMR (400 MHz, DMSO-d$_6$) δ: 7.71 (1H, dd, J=2.0, 8.5 Hz), 7.88 (1H, s), 7.93 (2H, d, J=8.3 Hz), 8.01 (1H, d, J=8.5 Hz), 8.16 (2H, d, J=8.3 Hz), 8.47 (1H, d, J=2.0 Hz), 8.54 (1H, s).

EI-MS m/z: 356 (M+H)$^+$.

Referential Example 23

5-{4-[6-(1,1,1-Tributylstannyl)-1,3-benzothiazol-2-yl]phenyl}-1,3-oxazole (40)

The procedure of Referential Example 12 was repeated, except that 5-[4-(6-bromo-1,3-benzothiazol-2-yl)phenyl]-1,3-oxazole (71 mg) was used, to thereby yield the title compound (40 mg).

$^1$H-NMR (400 MHz, CDCl$_3$) δ: 0.90 (9H, J=7.3 Hz), 1.11-1.15 (6H, m), 1.35 (6H, q, J=7.3 Hz), 1.54-1.60 (6H, m), 7.46 (1H, s), 7.57 (1H, d, J=8.1 Hz), 7.76 (2H, dd, J=1.5, 8.3 Hz), 7.95 (1H, s), 7.99 (1H, s), 8.04 (1H, d, J=8.1 Hz), 8.15 (2H, d, J=8.3 Hz).

EI-MS m/z: 568 (M)$^+$.

HR-EI-MS m/z: 568.1589 (calcd. for C$_{28}$H$_{36}$N$_2$OSSn; 568.1574).

Example 13

5-[4-(6-Iodo-1,3-benzothiazol-2-yl)phenyl]-1,3-oxazole (41)

The procedure of Example 8 was repeated, except that 5-{4-[6-(1,1,1-tributylstannyl)-1,3-benzothiazol-2-yl]phenyl}-1,3-oxazole (34.0 mg) was used, to thereby yield the title compound (16.6 mg).

$^1$H-NMR (400 MHz, DMSO-d$_6$) δ: 7.85-7.86 (2H, m), 7.89 (1H, s), 7.92 (2H, d, J=8.5 Hz), 8.19 (2H, d, J=8.5 Hz), 8.54 (1H, s), 8.61-8.62 (1H, m).

EI-MS m/z: 404 (M)$^+$.

HR-EI-MS m/z: 403.9500 (calcd. for C$_{16}$H$_9$N$_2$OSI; 403.9480).

Referential Example 24

2-Amino-4-bromobenzenethiol (44)

The procedure of Referential Example 16 was repeated, except that 3-bromophenyl isothiocyanate (25.0 g) serving as a starting material was used, to thereby yield N-(3-bromophenyl)thiourea (19.4 g) as colorless crystals. Subsequently, The procedure of Referential Example 17 was repeated, to thereby yield 2-amino-5-bromobenzothiazole (1.21 g). Thereafter, The procedure of Referential Example 18 was repeated, to thereby yield the title compound (227 mg).

$^1$H-NMR (400 MHz, CD$_3$OD) δ: 6.67 (1H, d, J=7.8 Hz), 6.75 (1H, d, J=7.8 Hz), 6.95 (1H, d, J=7.8 Hz).

Example 14

5-[4-(5-Iodo-1,3-benzothiazol-2-yl)phenyl]-1,3-oxazole (47)

The procedure of Referential Example 22 was repeated, except that 2-amino-4-bromobenzenethiol (143 mg), which had been produced in Referential Example 24, and 4-(1,3-oxazol-5-yl)benzaldehyde (121 mg), which had been produced in Referential Example 21, were used, to thereby yield 5-[4-(5-bromo-1,3-benzothiazol-2-yl)phenyl]-1,3-oxazole (156 mg). Subsequently, the procedure of Referential Example 12 was repeated, to thereby yield 5-{4-[5-(1,1,1-tributylstannyl)-1,3-benzothiazol-2-yl]phenyl}-1,3-oxazole (94 mg). Thereafter, The procedure of Example 8 was repeated, to thereby yield the title compound (33.4 mg).

$^1$H-NMR (400 MHz, DMSO-d$_6$) δ: 7.35 (1H, t, J=7.8 Hz), 7.83 (1H, d, J=7.8 Hz), 7.90 (1H, s), 7.93 (2H, d, J=8.3 Hz), 8.09 (1H, d, J=7.8 Hz), 8.22 (2H, d, J=8.3 Hz), 8.54 (1H, s).

EI-MS m/z: 404 (M)$^+$.

HR-EI-MS m/z: 403.9500 (calcd. for C$_{16}$H$_9$N$_2$OSI; 403.9480).

Referential Example 25

5-(2-Bromo-4-methylphenyl)-1,3-oxazole (50)

1-Hydroxybenzotriazole (3.78 g), 4-dimethylaminopyridine (3.42 g), and N-ethyl-N'-(3-dimethylaminopropyl)carbodiimide hydrochloride (5.40 g) were added to a solution (100 mL) of 2-bromo-4-methylbenzoic acid (5.00 g) and N,O-dimethylhydroxylamine hydrochloride (2.73 g) in dichloromethane, followed by stirring at room temperature for 13 hours. 1N Hydrochloric acid was added to the reaction mixture, followed by extraction with dichloromethane and evaporation of the solvent. After purification, 2-bromo-4,N-dimethyl-N-methoxybenzamide (6.0 g) was yielded. The 2-bromo-4,N-dimethyl-N-methoxybenzamide (6.0 g) was dissolved in an anhydrous tetrahydrofuran solution (50 mL) under a stream of argon. Diisobutylaluminum hydride (24.7 mL, 0.93M hexane solution) was added dropwise to the solution at −78° C., and the mixture was stirred at the same temperature for 2 hours. Methanol (5 mL) was added dropwise to the reaction mixture, and an aqueous saturated ammonium chloride solution (5 mL) was added thereto, the mixture was stirred at room temperature for 1 hour. Sodium sulfate anhydrate was added to the reaction mixture, followed by further stirring for 1 hour. The precipitated matter was removed through filtration by use of Celite, and the filtrate was purified, to thereby yield 2-bromo-4-methylbenzaldehyde (4.0 g). The procedure of Referential Example 9 was repeated, except that 2-bromo-4-methylbenzaldehyde (4.0 g) was used, to thereby yield the title compound (3.7 g).

$^1$H-NMR (400 MHz, CDCl$_3$) δ: 2.37 (3H, s), 7.20 (1H, d, J=8.1 Hz), 7.51 (1H, s), 7.63 (1H, d, J=8.1 Hz), 7.78 (1H, s), 7.94 (1H, s).

EI-MS m/z: 238 (M)$^+$.

Referential Example 26

3-Bromo-4-(1,3-oxazol-5-yl)benzaldehyde (54)

N-Bromosuccinimide (2.36 g) and 2,2'-azobis(2-methylpropionitrile) (164 mg) were added to a solution (100 mL) of 5-(2-bromo-4-methylphenyl)-1,3-oxazole (2.6 g) in carbon tetrachloride, and the mixture was refluxed under heating for 2.5 hours. Insoluble matter was removed through filtration, followed by purification, to thereby yield 5-[2-bromo-4-(bromomethyl)phenyl]-1,3-oxazole (3.2 g). Acetic acid (190 mg) and sodium hydrogencarbonate (336 mg) were added to a solution (50 mL) of the thus-obtained 5-[2-bromo-4-(bromomethyl)phenyl]-1,3-oxazole (500 mg) in anhydrous N,N-dimethylformamide, and the mixture was stirred at room temperature for 23 hours. The solvent was evaporated, and the residue was purified, to thereby yield 3-bromo-4-(1,3-oxazol-5-yl)benzyl acetate (300 mg). This procedure was repeated.

2N Aqueous sodium hydroxide solution (5 mL) was added to a solution (50 mL) of the thus-obtained 3-bromo-4-(1,3-oxazol-5-yl)benzyl acetate (490 mg) in methanol, and the mixture was stirred at room temperature for 30 minutes. The solvent was evaporated, and the residue was purified, to thereby yield [3-bromo-4-(1,3-oxazol-5-yl)phenyl]methanol (350 mg). Manganese dioxide (672 mg) was added to a solution (50 mL) of the thus-obtained [3-bromo-4-(1,3-oxazol-5-yl)phenyl]methanol (350 mg) in chloroform, and the mixture was refluxed under heating for 20 hours. Insoluble matter was removed through filtration by use of Celite, and the filtrate was concentrated under reduced pressure. The residue was purified through silica gel column chromatography (dichloromethane), followed by concentration, to thereby yield the title compound (300 mg).

$^1$H-NMR (400 MHz, CDCl$_3$) δ: 7.90 (1H, d, J=8.1 Hz), 7.97 (1H, d, J=8.1 Hz), 8.04 (1H, s), 8.10 (1H, s), 8.18 (1H, s), 9.99 (1H, s).

EI-MS m/z: 252 (M)$^+$.

Example 15

2-[3-Iodo-4-(1,3-oxazol-5-yl)phenyl]-1,3-benzothiazol-6-ol (59)

2-Amino-6-methoxybenzothiazole (3.0 g) was added to a solution (100 mL) of potassium hydroxide (21.9 g) in water, followed by refluxing under heating for 15 hours. The mixture was neutralized with 5N aqueous acetic acid solution, and the precipitated crystals were recovered through filtration. The procedure of Referential Example 22 was repeated, except that the thus-recovered 2-amino-5-methoxy-1-benzenethiol (185 mg) and 3-bromo-4-(1,3-oxazol-5-yl)benzaldehyde (300 mg), which had been produced in Referential Example 26, were used, to thereby yield 5-[2-bromo-4-(6-methoxy-1,3-benzothiazol-2-yl)phenyl]-1,3-oxazole (450 mg). Subsequently, The procedure of Referential Example 12 was repeated, except that 5-[2-bromo-4-(6-methoxy-1,3-benzothiazol-2-yl)phenyl]-1,3-oxazole (450 mg) was used, to thereby yield 5-[4-(6-methoxy-1,3-benzothiazol-2-yl)-2-(1,1,1-tributylstannyl)phenyl]-1,3-oxazole (15 mg). Thereafter, the procedure of Example 12 was repeated, except that 5-[4-(6-methoxy-1,3-benzothiazol-2-yl)-2-(1,1,1-tributylstannyl)phenyl]-1,3-oxazole (15 mg) was used, to thereby yield 5-[2-iodo-4-(6-methoxy-1,3-benzothiazol-2-yl)phenyl]-1,3-oxazole. Under a stream of argon, boron tribromide (200 µL, 1M dichloromethane solution) was added dropwise to a solution (30 mL) of 5-[2-iodo-4-(6-methoxy-1,3-benzothiazol-2-yl)phenyl]-1,3-oxazole (20 mg) in dichloromethane, and the mixture was stirred at room temperature for 23 hours. 1N Aqueous hydrochloric acid solution was added to the reaction mixture, followed by extraction with ethyl acetate. The solvent was evaporated, and the residue was purified through silica gel column chromatography (n-hexane:ethyl acetate=1:1), to thereby yield the title compound (10 mg).

$^1$H-NMR (400 MHz, DMSO-d$_6$) δ: 7.03 (1H, dd, J=2.4 Hz, 8.8 Hz), 7.45 (1H, d, J=2.4 Hz), 7.78 (1H, d, J=8.1 Hz), 7.90 (2H, m), 8.09 (1H, dd, J=1.7 Hz, 8.1 Hz), 8.61 (1H, s), 8.62 (1H, d, J=1.7 Hz), 9.99 (1H, s).

EI-MS m/z: 420 (M)$^+$.

Example 16

6-Iodo-2-[4-(1H-3-pyrazolyl)phenyl]-1,3-benzothiazole (65)

2-Amino-6-bromobenzothiazole (1.75 g) was added to a solution (50 mL) of potassium hydroxide (10.1 g) in water, followed by refluxing under heating for 21 hours. The mixture was neutralized with 5N aqueous acetic acid solution, and the precipitated matter was recovered through filtration. The thus-recovered crude crystals were recrystallized from a mixture of ethyl acetate and hexane, to thereby yield 2-amino-5-bromo-1-benzenethiol (204 mg) (1.1 g). Subsequently, a solution (2 mL) of 2-amino-5-bromo-1-benzenethiol (204 mg) and 4-acetylbenzaldehyde (148 mg) in dimethylsulfoxide was stirred at 150° C. for 30 minutes under heating. The reaction mixture was extracted with ethyl acetate. The solvent was evaporated, and the residue was purified, to thereby yield 1-[4-(6-bromo-1,3-benzothiazol-2-yl)phenyl]-1-ethanone (70 mg). Thereafter, the procedure of Referential Example 6 was repeated, except that 1-[4-(6-bromo-1,3-benzothiazol-2-yl)phenyl]-1-ethanone was used, to thereby yield (E)-1-[4-(6-bromo-1,3-benzothiazol-2-yl)phenyl]-3-(dimethylamino)-2-propen-1-one (120 mg). The procedure of Example 3 was repeated, except that the thus-obtained (E)-1-[4-(6-bromo-1,3-benzothiazol-2-yl)phenyl]-3-(dimethylamino)-2-propen-1-one (120 mg) was used, to thereby yield 6-bromo-2-[4-(1H-3-pyrazolyl)phenyl]-1,3-benzothiazole (100 mg). The procedure of Referential Example 12 was repeated, except that the thus-obtained 6-bromo-2-[4-(1H-3-pyrazolyl)phenyl]-1,3-benzothiazole (100 mg) was used, to thereby yield 2-[4-(1H-3-pyrazolyl)phenyl]-6-(1,1,1-tributylstannyl)-1,3-benzothiazole (24 mg). The procedure of Example 12 was repeated, except that the thus-obtained 2-[4-(1H-3-pyrazolyl)phenyl]-6-(1,1,1-tributylstannyl)-1,3-benzothiazole (24 mg) was used, to thereby yield the title compound (11 mg).

$^1$H-NMR (400 MHz, DMSO-d$_6$) δ: 6.85 (1H, s), 7.84 (3H, br), 8.02 (2H, d, J=8.1 Hz), 8.12 (2H, d, J=8.1 Hz), 8.60 (1H, s), 13.06 (1H, s).

EI-MS m/z: 403 (M)$^+$.

Referential Example 27

5-(1,3-Oxazol-5-yl)-2-pyridinecarbaldehyde (71)

The procedure of Referential Example 2 was repeated, except that 5-cyano-2-methylpyridine (500 mg) was used, to thereby yield 6-methylnicotinaldehyde (360 mg). The procedures of Referential Examples 25 and 26 were repeated, except that the thus-obtained 6-methylnicotinaldehyde (360 mg) was used, to thereby yield the title compound (140 mg).

$^1$H-NMR (400 MHz, CDCl$_3$) δ: 7.62 (1H, s), 8.03-8.05 (2H, m), 8.11 (1H, d, J=8.1 Hz), 9.09 (1H, s), 10.09 (1H, s).

EI-MS m/z: 174 (M)$^+$.

Example 17

5-[6-(6-Iodo-1,3-benzothiazol-2-yl)-3-pyridyl]-1,3-oxazole (74)

The procedure of Example 14 was repeated, except that 5-(1,3-oxazol-5-yl)-2-pyridinecarbaldehyde (140 mg), which had been produced in Referential Example 27, and 2-amino-5-bromo-1-benzenethiol (163 mg) were used, to thereby yield the title compound (25 mg).

$^1$H-NMR (400 MHz, DMSO-d$_6$) δ: 7.86-7.91 (2H, m), 8.01 (1H, s), 8.34 (1H, d, J=8.1 Hz), 8.41 (1H, d, J=8.3 Hz), 8.62-8.63 (2H, m), 9.12 (1H, s).

EI-MS m/z: 405 (M)$^+$.

Example 18

6-Iodo-2-[4-(1,3-oxazol-5-yl)phenyl]-1,3-benzoxazole (78)

4-(1,3-Oxazol-5-yl)benzaldehyde (346 mg), which had been produced in Referential Example 21, and 2-amino-5-nitrophenol (308 mg) were dissolved in ethanol (20 mL), followed by refluxing under heating overnight. The solution was returned to room temperature, and the precipitated matter was recovered through filtration, to thereby yield 5-nitro-2-({(E)-1-[4-(1,3-oxazol-2-yl)phenyl]methylidene}amino)phenol (308 mg). Subsequently, this product was dissolved in dimethylsulfoxide (4 mL), and iodobenzene diacetate (258 mg) was added to the solution, followed by stirring at room temperature for 30 minutes. Water (40 mL) was added to the reaction mixture, and the precipitated matter was recovered through filtration, dried, and purified, to thereby yield 6-nitro-2-[4-(1,3-oxazol-5-yl)phenyl]-1,3-benzoxazole (114 mg). Thereafter, this product was dissolved in tetrahydrofuran/ethyl acetate (1:1) (20 mL), and 10% palladium carbon (50 mg) was added to the solution, followed by stirring under hydrogen at room temperature overnight. After filtration through Celite, the filtrate was concentrated, and the solid was recovered through filtration by use of diethyl ether, to thereby yield 2-[4-(1,3-oxazol-5-yl)phenyl]-1,3-benzoxazole-6-amine (89 mg). The thus-obtained 2-[4-(1,3-oxazol-5-yl)phenyl]-1,3-benzoxazole-6-amine (111 mg) was dissolved in a mixture of acetic acid (2 mL) and 3N hydrochloric acid (1 mL), and, under ice cooling, a solution of sodium nitrite (33 mg) in water was added dropwise to the solution, followed by stirring for 5 minutes. Under ice cooling, a solution of potassium iodide (80 mg) in water was added dropwise to the reaction mixture, followed by stirring for 30 minutes. The reaction mixture was alkalified with potassium hydroxide, and sodium thiosulfate was added thereto for decoloring, followed by recovering the precipitated solid through filtration. The thus-recovered solid was washed and dried, to thereby yield the title compound (51 mg).

$^1$H-NMR (400 MHz, DMSO-d$_6$) δ: 7.72 (1H, dd, J=2.0, 8.8 Hz), 7.92 (1H, s), 7.96 (1H, d, J=8.8 Hz), 8.00 (2H, d, J=8.3 Hz), 8.14 (1H, d, J=2.0 Hz), 8.31 (2H, d, J=8.3 Hz), 8.56 (1H, s).

EI-MS m/z: 388 (M)$^+$.

HR-EI-MS m/z: 387.9736 (calcd. for C$_{16}$H$_9$IN$_2$O$_2$; 387.9709).

Example 19

N1-{2-[4-(1,3-oxazol-5-yl)phenyl]imidazo[1,2-a]pyridin-6-yl}-2-fluoroacetamide (82)

2-Bromo-1-[4-(1,3-oxazol-5-yl)phenyl]-1-ethanone (1.064 g), which had been produced in Referential Example 10, and 2-amino-5-nitropyridine (0.556 g) were dissolved in ethanol (20 mL), and the solution was refluxed under heating overnight. Triethylamine (0.836 mL) was added to the reaction mixture, followed by further refluxing under heating for 1 hour. After the mixture had been left to cool, water (5 mL) was added thereto, and the precipitated matter was recovered through filtration, to thereby yield 5-[4-(6-nitroimidazo[1,2-a]pyridin-2-yl)phenyl]-1,3-oxazole (0.743 g). Subsequently, this product was suspended in methanol/ethyl:acetate (1:1) (200 mL), and 10% palladium carbon (200 mg) was added to the suspension, followed by stirring under hydrogen at room temperature overnight. After filtration through Celite, and the filtrate was concentrated and dried, to thereby yield 2-[4-(1, 3-oxazol-5-yl)phenyl]imidazo[1,2-a]pyridine-6-amine (426 mg). Thereafter, this product was suspended in dichloromethane (50 mL), and diisopropylethylamine (523 µL) and chloroacetyl chloride (120 µL) were added to the suspension, followed by stirring at room temperature overnight. The reaction mixture was concentrated, and the residue was purified, to thereby yield N1-{2-[4-(1,3-oxazol-5-yl)phenyl]imidazo[1,2-a]pyridin-6-yl}-2-chloroacetamide (76 mg). The thus-obtained N1-{2-[4-(1,3-oxazol-5-yl)phenyl]imidazo[1,2-a]pyridin-6-yl}-2-chloroacetamide (35 mg) was dissolved in dimethylsulfoxide (0.5 mL), and tetrabutylammonium fluoride (1M tetrahydrofuran solution, 1.0 mL) was added to the solution, followed by stirring at 90° C. for 1 hour. After the reaction mixture had been left to cool, water was added thereto, and the precipitated gray solid was recovered through filtration. The thus-obtained solid was purified through column chromatography (dichloromethane:methanol=15:1), to thereby yield the title compound (10 mg).

$^1$H-NMR (400 MHz, DMSO-$d_6$) δ: 5.06 (2H, d, J=46.6 Hz), 7.35-7.38 (1H, m) 7.60 (1H, d, J=10.3 Hz), 7.74 (1H, s), 7.80 (2H, d, J=8.3 Hz), 8.04 (2H, d, J=8.3 Hz), 8.47 (1H, s), 8.58 (1H, s), 9.21 (1H, s), 10.31 (1H, s).

EI-MS m/z: 336 (M)$^+$.

HR-EI-MS m/z: 336.1023 (calcd. for $C_{18}H_{13}FN_4O_2$; 336.1023).

Example 20

5-{4-[6-(Fluoromethyl)imidazo[1,2-a]pyridin-2-yl] phenyl}-1,3-oxazole (86)

6-Aminonicotinic acid (830 mg) was dissolved in tetrahydrofuran (20 mL), and borane-tetrahydrofuran complex (12 mL) was added to the solution, followed by refluxing under nitrogen for 4 hours. Subsequently, 2.4N hydrochloric acid solution (10 mL) and methanol (10 mL) were gradually added to the mixture, followed by heating at 80° C. for 1 hour. After the mixture had been left to cool, the mixture was alkalified with 2N sodium hydroxide solution and extracted with dichloromethane-methanol, followed by purification, to thereby yield (6-amino-3-pyridyl)methanol (562 mg). Thereafter, this product was dissolved in ethanol (35 mL), and 2-bromo-1-[4-(1,3-oxazol-5-yl)phenyl]-1-ethanone (857 mg), which had been produced in Referential Example 10, was added to the solution. Subsequently, sodium hydrogencarbonate (271 mg) was further added to the mixture, followed by refluxing for 14 hours. Water (10 mL) was added to the reaction mixture, and the mixture was left to cool, followed by recovering the precipitated matter through filtration and then drying, to thereby yield {2-[4-(1,3-oxazol-5-yl)phenyl]imidazo[1,2-a]pyridin-6-yl}methanol (664 mg). Thereafter, 47% hydrobromic acid (6 mL) and concentrated sulfuric acid (600 µL) were added to {2-[4-(1,3-oxazol-5-yl)phenyl]imidazo[1,2-a]pyridin-6-yl}methanol (170 mg), and the mixture was refluxed for 4 hours. After the mixture had been left to cool, the mixture was alkalified with 2N sodium hydroxide solution, and extracted with dichloromethane-methanol, followed by drying over sodium sulfate. The solvent was evaporated, and the residue was purified through silica gel chromatography (dichloromethane:methanol=95:5), followed by concentration under reduced pressure, to thereby yield 5-{4-[6-(bromomethyl)imidazo[1,2-a]pyridin-2-yl]phenyl}-1,3-oxazole (169 mg). The thus-obtained 5-{4-[6-(bromomethyl)imidazo[1,2-a]pyridin-2-yl]phenyl}-1,3-oxazole (71 mg) was dissolved in dimethylsulfoxide (1.0 mL), and tetrabutylammonium fluoride (1M tetrahydrofuran solution, 2.0 mL) was added to the solution. The procedure of Example 19 was repeated, to thereby yield the title compound (15 mg).

$^1$H-NMR (400 MHz, DMSO-$d_6$) δ: 5.46 (2H, d, J=47.8 Hz), 7.34 (1H, d, J=23.9 Hz), 7.64 (1H, d, J=9.3 Hz), 7.75 (1H, s), 7.81 (2H, d, J=8.3 Hz), 8.09 (2H, d, J=8.3 Hz), 8.48 (1H, s), 8.53 (1H, s), 8.71 (1H, d, J=3.4 Hz).

EI-MS m/z: 293 (M)$^+$.

Example 21

5-[4-(6-Fluoroimidazo[1,2-a]pyridin-2-yl)phenyl]-1, 3-oxazole (87)

2-Amino-5-fluoropyridine (112 mg) and 2-bromo-1-[4-(1, 3-oxazol-5-yl)phenyl]-1-ethanone (266 mg), which had been produced in Referential Example 10, were dissolve in ethanol (30 mL), and sodium hydrogencarbonate (84 mg) was added to the solution, followed by refluxing for 16 hours. Water (10 mL) was added to the reaction mixture. After the reaction mixture had been left to cool, the precipitated matter was recovered through filtration and dried, to thereby yield the title compound (90 mg).

$^1$H-NMR (400 MHz, DMSO-$d_6$) δ: 7.35 (1H, ddd, J=2.4 Hz, 8.5 Hz, 10.0 Hz), 7.66 (1H, dd, J=5.1 Hz, 10.0 Hz), 7.74 (1H, s), 7.81 (2H, d, J=8.3 Hz), 8.07 (2H, d, J=8.3 Hz), 8.47 (2H, s), 8.77 (1H, dd, J=2.4 Hz, 4.9 Hz).

EI-MS m/z: 279 (M)$^+$.

Referential Example 28

1-[4-(6-Fluoroimidazo[1,2-a]pyridin-2-yl)phenyl]-1-ethanone (91)

2-Amino-5-fluoropyridine (2.5 g) and 2-bromo-4'-cyanoacetophenone (5.0 g) were dissolved in ethanol (100 mL), and sodium hydrogencarbonate (1.9 g) was added to the solution, followed by refluxing for 16 hours. Water (10 mL) was added to the reaction mixture. After the reaction mixture had been left to cool, the precipitated matter was recovered through filtration and dried, to thereby yield 4-(6-fluoroimidazo[1,2-a]pyridin-2-yl)benzonitrile (2.1 g). Subsequently, the thus-obtained 4-(6-fluoroimidazo[1,2-a]pyridin-2-yl)benzonitrile was dissolved in anhydrous tetrahydrofuran solution (30 mL), and diisobutylaluminum hydride (9.0 mL, 0.93M hexane solution) was added dropwise to the solution at −78° C., followed by stirring under a stream of argon at room temperature for 2 hours. Saturated aqueous ammonium chloride solution (10 mL) was added dropwise to the reaction mixture, and the mixture was stirred at room temperature for 1 hour. Anhydrous magnesium sulfate and diethyl ether were added to the resultant mixture, followed by further stirring for 1 hour. The solvent was evaporated, and the residue was purified, to thereby yield 4-(6-fluoroimidazo[1,2-a]pyridin-2-yl)benzaldehyde (0.6 g). Subsequently, this product was dissolved in anhydrous tetrahydrofuran solution (30 mL), and methyl magnesium bromide (0.78 mL, 3M hexane solution) was added dropwise to the mixture under a stream of argon at −78° C., followed by stirring under ice cooling for 15 minutes and then at room temperature for 3 hours. Saturated aqueous ammonium chloride solution (10 mL) was added dropwise to the reaction mixture, followed by stirring at room temperature for 1 hour. The mixture was extracted with dichloromethane-methanol, and purified through silica gel chromatography (dichloromethane:methanol=95:5), to thereby yield 1-[4-(6-fluoroimidazo[1,2-a]pyridin-2-yl)phenyl]-1-ethanol (530 mg). The thus-obtained 1-[4-(6-fluoroimidazo[1,2-a]

pyridin-2-yl)phenyl]-1-ethanol (530 mg) was dissolved in chloroform solution (50 mL), and manganese dioxide (721 mg) was added to the solution, followed by refluxing for 4 hours. After the reaction mixture had been filtered through Celite, the filtrate was concentrated, and the residue was purified through silica gel chromatography (dichloromethane:methanol=98:2), to thereby yield the title compound (410 mg).

$^1$H-NMR (400 MHz, DMSO-$d_6$) δ: 2.60 (3H, d, J=0.6 Hz), 7.34-7.39 (1H, m), 7.67 (1H, dd, J=5.4 Hz, 10.0 Hz), 8.02 (2H, d, J=8.3 Hz), 8.09 (2H, d, J=8.1 Hz), 8.53 (1H, s), 8.77 (1H, dd, J=2.4 Hz, 4.6 Hz).

EI-MS m/z: 254 (M)$^+$.

Example 22

6-Fluoro-2-[4-(1H-3-pyrazolyl)phenyl]imidazo[1,2-a]pyridine (93)

The procedure of Referential Example 6 was repeated, except that 1-[4-(6 fluoroimidazo[1,2-a]pyridin-2-yl)phenyl]-1-ethanone (410 mg), which had been produced in Referential Example 28 was used, to thereby yield (E)-3-(dimethylamino)-1-[4-(6-fluoroimidazo[1,2-a]pyridin-2-yl)phenyl]-2-propen-1-one (120 mg). Subsequently, The procedure of Referential Example 3 was repeated, to thereby yield the title compound (75 mg).

$^1$H-NMR (400 MHz, DMSO-$d_6$) δ: 6.74 (1H, d, J=2.0 Hz), 7.30-7.35 (1H, m), 7.64 (1H, dd, J=4.4 Hz, 10.0 Hz), 7.71 (1H, br), 7.86 (2H, d, J=8.3 Hz), 7.98 (2H, d, J=8.3 Hz), 8.41 (1H, s), 8.75 (1H, dd, J=2.4 Hz, 4.6 Hz), 12.94 (1H, br).

EI-MS m/z: 278 (M)$^+$.

Example 23

[$^{125}$I]5-[4-(6-Iodoimidazo[1,2-a]pyridin-2-yl)phenyl]-1,3-oxazole

The compound was prepared through iodo-destannylation with 5-{4-[6-(1,1,1-tributylstannyl)imidazo[1,2-a]pyridin-2-yl]phenyl}-1,3-oxazole (tributylstannyl precursor).

Specifically, to a mixture of a 1.0 mg/mL solution (20 μL) of tributylstannyl precursor in ethanol, 0.3M sodium phosphate buffer (pH 5.5) (70 μL), and a [$^{125}$I]sodium iodide solution (1 to 10 mCi) (10 to 30 μL), 0.10 mg/mL aqueous p-toluenesulfonechloroamide sodium solution (20 μL) was added. After the mixture had been allowed to stand at room temperature for two minutes, 2.0 mg/mL aqueous sodium disulfite solution (100 μL) was added to thereby terminate reaction. The reaction mixture was separated and purified by means of a reverse phase column (SHISEIDO CAPCELLPAK C18 UG120, 6.0×150 mm) with a mobile phase of 60% aqueous methanol solution at a flow rate of 1.0 mL/min. Ethanol and 50 mM aqueous ascorbic acid solution were added in appropriate amounts to the purified product such that a 5.0 mM ascorbic acid/90% aqueous ethanol solution (about 1 to 2 mCi/mL) was finally produced, followed by filtration through a 0.20-μm membrane filter, to thereby prepare a target solution. This solution was stored at −20° C. until eight weeks in order to be employed in the subsequent in vitro binding experiments and determination of distribution in rats. When TLC analysis was performed by means of a reverse phase silica gel plate (Whatman, KC18F) with a 95% aqueous methanol solution as a developer, the target compound was found to have an Rf of about 0.5, a radiochemical purity of 95% or higher, and a relative radioactivity of about 2,000 Ci/mM.

Referential Example 29

[$^{123}$I]5-[4-(6-Iodoimidazo[1,2-a]pyridin-2-yl)phenyl]-1,3-oxazole

The compound was prepared through deiodostannylation with 5-{4-[6-(1,1,1-tributylstannyl)imidazo[1,2-a]pyridin-2-yl]phenyl}-1,3-oxazole (tributylstannyl precursor).

Specifically, to a mixture of a 1.0 mg/mL solution (20 μL) of tributylstannyl precursor in ethanol, 0.3M sodium phosphate buffer (pH 5.5) (70 μL), and a [$^{123}$I]sodium iodide solution (about 40 mCi) (30 μL), 10% sodium hypochlorite solution (20 μL) was added. After the mixture had been allowed to stand at room temperature for 10 minutes, 20 mg/mL aqueous sodium thiosulfate (pentahydrate) solution (100 μL) was added to thereby terminate reaction. The reaction product was separated and purified by means of a reverse phase column (SHISEIDO CAPCELLPAK C18 UG120, 6.0×150 mm) with a mobile phase of 60% aqueous methanol solution at a flow rate of 1.0 mL/min. Ethanol and 0.25 mM aqueous ascorbic acid/0.1% Tween 80 in physiological saline were added in appropriate amounts to the purified product such that an aqueous 5% ethanol/0.25 mM ascorbic acid/0.1% Tween 80 in physiological saline (about 2 to 3 mCi/mL) was finally produced. The solution was filtered through a 0.20-μm membrane filter, to thereby prepare a target solution (for imaging of monkeys). When TLC analysis was performed by means of a reverse phase silica gel plate (Whatman, KC18F) with a 95% aqueous methanol solution as a developer, the target compound was found to have an Rf of about 0.5 and a radiochemical purity of 90% or higher immediately after preparation and three hours after preparation (room temperature).

Example 24

[$^{125}$I]6-Iodo-2-[4-(1H-3-pyrazolyl)phenyl]imidazo[1,2-a]pyridine

The procedure of Example 23 was repeated, except that 2-[4-(1H-3-pyrazolyl)phenyl]-6-(1,1,1-tributylstannyl)imidazo[1,2-a]pyridine (tributylstannyl precursor) was used. Ethanol and 50 mM aqueous ascorbic acid solution were added in appropriate amounts to the purified product such that a 5.0 mM ascorbic acid/90% aqueous ethanol solution (about 1 to 2 mCi/mL) was finally produced, followed by filtration through a 0.20-μm membrane filter, to thereby prepare a target solution. This solution was stored at −20° C. for eight weeks in order to be employed in the subsequent in vitro binding experiments and determination of distribution in rats. When TLC analysis was performed by means of a reverse phase silica gel plate (Whatman, KC18F) with a 90% aqueous methanol solution as a developer, the target Rf was about 0.5, radiochemical purity of 95% or higher, and relative radioactivity of about 2,000 Ci/mM.

Referential Example 30

[$^{123}$I]6-Iodo-2-[4-(1H-3-pyrazolyl)phenyl]imidazo[1,2-a]pyridine

The procedure of Referential Example 29 was repeated, except that 2-[4-(1H-3-pyrazolyl)phenyl]-6-(1,1,1-tributylstannyl)imidazo[1,2-a]pyridine (tributylstannyl precursor) was used. Ethanol and 40 mM aqueous ascorbic acid/0.05% Tween 80 in physiological saline were added in appropriate amounts to the purified product such that an aqueous 5% ethano/40 mM ascorbic acid/0.05% Tween 80 in physiological saline (about 2 to 3 mCi/mL) was finally produced. The solution was filtered through a 0.20-μm membrane filter, to thereby prepare a target solution (for imaging of monkeys). When TLC analysis was performed by means of a reverse phase silica gel plate (Whatman, KC18F) with a 90% aqueous methanol solution as a developer, the target compound was found to have an Rf about 0.5 and a radiochemical purity of 90% or higher immediately after preparation and three hours after preparation (room temperature).

Example 25 tert-Butyl 3-{4-[6-(1,1,1-tributylstannyl)imidazo[1,2-a]pyridin-2-yl]phenyl}-1H-1-pyrazolecarboxylate 2-[4-(1H-3-Pyrazolyl)phenyl]-6-(1,1,1-tributylstannyl)imidazo[1,2-a]pyridine (113 mg) and dimethylaminopyridine (26 mg) were dissolved in dichloromethane (3 mL), followed by stirring under ice cooling. Di-tert-butyl dicarbonate (1.1 mL) was added to the reaction mixture, followed by stirring at room temperature for 8 hours. Dichloromethane was added to the reaction mixture, and the mixture was washed sequentially with water and saturated saline, followed by drying over sodium sulfate anhydrate. The solvent was evaporated, and the residue was subjected to silica gel chromatography. Fractions eluted by dichloromethane-methanol (97:3) were concentrated under reduced pressure, to thereby yield the title compound (127 mg).

$^1$H-NMR (400 MHz, CDCl$_3$) δ: 0.91 (9H, t, J=7.3 Hz), 1.06-1.26 (6H, m), 1.31-1.40 (6H, m), 1.47-1.61 (6H, m), 1.68 (9H, s), 6.76 (1H, d, J=2.9 Hz), 7.16 (1H, d, J=8.8 Hz), 7.61 (1H, d, J=8.5 Hz), 7.89 (1H, s), 7.98-8.04 (5H, m), 8.11 (1H, d, J=3.0 Hz).

FAB-MS m/z: 651 (M+H)$^+$.

Example 26

2-[4-(6-Iodoimidazo[1,2-a]pyridin-2-yl)phenyl]-4,5-dihydro-1,3-oxazole

4-Cyanobenzoyl chloride (1.66 g) was dissolved in dichloromethane (30 mL), followed by stirring under ice cooling. A solution of 2-aminoethanol (2.4 mL) in dichloromethane (10 mL) was gradually added dropwise to the reaction mixture, followed by stirring under ice cooling for 30 minutes. After completion of reaction, the solvent was evaporated, and the residue was subjected to silica gel chromatography. Fractions eluted by dichloromethane-methanol (9:1) were concentrated under reduced pressure, to thereby yield N1-(2-hydroxyethyl)-4-cyanobenzamide (1.91 g).

$^1$H-NMR (400 MHz, CDCl$_3$) δ: 3.66 (2H, q, J=5.1 Hz), 3.87 (2H, Br), 6.62 (1H, Br), 7.75 (2H, d, J=8.1 Hz), 7.89 (2H, d, J=8.1 Hz).

Subsequently, N1-(2-hydroxyethyl)-4-cyanobenzamide (1.91 g) was dissolved in dichloromethane (30 mL), followed by stirring under ice cooling. Thionyl chloride (3.3 mL) was gradually added to the reaction mixture, and the mixture was stirred at room temperature for 13 hours. After completion of reaction, the solvent was evaporated, and the residue was subjected to silica gel chromatography. Fractions eluted by dichloromethane-methanol (98:2) were concentrated under reduced pressure, to thereby yield N1-(2-chloroethyl)-4-cyanobenzamide (2.07 g).

$^1$H-NMR (400 MHz, CDCl$_3$) δ: 3.76 (2H, t, J=5.4 Hz), 3.84 (2H, q, J=4.2 Hz), 7.76 (2H, d, J=8.1 Hz), 7.90 (2H, d, J=8.1 Hz).

Subsequently, a solution of N1-(2-chloroethyl)-4-cyanobenzamide (2.0 g) in tetrahydrofuran (20 mL) was added to a solution of 60% sodium hydride (400 mg) in tetrahydrofuran (15 mL), followed by stirring at 50° C. for 1 hour with heating. After addition of methanol (1 mL) to the mixture for terminating reaction, the solvent was evaporated, and the residue was dissolved in dichloromethane. The solution was washed sequentially with saturated ammonium chloride solution, saturated sodium bicarbonate solution, and saturated saline, followed by drying over sodium sulfate anhydrate. After concentration under reduced pressure, the residue was subjected to silica gel chromatography. Fractions eluted by dichloromethane-ethyl acetate (1:1) were concentrated under reduced pressure, to thereby yield 4-(4,5-dihydro-1,3-oxazol-2-yl)benzonitrile (1.55 g).

$^1$H-NMR (400 MHz, CDCl$_3$) δ: 4.11 (2H, t, J=9.5 Hz), 4.48 (2H, t, J=9.5 Hz), 7.71 (2H, d, J=8.3 Hz), 8.05 (2H, d, J=8.3 Hz).

FAB-MS m/z: 173 (M+H)$^+$.

Subsequently, 4-(4,5-dihydro-1,3-oxazol-2-yl)benzonitrile (2.24 g) was added to tetrahydrofuran (22 mL), followed by stirring under ice cooling. Diisobutylaluminum hydride (30 mL) was added dropwise to the reaction mixture, followed by stirring at the same temperature for 10 minutes and then at room temperature for 21 hours. Saturated aqueous ammonium chloride solution (2 mL) was added dropwise to the reaction mixture, and the mixture was stirred at room temperature for 1 hour. Magnesium sulfate and diethyl ether were added to the mixture, followed by further stirring for 1 hour. After filtration through Celite, the solvent was evaporated, and the residue was subjected to silica gel chromatography. Fractions eluted by dichloromethane-methanol (100:2) were concentrated under reduced pressure, to thereby yield 4-(4,5-dihydro-1,3-oxazol-2-yl)benzaldehyde mg).

$^1$H-NMR (400 MHz, CDCl$_3$) δ: 4.11 (2H, t, J=9.5 Hz), 4.48 (2H, t, J=9.8 Hz), 7.92 (2H, d, J=8.3 Hz), 8.11 (2H, d, J=8.3 Hz), 10.07 (1H, s).

Subsequently, 4-(4,5-dihydro-1,3-oxazol-2-yl)benzaldehyde (622 mg) was dissolved in tetrahydrofuran (16 mL), followed by stirring under ice cooling. Methyl magnesium bromide (1.54 mL) was added dropwise to the reaction mixture, followed by stirring under ice cooling for 15 minutes and then at room temperature for 3 hours. Saturated aqueous ammonium chloride solution (25 mL) was added dropwise to the reaction mixture, followed by stirring at room temperature for 1 hour. Water was added to the reaction mixture, and the mixture was extracted with dichloromethane-methanol, followed by drying over sodium sulfate. The solvent was evaporated, and the residue was subjected to silica gel chromatography. Fractions eluted by dichloromethane-methanol (95:5) were concentrated under reduced pressure, to thereby yield 1-[4-(4,5-dihydro-1,3-oxazol-2-yl)phenyl]-1-ethanol (548 mg).

$^1$H-NMR (400 MHz, CDCl$_3$) δ: 1.50 (3H, d, J=6.6 Hz), 4.04 (2H, t, J=9.3 Hz), 4.43 (2H, t, J=9.5 Hz), 4.93 (1H, q, J=6.6 Hz), 7.40 (2H, d, J=8.1 Hz), 7.90 (2H, d, J=8.3 Hz).

Subsequently, manganese dioxide (756 mg) was added to a solution (60 mL) of 1-[4-(4,5-dihydro-1,3-oxazol-2-yl)phenyl]-1-ethanol (548 mg) in chloroform, followed by refluxing for 5 hours. The reaction mixture was filtered through Celite, and the mother liquor was concentrated. The residue was subjected to silica gel chromatography, and fractions eluted by dichloromethane-methanol (100:3) were concentrated under reduced pressure, to thereby yield 1-[4-(4,5-dihydro-1,3-oxazol-2-yl)phenyl]-1-ethanone (279 mg).

¹H-NMR (400 MHz, CDCl₃) δ: 2.63 (3H, s), 4.10 (2H, t, J=9.5 Hz), 4.47 (2H, t, J=9.8 Hz), 7.99 (2H, d, J=8.5 Hz), 8.04 (2H, d, J=8.5 Hz).

Subsequently, dichloromethane (4 mL) and triethylamine (168 µL) were added to 1-[4-(4,5-dihydro-1,3-oxazol-2-yl)phenyl]-1-ethanone (114 mg), followed by stirring under ice cooling. Bromotrimethylsilane (160 mL) was added dropwise to the reaction mixture, followed by stirring at room temperature for 22 hours. Water was added to the reaction mixture, and the mixture was extracted with dichloromethane, followed by drying over sodium sulfate. The resultant mixture was concentrated under reduced pressure, and the concentration residue was dissolved in tetrahydrofuran (4 mL). N-Bromosuccinimide (108 mg) was added to the solution, followed by stirring at room temperature for 1 hour. The solvent was evaporated, and the residue was subjected to silica gel chromatography. Fractions eluted by dichloromethane-methanol (100:2) were concentrated under reduced pressure, to thereby yield 2-bromo-1-[4-(4,5-dihydro-1,3-oxazol-2-yl)phenyl]-1-ethanone mg).

¹H-NMR (400 MHz, CDCl₃) δ: 4.11 (2H, t, J=9.5 Hz), 4.45-4.50 (4H, m), 8.02 (2H, d, J=8.8 Hz), 8.07 (2H, d, J=8.5 Hz).

Subsequently, 2-amino-5-iodopyridine (88 mg) and 2-bromo-1-[4-(4,5-dihydro-1,3-oxazol-2-yl)phenyl]-1-ethanone mg) were dissolved in ethanol (7 mL), and sodium hydrogencarbonate (34 mg) was added to the solution, followed by refluxing for 13 hours. Dichloromethane-methanol solution was added to the reaction mixture, and the mixture was washed with water and saturated saline, followed by drying over sodium sulfate anhydrate. The solvent was evaporated, and the residue was subjected to silica gel chromatography. Fractions eluted by dichloromethane-methanol (100:5) were concentrated under reduced pressure, to thereby yield the title compound (89 mg).

¹H-NMR (400 MHz, DMSO-d₆) δ: 3.98 (2H, t, J=9.5 Hz), 4.42 (2H, t, J=9.8 Hz), 7.45 (2H, d, J=1.2 Hz), 7.93 (2H, d, J=8.3 Hz), 8.05 (2H, d, J=8.5 Hz), 8.41 (1H, s), 8.93 (1H, s).

EI-MS m/z: 389 (M)⁺.

Example 27

6-Iodo-2-[4-(1H-4-pyrazolyl)phenyl]imidazo[1,2-a]pyridine

4'-Bromoacetophenone (641 mg) and 4,4,5,5-tetramethyl-2-(1H-pyrazol-2-yl)-1,3,2-dioxaborolan (750 mg) were dissolved in 1-propanol (16 mL), and 2N sodium carbonate (5 mL) and bis(triphenylphosphine)palladium(II) dichloride (67 mg) were added to the solution, followed by heating under argon at 100° C. for 19 hours. Dichloromethane was added to the reaction mixture, and the mixture was washed sequentially with water and saturated saline, followed by drying over sodium sulfate anhydrate. The solvent was evaporated, and the residue was subjected to silica gel chromatography. Fractions eluted by dichloromethane-methanol (100:5) were concentrated under reduced pressure, to thereby yield 1-[4-(1H-4-pyrazolyl)phenyl]-1-ethanone (444 mg).

¹H-NMR (400 MHz, CDCl₃) δ: 2.62 (3H, s), 7.61 (2H, d, J=8.5 Hz), 7.94 (2H, s), 7.98 (2H, d, J=8.5 Hz).

EI-MS m/z: 186 (M)⁺.

Subsequently, 1-[4-(1H-4-pyrazolyl)phenyl]-1-ethanone (44 mg) and dimethylaminopyridine (292 mg) were dissolved in dichloromethane (30 mL), followed by stirring under ice cooling. Di-tert-butyl dicarbonate (1.1 mL) was added to the reaction mixture, followed by stirring at room temperature for 8 hours. Dichloromethane was added to the reaction mixture, and the mixture was washed sequentially with water and saturated saline, followed by drying over sodium sulfate anhydrate. The solvent was evaporated, and the residue was subjected to silica gel chromatography. Fractions eluted by dichloromethane-methanol (100:1) were concentrated under reduced pressure, to thereby yield tert-butyl 4-(4-acetylphenyl)-1H-1-pyrazolecarboxylate (659 mg).

¹H-NMR (400 MHz, CDCl₃) δ: 1.69 (9H, s), 2.61 (3H, s), 7.62 (2H, d, J=8.5 Hz), 7.99 (2H, d, J=8.2 Hz), 8.04 (1H, s), 8.39 (1H, s).

EI-MS m/z: 286 (M)⁺.

Subsequently, tert-butyl 4-(4-acetylphenyl)-1H-1-pyrazolecarboxylate (390 mg) and triethylamine (393 µL) were dissolved in dichloromethane (10 mL), and bromotrimethylsilane (374 µL) was added to the solution under ice cooling, followed by stirring under argon at room temperature for 14 hours. The reaction mixture was sequentially with water and saturated saline, followed by drying over magnesium sulfate. The solvent was evaporated under reduced pressure, and the brown residue was dissolved in tetrahydrofuran (10 mL). N-Bromosuccinimide (253 mg) was added to the solution, and the mixture was stirred at room temperature for 1 hour. Dichloromethane was added to the reaction mixture, and the mixture was washed sequentially with water and saturated saline, followed by drying over sodium sulfate anhydrate. The solvent was evaporated, and the residue was subjected to silica gel chromatography, and fractions eluted by dichloromethane-methanol (100:1) were concentrated under reduced pressure, to thereby yield tert-butyl 4-[4-(2-bromoacetyl)phenyl]-1H-1-pyrazolecarboxylate (454 mg).

¹H-NMR (400 MHz, CDCl₃) δ: 1.69 (9H, s), 4.45 (2H, s), 7.65 (2H, d, J=8.1 Hz), 8.02-8.06 (3H, m), 8.41 (1H, s).

Subsequently, 2-amino-5-iodopyridine (478 mg) and tert-butyl 4-[4-(2-bromoacetyl)phenyl]-1H-1-pyrazolecarboxylate mg) were dissolved in ethanol (20 mL), and sodium hydrogencarbonate (183 mg) was added to the solution, followed by refluxing for 16 hours. The precipitated matter was recovered through filtration and dried, to thereby yield the title compound (535 mg).

¹H-NMR (400 MHz, DMSO-d₆) δ: 7.43 (2H, t, J=10.0 Hz), 7.68 (2H, d, J=7.8 Hz), 7.93 (2H, d, J=7.8 Hz), 8.11 (2H, Br), 8.32 (1H, s), 8.90 (1H, s), 12.99 (1H, Br).

EI-MS m/z: 386 (M)⁺.

Example 28

5-Iodo-2-[4-(1H-3-pyrazolyl)phenyl]1,3-benzoxazole

2-Amino-4-bromophenol (940 mg) and 4-acetylbenzaldehyde (740 mg) were dissolved in ethanol (20 mL), followed by refluxing under heating for 3 hours. After the mixture had been left to cool, the precipitated solid was recovered through filtration, followed by washing with ethanol and drying under reduced pressure, to thereby yield 1-(4-{[(5-bromo-2-hydroxyphenyl)imino]methyl}phenyl)-1-ethanone (1.41 g).

¹H-NMR (400 MHz, DMSO-d₆) δ: 2.64 (3H, s), 6.88 (1H, d, J=8.8 Hz), 7.26 (1H, dd, J=2.4, 8.8 Hz), 7.44 (1H, d, J=2.4 Hz), 8.08 (2H, d, J=8.3 Hz), 8.16 (2H, d, J=8.3 Hz), 8.83 (1H, s), 9.47 (1H, brs).

EI-MS m/z: 317 (M)⁺.

Subsequently, 1-(4-{[(5-bromo-2-hydroxyphenyl)imino]methyl}phenyl)-1-ethanone (955 mg) was suspended in acetonitrile (200 mL), and iodobenzene diacetate (1.06 g) was added to the suspension at 50° C., followed by stirring at the same temperature for 10 minutes. The reaction mixture was concentrated under reduced pressure, and brown solid was recovered through filtration by use of isopropyl ether.

The thus-obtained brown solid was subjected to NH-silica gel column chromatography, and fractions eluted by chloroform were concentrated under reduced pressure, followed by recovering the solid through filtration by use of isopropyl ether, to thereby yield 1-[4-(5-bromo-1,3-benzoxazol-2-yl)phenyl]-1-ethanone (689 mg).

$^1$H-NMR (400 MHz, DMSO-d$_6$) δ: 2.66 (3H, s), 7.65 (1H, dd, J=2.0, 8.5 Hz), 7.83 (1H, d, J=8.5 Hz), 8.11 (1H, d, J=2.0 Hz), 8.17 (2H, d, J=8.3 Hz), 8.33 (2H, d, J=8.3 Hz).

EI-MS m/z: 315 (M)$^+$.

Subsequently, 1-[4-(5-bromo-1,3-benzoxazol-2-yl)phenyl]-1-ethanone (632 mg) and N,N-dimethylformamide dimethyl acetal (585 μL) were dissolved in N,N-dimethylformamide (20 mL), followed by heating at 100° C. for 3 hours. The reaction mixture was concentrated under reduced pressure, and the solid was recovered through filtration by use of diethyl ether, to thereby yield (E)-1-[4-(5-bromo-1,3-benzoxazol-2-yl)phenyl]-3-dimethylamino-2-propen-1-one (741 mg).

$^1$H-NMR (400 MHz, DMSO-d$_6$) δ: 2.96 (3H, s), 3.18 (3H, s), 5.91 (1H, d, J=12.2 Hz), 7.62 (1H, dd, J=2.0, 8.5 Hz), 7.79 (1H, d, J=12.2 Hz), 7.82 (1H, d, J=8.5 Hz), 8.09 (1H, d, J=2.0 Hz), 8.11 (2H, d, J=8.3 Hz), 8.25 (2H, d, J=8.3 Hz).

ESI-MS m/z: 371 (M+H)$^+$.

Subsequently, (E)-1-[4-(5-bromo-1,3-benzoxazol-2-yl)phenyl]-3-dimethylamino-2-propen-1-one (371 mg) was suspended in ethanol (15 mL), and hydrazine monohydrate (121 μL) was added to the solution, followed by refluxing under heating for 3 hours. After the mixture had been left to cool, the precipitated solid was recovered through filtration, followed by washing with ethanol and drying under reduced pressure, to thereby yield 5-bromo-2-[4-(1H-3-pyrazolyl)phenyl]-1,3-benzoxazole (316 mg).

$^1$H-NMR (400 MHz, DMSO-d$_6$) δ: 6.88 (1H, d, J=2.4 Hz), 7.60 (1H, dd, J=2.0, 8.5 Hz), 7.80 (1H, d, J=8.5 Hz), 7.855 (1H, brs), 8.06 (1H, d, J=2.0 Hz), 8.07 (2H, d, J=8.1 Hz), 8.23 (2H, d, J=8.1 Hz), 13.10 (1H, brs).

ESI-MS m/z: 340 (M+H)$^+$.

Subsequently, 5-bromo-2-[4-(1H-3-pyrazolyl)phenyl]-1,3-benzoxazole (170 mg) was dissolved in N,N-dimethylformamide (10 mL), and potassium carbonate (104 mg) and di-tert-butyl dicarbonate (138 μL) were added to the solution, followed by stirring at room temperature for 2 hours. The reaction mixture was concentrated under reduced pressure, followed by extraction with chloroform and drying over magnesium sulfate. The solvent was evaporated under reduced pressure, and the solid was recovered through filtration by use of isopropyl ether, followed by drying under reduced pressure, to thereby yield tert-butyl 3-[4-(5-bromo-1,3-benzoxazol-2-yl)phenyl]-1H-1-pyrazolecarboxylate (196 mg).

$^1$H-NMR (400 MHz, CDCl$_3$) δ: 1.69 (9H, s), 6.80 (1H, d, J=2.7 Hz), 7.48 (2H, d, J=1.2 Hz), 7.92 (1H, dd, J=1.2, 1.2 Hz), 8.09 (2H, d, J=8.3 Hz), 8.15 (1H, d, J=2.7 Hz), 8.31 (2H, d, J=8.3 Hz).

ESI-MS m/z: 440 (M+H)$^+$.

Subsequently, tert-butyl 3-[4-(5-bromo-1,3-benzoxazol-2-yl)phenyl]-1H-1-pyrazolecarboxylate (170 mg) was dissolved in 1,4-dioxane (5 mL), and bis(tributyltin) (303 μL) and tetrakis(triphenylphosphine)palladium (catalytic amount) were added to the solution, followed by refluxing with heating under argon for 6 hours. The reaction mixture was concentrated under reduced pressure, and the residue was subjected to flash chromatography. Fractions eluted by dichloromethane were concentrated under reduced pressure, to thereby yield pale yellow oily product. This product was subjected to flash chromatography again, and fractions eluted by n-hexane-ethyl acetate (10:1) were concentrated under reduced pressure, to thereby yield tert-butyl 3-{4-[5-(1,1,1-tributylstannyl)-1,3-benzoxazol-2-yl]phenyl}-1H-1-pyrazolecarboxylate (115 mg).

$^1$H-NMR (400 MHz, CDCl$_3$) δ: 0.89 (9H, t, J=7.3 Hz), 1.03-1.19 (6H, m), 1.35 (6H, q, J=7.3 Hz), 1.51-1.63 (6H, m), 1.69 (9H, s), 6.79 (1H, d, J=2.7 Hz), 7.43 (1H, d, J=7.8 Hz), 7.58 (1H, d, J=7.8 Hz), 7.90 (1H, s), 8.08 (2H, d, J=8.3 Hz), 8.14 (1H, d, J=2.7 Hz), 8.32 (2H, d, J=8.3 Hz).

FAB-MS m/z: 652 (M+H)$^+$.

Subsequently, tert-butyl 3-{4-[5-(1,1,1-tributylstannyl)-1,3-benzoxazol-2-yl]phenyl}-1H-1-pyrazolecarboxylate (26 mg) was dissolved in chloroform (1 mL), and a solution of iodine (13 mg) in chloroform (1 mL) was added to the solution, followed by stirring at room temperature for 5 minutes. The reaction mixture was washed sequentially with aqueous sodium thiosulfate, water, and saturated saline, followed by drying over magnesium sulfate. The solvent was evaporated under reduced pressure, and the solid was recovered through filtration by use of n-hexane, followed by drying under reduced pressure, to thereby yield tert-butyl 3-[4-(5-iodo-1,3-benzoxazol-2-yl)phenyl]-1H-1-pyrazolecarboxylate (19 mg).

$^1$H-NMR (400 MHz, CDCl$_3$) δ: 1.69 (9H, s), 6.80 (1H, d, J=2.9 Hz), 7.37 (1H, d, J=8.3 Hz), 7.66 (1H, dd, J=1.2, 8.5 Hz), 8.09 (2H, d, J=8.3 Hz), 8.12 (1H, d, J=1.2 Hz), 8.15 (1H, d, J=2.9 Hz), 8.30 (2H, d, J=8.3 Hz).

EI-MS m/z: 487 (M)$^+$.

Subsequently, tert-butyl 3-[4-(5-iodo-1,3-benzoxazol-2-yl)phenyl]-1H-1-pyrazolecarboxylate (14.6 mg) was dissolved in chloroform (500 μL), and trifluoroacetic acid (231 μL) was added to the solution, followed by stirring at room temperature for 1 hour. The reaction mixture was concentrated under reduced pressure, followed by drying. The thus-obtained white solid was dissolved in chloroform, and the solution was washed sequentially with 1N aqueous sodium hydroxide, water, and saturated saline, followed by drying over magnesium sulfate. The solvent was evaporated under reduce pressure, and the solid was recovered through filtration by use of isopropyl ether, followed by drying under reduced pressure, to thereby yield the title compound (9.8 mg).

$^1$H-NMR (400 MHz, DMSO-d$_6$) δ: 6.88 (1H, d, J=2.2 Hz), 7.66 (1H, d, J=8.5 Hz), 7.74 (1H, dd, J=0.7, 8.5 Hz), 7.85 (1H, brs), 8.07 (2H, d, J=8.3 Hz), 8.20 (1H, d, J=0.7 Hz), 8.23 (2H, d, J=8.3 Hz), 13.11 (1H, brs).

EI-MS m/z: 387 (M)$^+$.

Example 29

6-Iodo-2-[4-(1H-3-pyrazolyl)phenyl]1,3-benzoxazole

A solution of 3-bromophenol (10 g) in acetic acid (40 mL) was added dropwise to a solution of fuming nitric acid (2.4 mL) in acetic acid (8 mL) under ice cooling over 1 hour or longer. The mixture was stirred at room temperature for 30 minutes, and the reaction mixture was concentrated under reduced pressure. The residue was extracted with diethyl ether, followed by drying over sodium sulfate. The solvent was evaporated under reduced pressure, and the residue was subjected to flash chromatography. Fractions eluted by n-hexane-ethyl acetate (3:1) were concentrated under reduced pressure, and the solid was recovered through filtration by use of n-hexane, followed by drying, to thereby yield 5-bromo-2-nitrophenol (1.93 g).

$^1$H-NMR (400 MHz, DMSO-d$_6$) δ: 7.14 (1H, dd, J=2.0, 9.0 Hz), 7.38 (1H, d, J=2.0 Hz), 7.98 (1H, d, J=9.0 Hz), 10.62 (1H, s).

EI-MS m/z: 217 (M)$^+$.

Subsequently, 5-bromo-2-nitrophenol (1.74 g) was dissolved in 0.5% aqueous sodium hydroxide solution (180 mL), and sodium hydrosulfite (8.19 g) was added to the solution, followed by stirring at room temperature for 10 minutes. The pH of the reaction mixture was adjusted to about 5 by use of acetic acid, and the mixture was extracted with diethyl ether, followed by drying over sodium sulfate. The solvent was evaporated under reduced pressure, and the residue was subjected to flash chromatography. Fractions eluted by n-hexane-ethyl acetate (3:1) were concentrated under reduced pressure, and the solid was recovered through filtration by use of n-hexane, followed by drying, to thereby yield 2-amino-5-bromophenol (827 mg).

$^1$H-NMR (400 MHz, DMSO-d$_6$) δ: 4.65 (2H, brs), 6.51 (1H, d, J=8.3 Hz), 6.67 (1H, dd, J=2.2, 8.3 Hz), 6.75 (1H, d, J=2.2 Hz), 9.44 (1H, brs). ESI-MS m/z: 188 (M+H)$^+$.

Subsequently, 2-amino-5-bromophenol (752 mg) and 4-acetylbenzaldehyde (592 mg) were dissolved in ethanol (20 mL), followed by refluxing under heating for 3 hours. The solution was left to cool, and the precipitated solid was recovered through filtration, followed by washing with ethanol and drying under reduced pressure, to thereby yield 1-(4-{[(4-bromo-2-hydroxyphenyl)imino]methyl}phenyl)-1-ethanone (1.03 g).

$^1$H-NMR (400 MHz, CDCl$_3$) δ: 2.64 (3H, s), 7.02 (1H, dd, J=2.2, 8.3 Hz), 7.09 (1H, d, J=2.2 Hz), 7.20 (1H, d, J=8.3 Hz), 8.07 (2H, d, J=8.3 Hz), 8.14 (2H, d, J=8.3 Hz), 8.82 (1H, s), 9.70 (1H, brs).

EI-MS m/z: 317 (M)$^+$.

Subsequently, 1-(4-{[(4-bromo-2-hydroxyphenyl)imino]methyl}phenyl)-1-ethanone (955 mg) was suspended in acetonitrile (200 mL), and iodobenzene diacetate (1.06 g) was added to the solution at 50° C., followed by stirring at the same temperature for 10 minutes. The reaction mixture was concentrated under reduced pressure, and brown solid was recovered through filtration by use of isopropyl ether. The thus-obtained brown solid was subjected to NH-silica gel column chromatography, and fractions eluted by dichloromethane were concentrated under reduced pressure, followed by recovering the solid through filtration isopropyl ether, to thereby yield 1-[4-(6-bromo-1,3-benzoxazol-2-yl)phenyl]-1-ethanone (586 mg).

$^1$H-NMR (400 MHz, DMSO-d$_6$) δ: 2.68 (3H, s), 7.52 (1H, dd, J=1.7, 8.5 Hz), 7.67 (1H, d, J=8.5 Hz), 7.79 (1H, d, J=1.7 Hz), 8.11 (2H, d, J=8.5 Hz), 8.34 (2H, dt, J=1.7, 8.5 Hz).

EI-MS m/z: 315 (M)$^+$.

Subsequently, 1-[4-(6-bromo-1,3-benzoxazol-2-yl)phenyl]-1-ethanone (569 mg) and N,N-dimethylformamide dimethyl acetal (531 μL) were dissolved in N,N-dimethylformamide (20 mL), followed by heating at 100° C. for 2 hours. The reaction mixture was concentrated under reduced pressure, and the solid was recovered through filtration by use of diethyl ether, to thereby yield (E)-1-[4-(6-bromo-1,3-benzoxazol-2-yl)phenyl]-3-dimethylamino-2-propen-1-one (640 mg).

$^1$H-NMR (400 MHz, DMSO-d$_6$) δ: 2.96 (3H, s), 2.94 (3H, s), 5.91 (1H, d, J=12.2 Hz), 7.61 (1H, dd, J=1.7, 8.5 Hz), 7.79 (1H, d, J=12.2 Hz), 7.80 (1H, d, J=8.5 Hz), 8.11 (2H, d, J=8.3 Hz), 8.16 (1H, d, J=1.7 Hz), 8.24 (2H, d, J=8.3 Hz).

EI-MS m/z: 370 (M)$^+$.

Subsequently, (E)-1-[4-(6-bromo-1,3-benzoxazol-2-yl)phenyl]-3-dimethylamino-2-propen-1-one (594 mg) was suspended in ethanol (20 mL), and hydrazine monohydrate (194 μL) was added to the suspension, followed by refluxing under heating for 2 hours. After the mixture had been left to cool, the precipitated solid was recovered through filtration, followed by washing with ethanol and drying under reduced pressure, to thereby yield 6-bromo-2-[4-(1H-3-pyrazolyl)phenyl]-1,3-benzoxazole (494 mg).

$^1$H-NMR (400 MHz, DMSO-d$_6$) δ: 6.88 (1H, d, J=2.3 Hz), 7.60 (1H, dd, J=1.7, 8.5 Hz), 7.78 (1H, d, J=8.5 Hz), 7.85 (1H, brs), 8.07 (2H, d, J=8.0 Hz), 8.13 (1H, d, J=1.7 Hz), 8.22 (2H, d, J=8.0 Hz), 13.10 (1H, brs).

EI-MS m/z: 339 (M)$^+$.

Subsequently, 6-bromo-2-[4-(1H-3-pyrazolyl)phenyl]-1,3-benzoxazole (476 mg) was dissolved in N,N-dimethylformamide (10 mL), and potassium carbonate (232 mg) and di-tert-butyl dicarbonate (354 μL) were added to the solution, followed by stirring at room temperature for 2 hours. The reaction mixture was concentrated under reduced pressure, followed by extraction with chloroform and drying over magnesium sulfate. The solvent was evaporated under reduced pressure, and the solid was recovered through filtration by use of isopropyl ether, followed by drying under reduced pressure, to thereby yield tert-butyl 3-[4-(6-bromo-1,3-benzoxazol-2-yl)phenyl]-1H-1-pyrazolecarboxylate (575 mg).

$^1$H-NMR (400 MHz, CDCl$_3$) δ: 1.69 (9H, s), 6.79 (1H, d, J=2.9 Hz), 7.49 (1H, dd, J=1.7, 8.5 Hz), 7.64 (1H, d, J=8.5 Hz), 7.77 (1H, d, J=1.7 Hz), 8.08 (2H, d, J=8.3 Hz), 8.14 (1H, d, J=2.9 Hz), 8.29 (2H, d, J=8.3 Hz).

EI-MS m/z: 439 (M)$^+$.

Subsequently, tert-butyl 3-[4-(6-bromo-1,3-benzoxazol-2-yl)phenyl]-1H-1-pyrazolecarboxylate (440 mg) was dissolved in 1,4-dioxane (20 mL), and bis(tributyltin) (758 μL) and tetrakis(triphenylphosphine)palladium (35 mg) were added to the solution, followed by refluxing with heating under argon for 6 hours. The reaction mixture was concentrated under reduced pressure, and the residue was subjected to flash chromatography, and fractions eluted by chloroform were concentrated under reduced pressure, to thereby yield a pale yellow oily product. This product was subjected to flash chromatography again, and fractions eluted by n-hexane-ethyl:acetate (12:1) were concentrated under reduced pressure, to thereby yield tert-butyl 3-{4-[6-(1,1,1-tributylstannyl)-1,3-benzoxazol-2-yl]phenyl}-1H-1-pyrazolecarboxylate (240 mg).

$^1$H-NMR (400 MHz, CDCl$_3$) δ: 0.90 (9H, t, J=7.3 Hz), 1.06-1.21 (6H, m), 1.36 (6H, q, J=7.3 Hz), 1.51-1.61 (6H, m), 1.69 (9H, s), 6.79 (1H, dd, J=0.5, 2.7 Hz), 7.43 (1H, d, J=7.6 Hz), 7.70 (1H, d, J=0.5 Hz), 7.76 (1H, d, J=7.6 Hz), 8.08 (2H, d, J=8.3 Hz), 8.14 (1H, dd, J=0.5, 2.7 Hz), 8.31 (2H, d, J=8.3 Hz).

FAB-MS m/z: 652 (M+H)$^+$.

Subsequently, tert-butyl 3-{4-[6-(1,1,1-tributylstannyl)-1,3-benzoxazol-2-yl]phenyl}-1H-1-pyrazolecarboxylate (150 mg) was dissolved in tetrahydrofuran (2 mL), and a solution of iodine (63 mg) in tetrahydrofuran (1 mL) was added to the solution, followed by stirring at room temperature for 5 minutes. The reaction mixture was diluted with chloroform, and then washed sequentially with aqueous sodium thiosulfate solution, water, and saturated saline, followed by drying over magnesium sulfate. The solvent was evaporated under reduced pressure, and the solid was recovered through filtration by use of n-hexane, followed by drying under reduced pressure, to thereby yield tert-butyl 3-[4-(6-iodo-1,3-benzoxazol-2-yl)phenyl]-1H-1-pyrazolecarboxylate (98 mg).

$^1$H-NMR (400 MHz, CDCl$_3$) δ: 1.69 (9H, s), 6.79 (1H, dd, J=0.5, 2.9 Hz), 7.53 (1H, d, J=8.3 Hz), 7.68 (1H, dd, J=1.5, 8.3 Hz), 7.96 (1H, d, J=1.5 Hz), 8.08 (2H, d, J=8.3 Hz), 8.15 (1H, d, J=2.9 Hz), 8.30 (2H, d, J=8.3 Hz).

EI-MS m/z: 487 (M)$^+$.

Subsequently, tert-butyl 3-[4-(6-iodo-1,3-benzoxazol-2-yl)phenyl]-1H-1-pyrazolecarboxylate (49 mg) was dissolved in a mixture of tetrahydrofuran (2 mL) and ethanol (2 mL), and 6N hydrochloric acid (500 µL) was added to the solution, followed by stirring at 80° C. for 2 hours. The reaction mixture was alkalified with 1N sodium hydroxide, followed by stirring at 80° C. for 1 hour. The reaction mixture was concentrated under reduced pressure, followed by drying. The thus-obtained white solid was recovered through filtration, and washed sequentially with water and ethanol, followed by drying under reduced pressure, to thereby yield the title compound (26 mg).

$^1$H-NMR (400 MHz, DMSO-$d_6$) δ: 6.88 (1H, d, J=2.0 Hz), 7.63 (1H, d, J=8.0 Hz), 7.74 (1H, d, J=8.0 Hz), 7.83 (1H, brs), 8.06 (2H, d, J=8.3 Hz), 8.22 (2H, d, J=8.3 Hz), 8.24 (1H, s), 13.12 (1H, brs).

EI-MS m/z: 387 (M)$^+$.

Example 30

5-Iodo-2-[4-(1,2,4-oxadiazol-3-yl)phenyl]-1,3-benzoxazole

2-Amino-4-bromophenol (2.07 g) and 4-cyanobenzaldehyde (1.44 g) were dissolved in ethanol (50 mL), followed by refluxing under heating for 3 hours. The reaction mixture was concentrated, and the solid was recovered through filtration, followed by washing with diethyl ether and drying under reduced pressure, to thereby yield 4-{[(5-bromo-2-hydroxyphenyl)imino]methyl}benzonitrile (2.73 g).

$^1$H-NMR (400 MHz, CDCl$_3$) δ: 6.87 (1H, dd, J=0.7, 8.5 Hz), 7.27 (1H, ddd, J=0.7, 2.4, 8.5 Hz), 7.47 (1H, dd, J=0.7, 2.4 Hz), 7.99 (2H, d, J=8.1 Hz), 8.21 (2H, d, J=8.1 Hz), 8.85 (1H, s), 9.45 (1H, brs).

EI-MS m/z: 300 (M)$^+$.

Subsequently, 4-{[(5-bromo-2-hydroxyphenyl)imino]methyl}benzonitrile (2.71 g) was suspended in acetonitrile (200 mL), and iodobenzene diacetate (2.90 g) was added to the suspension, followed by stirring at room temperature for 30 minutes. The reaction mixture was concentrated under reduced pressure, followed by extraction with chloroform and drying over magnesium sulfate. The thus-obtained brown solid was subjected to flash column chromatography, and fractions eluted by dichloromethane were concentrated under reduced pressure, followed by recovering the solid through filtration by use of n-hexane, to thereby yield a pale yellow solid. This solid was further subjected to NH-silica gel column chromatography, and fractions eluted by chloroform were concentrated under reduced pressure, followed by recovering the solid through filtration by use of diethyl ether, to thereby yield 4-(5-bromo-1,3-benzoxazol-2-yl)benzonitrile (1.00 g).

$^1$H-NMR (400 MHz, DMSO-$d_6$) δ: 7.66 (1H, d, J=8.5 Hz), 7.84 (1H, d, J=8.5 Hz), 8.10 (2H, d, J=8.1 Hz), 8.13 (1H, s), 8.35 (2H, d, J=8.1 Hz).

EI-MS m/z: 298 (M)$^+$.

Subsequently, 4-(5-bromo-1,3-benzoxazol-2-yl)benzonitrile (598 mg) was suspended in methanol (20 mL), and hydroxylamine hydrochloride (417 mg) and potassium carbonate (829 mg) were added to the suspension, followed by refluxing under heating for 12 hours. After the reaction mixture had been left to cool, water (10 mL) was added to the mixture, and the precipitated solid was recovered through filtration, followed by washing with 50% ethanol and drying under reduced pressure, to thereby yield N-hydroxy-4-(5-bromo-1,3-benzoxazol-2-yl)benzamidine (511 mg).

$^1$H-NMR (400 MHz, DMSO-$d_6$) δ: 5.97 (2H, s), 7.60 (1H, dd, J=2.0, 8.5 Hz), 7.79 (1H, d, J=8.5 Hz), 7.92 (2H, d, J=8.3 Hz), 8.06 (1H, d, J=2.0 Hz), 8.19 (2H, d, J=8.3 Hz), 9.93 (1H, s).

EI-MS m/z: 331 (M)$^+$.

Subsequently, N-hydroxy-4-(5-bromo-1,3-benzoxazol-2-yl)benzamidine (266 mg) was suspended in triethyl orthoformate (3 mL), followed by refluxing under heating for 24 hours. The reaction mixture was concentrated, and the solid was recovered through filtration by use of isopropyl ether, followed by drying under reduced pressure, to thereby yield 5-bromo-2-[4-(1,2,4-oxadiazol-3-yl)phenyl]-1,3-benzoxazole (190 mg).

$^1$H-NMR (400 MHz, DMSO-$d_6$) δ: 7.64 (1H, dd, J=1.7, 8.5 Hz), 7.83 (1H, d, J=8.5 Hz), 8.11 (1H, d, J=1.7 Hz), 8.28 (2H, d, J=8.3 Hz), 8.39 (2H, d, J=8.3 Hz), 9.81 (1H, s).

FAB-MS m/z: 342 (M+H)$^+$.

Subsequently, 5-bromo-2-[4-(1,2,4-oxadiazol-3-yl)phenyl]-1,3-benzoxazole (171 mg) was dissolved in 1,4-dioxane (10 mL), and bis(tributyltin) (505 µL) and tetrakis(triphenylphosphine)palladium (catalytic amount) were added to the solution, followed by refluxing with heating under argon overnight. The reaction mixture was diluted with ethyl acetate, followed by filtration through Celite. The filtrate was concentrated under reduced pressure, and the residue was subjected to flash chromatography. Fractions eluted by n-hexane-ethyl acetate (10:1) were concentrated under reduced pressure, to thereby yield 2-[4-(1,2,4-oxadiazol-3-yl)phenyl]-5-(1,1,1-tributylstannyl)-1,3-benzoxazole (74 mg).

$^1$H-NMR (400 MHz, CDCl$_3$) δ: 0.89 (9H, t, J=7.3 Hz), 1.05-1.20 (6H, m), 1.35 (6H, q, J=7.3 Hz), 1.51-1.63 (6H, m), 7.46 (1H, d, J=8.1 Hz), 7.60 (1H, d, J=8.1 Hz), 7.92 (1H, d, J=0.5 Hz), 8.29 (2H, d, J=8.3 Hz), 8.40 (2H, d, J=8.3 Hz), 8.81 (1H, s). FAB-MS m/z: 554 (M+H)$^+$.

Subsequently, 2-[4-(1,2,4-oxadiazol-3-yl)phenyl]-5-(1,1,1-tributylstannyl)-1,3-benzoxazole (55 mg) was dissolved in chloroform (2 mL), and a solution of iodine (28 mg) in chloroform (1 mL) was added to the solution, followed by stirring at room temperature for 5 minutes. The reaction mixture was washed sequentially with aqueous sodium thiosulfate solution, water, and saturated saline, followed by drying over magnesium sulfate. The solvent was evaporated under reduced pressure, and the solid was recovered through filtration by use of isopropyl ether, followed by drying under reduced pressure, to thereby yield the title compound (19 mg).

$^1$H-NMR (400 MHz, DMSO-$d_6$) δ: 7.70 (1H, d, J=8.5 Hz), 7.78 (1H, dd, J=1.7, 8.5 Hz), 8.24 (1H, s), 8.28 (2H, d, J=8.1 Hz), 8.39 (2H, d, J=8.1 Hz), 9.81 (1H, d, J=1.0 Hz).

EI-MS m/z: 389 (M)$^+$.

Example 31

5-[4-(5-Iodo-1H-benz[d]imidazol-2-yl)phenyl]-1,3-oxazole

4-Bromo-2-nitroaniline (434 mg) and 4-(1,3-oxazol-5-yl)benzaldehyde (346 mg) were dissolved in ethanol (15 mL), and 1M aqueous sodium hydrosulfite solution (6 mL) was added to the solution, followed by refluxing under heating for 10 hours. After the mixture had been left to cool, 5N aqueous ammonia solution (4 mL) was added to the reaction mixture, and the precipitated solid was recovered through filtration, followed by washing with water and drying under reduced pressure, to thereby yield 5-[4-(5-bromo-1H-benz[d]imidazol-2-yl)phenyl]-1,3-oxazole (480 mg).

¹H-NMR (400 MHz, CD₃OD) δ: 7.39 (1H, dd, J=1.7, 8.5 Hz), 7.52 (1H, d, J=8.5 Hz), 7.66 (1H, s), 7.76 (1H, brs), 7.90 (2H, d, J=8.5 Hz), 8.15 (2H, d, J=8.5 Hz), 8.31 (1H, s) EI-MS m/z: 339 (M)⁺.

Subsequently, 5-[4-(5-bromo-1H-benz[d]imidazol-2-yl) phenyl]-1,3-oxazole (204 mg) was dissolved in N,N-dimethylformamide (2 mL), and potassium carbonate (100 mg) and di-tert-butyl dicarbonate (152 μL) were added to the solution, followed by stirring at room temperature for 3 hours. The reaction mixture was concentrated under reduced pressure, followed by extraction with chloroform and drying over magnesium sulfate. The solvent was evaporated under reduced pressure, and the solid was recovered through filtration by use of isopropyl ether, followed by drying under reduced pressure, to thereby yield a 1:1 mixture (123 mg) of tert-butyl 5-bromo-2-[4-(1,3-oxazol-5-yl)phenyl]-1H-benz[d]imidazole-1-carboxylate and tert-butyl 6-bromo-2-[4-(1,3-oxazol-5-yl)phenyl]-1H-benz[d]imidazole-1-carboxylate.

EI-MS m/z: 439 (M)⁺.

Subsequently, a 1:1 mixture (110 mg) of tert-butyl 5-bromo-2-[4-(1,3-oxazol-5-yl)phenyl]-1H-benz[d]imidazole-1-carboxylate and tert-butyl 6-bromo-2-[4-(1,3-oxazol-5-yl)phenyl]-1H-benz[d]imidazole-1-carboxylate was dissolved in 1,4-dioxane (2 mL), and bis(tributyltin) (253 μL) and tetrakis(triphenylphosphine)palladium (catalytic amount) were added to the solution, followed by refluxing with heating under argon for 3 hours. The reaction mixture was concentrated, and the residue was subjected to flash chromatography. Fractions eluted by n-hexane-ethyl acetate (2:1) were concentrated under reduced pressure, to thereby yield a 1:1 mixture (113 mg) of tert-butyl 2-[4-(1,3-oxazol-5-yl)phenyl]-5-(1,1,1-tributylstannyl)-1H-benz[d]imidazole-1-carboxylate and tert-butyl 2-[4-(1,3-oxazol-5-yl)phenyl]-6-(1,1,1-tributylstannyl)-1H-benz[d]imidazole-1-carboxylate.

FAB-MS m/z: 652 (M+H)⁺.

Subsequently, a 1:1 mixture (98 mg) of tert-butyl 2-[4-(1,3-oxazol-5-yl)phenyl]-5-(1,1,1-tributylstannyl)-1H-benz[d]imidazole-1-carboxylate and tert-butyl 2-[4-(1,3-oxazol-5-yl)phenyl]-6-(1,1,1-tributylstannyl)-1H-benz[d]imidazole-1-carboxylate was dissolved in chloroform (1 mL), and a solution of iodine (28 mg) in chloroform (1 mL) was added to the solution, followed by stirring at room temperature for 5 minutes. The reaction mixture was washed sequentially with aqueous sodium thiosulfate solution, water, and saturated saline, followed by drying over magnesium sulfate. The solvent was evaporated under reduced pressure, and the solid was dissolved in methanol (2 mL), and 3N hydrochloric acid (500 μL) was added to the solution, followed by stirring at room temperature overnight. 3N Aqueous sodium hydroxide solution (600 μL) was added to the reaction mixture, followed by extraction with chloroform, sequentially washing with water and saturated saline, and drying over magnesium sulfate. The solvent was evaporated under reduced pressure, and the solid was recovered through filtration by use of isopropyl ether, followed by drying under reduced pressure, to thereby yield the title compound (46 mg).

¹H-NMR (400 MHz, CD₃OD) δ: 7.42 (1H, d, J=8.5 Hz), 7.56 (1H, dd, J=1.7, 8.5 Hz), 7.66 (1H, s), 7.91 (2H, d, J=8.5 Hz), 7.96 (1H, brs), 8.16 (2H, d, J=8.5 Hz), 8.31 (1H, s).

EI-MS m/z: 387 (M)⁺.

Example 32

5-Iodo-2-[4-(1H-3-pyrazolyl)phenyl]-1H-benz[d] imidazole

4-Bromo-2-nitroaniline (651 mg) and 4-acetylbenzaldehyde (444 mg) were dissolved in ethanol (12 mL), and 1M aqueous sodium hydrosulfite solution (9 mL) was added to the solution, followed by refluxing under heating for 8 hours. After the reaction mixture had been left to cool, 5N aqueous ammonia solution (6 mL) was added thereto, and the precipitated solid was recovered through filtration, followed by washing with water and drying under reduced pressure, to thereby yield 1-[4-(5-bromo-1H-benz[d]imidazol-2-yl)phenyl]-1-ethanone (597 mg).

¹H-NMR (400 MHz, CD₃OD) δ: 2.66 (3H, s), 7.41 (1H, dd, J=1.7, 8.5 Hz), 7.55 (1H, d, J=8.5 Hz), 7.78 (1H, d, J=1.7 Hz), 8.15 (2H, d, J=8.8 Hz), 8.20 (2H, d, J=8.8 Hz).

EI-MS m/z: 314 (M)⁺.

Subsequently, 1-[4-(5-bromo-1H-benz[d]imidazol-2-yl) phenyl]-1-ethanone (592 mg) and N,N-dimethylformamide dimethyl acetal (468 μL) were dissolved in N,N-dimethylformamide (10 mL), followed by heating at 100° C. for 2 hours. The reaction mixture was concentrated, and the residue was subjected to flash chromatography. Fraction eluted by dichloromethane-methanol (15:1) were concentrated under reduced pressure, followed by recovering the solid through filtration by use of isopropyl ether, to thereby yield a 1:1 mixture (116 mg) of (E)-1-[4-(5-bromo-1H-benz[d]imidazol-2-yl)phenyl]-3-dimethylamino-2-propen-1-one and (E)-1-[4-(6-bromo-1H-benz[d]imidazol-2-yl)phenyl]-3-dimethylamino-2-propen-1-one.

EI-MS m/z: 369 (M)⁺.

Subsequently, a 1:1 mixture (93 mg) of (E)-1-[4-(5-bromo-1H-benz[d]imidazol-2-yl)phenyl]-3-dimethylamino-2-propen-1-one and (E)-1-[4-(5-bromo-1H-benz[d]imidazol-2-yl) phenyl]-3-dimethylamino-2-propen-1-one was suspended in ethanol (2 mL), and hydrazine monohydrate (30 μL) was added to the suspension, followed by refluxing under heating for 2 hours. After the mixture had been left to cool, the reaction mixture was concentrated. The residue was recovered through filtration by use of diethyl ether, followed by drying under reduced pressure, to thereby yield 5-bromo-2-[4-(1H-3-pyrazolyl)phenyl]-1H-benz[d]imidazole (83 mg).

¹H-NMR (400 MHz, CD₃OD) δ: 6.79 (1H, d, J=2.2 Hz), 7.39 (1H, dd, J=1.7, 8.5 Hz), 7.53 (1H, d, J=8.5 Hz), 7.72 (1H, brs), 7.77 (1H, s), 7.98 (2H, d, J=8.3 Hz), 8.14 (2H, d, J=8.3 Hz).

EI-MS m/z: 338 (M)⁺.

Subsequently, 5-bromo-2-[4-(1H-3-pyrazolyl)phenyl]-1H-benz[d]imidazole (75 mg) was dissolved in N,N-dimethylformamide (1 mL), and potassium carbonate (67 mg) and di-tert-butyl dicarbonate (106 μL) were added to the solution, followed by stirring at room temperature for 2 hours. The reaction mixture was diluted with water, and the mixture was extracted with ethyl acetate, followed by washing sequentially with water and saturated saline and then drying over sodium sulfate. The product was subjected to flash chromatography, and fractions eluted by n-hexane-ethyl:acetate (4:1) were concentrated under reduced pressure, to thereby yield a 1:1 mixture (118 mg) of tert-butyl 5-bromo-2-{4-[(tert-butoxycarbonyl)-1H-3-pyrazolyl]phenyl}-1H-benz[d]imidazole-1-carboxylate and tert-butyl 6-bromo-2-{4-[(tert-butoxycarbonyl)-1H-3-pyrazolyl]phenyl}-1H-benz[d] imidazole-1-carboxylate.

EI-MS m/z: 538 (M)⁺.

Subsequently, a 1:1 mixture (97 mg) of tert-butyl 5-bromo-2-{4-[(tert-butoxycarbonyl)-1H-3-pyrazolyl]phenyl}-1H-benz[d]imidazole-1-carboxylate and tert-butyl 6-bromo-2-{4-[(tert-butoxycarbonyl)-1H-3-pyrazolyl]phenyl}-1H-benz [d]imidazole-1-carboxylate was dissolved in 1,4-dioxane (2 mL), and bis(tributyltin) (182 μL) and tetrakis(triphenylphosphine)palladium (catalytic amount) were added to the solution, followed refluxing with heating under argon for 2 hours.

The reaction mixture was diluted with ethyl acetate, followed by filtration through Celite. The filtrate was concentrated under reduced pressure, and the residue was subjected to flash chromatography. Fractions eluted by n-hexane-ethyl acetate (6:1) were concentrated under reduced pressure, to thereby yield a 1:1 mixture (82 mg) of tert-butyl 2-{4-[(tert-butoxycarbonyl)-1H-3-pyrazolyl]phenyl}-5-(1,1,1-tributylstannyl)-1H-benz[d]imidazole-1-carboxylate and tert-butyl 2-{4-[(tert-butoxycarbonyl)-1H-3-pyrazolyl]phenyl}-6-(1,1,1-tributylstannyl)-1H-benz[d]imidazole-1-carboxylate.

FAB-MS m/z: 751 (M+H)$^+$.

Subsequently, a 1:1 mixture (75 mg) of tert-butyl 2-{4-[(tert-butoxycarbonyl)-1H-3-pyrazolyl]phenyl}-5-(1,1,1-tributylstannyl)-1H-benz[d]imidazole-1-carboxylate and tert-butyl 2-{4-[(tert-butoxycarbonyl)-1H-3-pyrazolyl]phenyl}-6-(1,1,1-tributylstannyl)-1H-benz[d]imidazole-1-carboxylate was dissolved in chloroform (2 mL), and a solution of iodine (28 mg) in chloroform (1 mL) was added to the solution, followed by stirring at room temperature for 5 minutes. The reaction mixture was washed sequentially with aqueous sodium thiosulfate solution, water, and saturated saline, followed by drying over magnesium sulfate. The solvent was evaporated under reduced pressure, and the solid was dissolved in methanol (2 mL). 3N Hydrochloric acid (500 µL) was added to the solution, followed by stirring at room temperature overnight. 3N Aqueous sodium hydroxide solution (1 mL) was added to the reaction mixture, and the mixture was extracted with chloroform, followed by washing sequentially with water and saturated saline and then drying over magnesium sulfate. The solvent was evaporated under reduced pressure, and the solid was recovered through filtration by use of diethyl ether, followed by drying under reduced pressure, to thereby yield the title compound (34 mg).

$^1$H-NMR (400 MHz, CD$_3$OD) δ: 6.79 (1H, d, J=2.2 Hz), 7.42 (1H, d, J=8.5 Hz), 7.56 (1H, dd, J=1.7, 8.5 Hz), 7.71 (1H, d, J=2.2 Hz), 7.96 (1H, d, J=1.7 Hz), 7.97 (2H, d, J=8.5 Hz), 8.14 (2H, d, J=8.5 Hz).

EI-MS m/z: 386 (M)$^+$.

Example 33

5-[4-(6-Iodo-3H-imidazo[4,5-b]pyridin-2-yl)phenyl]-1,3-oxazole

2-Amino-5-bromo-3-nitropyridine (218 mg) and 4-(1,3-oxazol-5-yl)benzaldehyde (173 mg) were suspended in dimethylsulfoxide (2 mL), followed by stirring at 80° C. for 20 minutes. Ethanol (4 mL) and 1M aqueous sodium hydrosulfite solution (3 mL) were added to the solution, followed by refluxing under heating for 15 hours. After the reaction mixture had been left to cool, water (20 mL) and concentrated aqueous ammonia solution (500 µL) were added thereto, and the precipitated solid was recovered through filtration, followed by washing with water and drying under reduced pressure, to thereby yield a 1:1 mixture (258 mg) of 5-[4-(6-bromo-3H-imidazo[4,5-b]pyridin-2-yl)phenyl]-1,3-oxazole and 5-[4-(6-bromo-1H-imidazo[4,5-b]pyridin-2-yl)phenyl]-1,3-oxazole.

Subsequently, a 1:1 mixture (239 mg) of 5-[4-(6-bromo-3H-imidazo[4,5-b]pyridin-2-yl)phenyl]-1,3-oxazole and 5-[4-(6-bromo-1H-imidazo[4,5-b]pyridin-2-yl)phenyl]-1,3-oxazole was dissolved in N,N-dimethylformamide (4 mL), and potassium carbonate (124 mg) and di-tert-butyl dicarbonate (184 µL) were added to the solution, followed by stirring at room temperature for 3 hours. The reaction mixture was concentrated under reduced pressure, extracted with ethyl acetate, washed sequentially with water and saturated saline, and dried over sodium sulfate. The solvent was evaporated under reduced pressure, and the residue was subjected to flash chromatography. Fractions eluted by n-hexane-ethyl:acetate (1:1) were concentrated under reduced pressure, and the solid was recovered through filtration by use of diethyl ether, followed by drying under reduced pressure, to thereby yield a 1:1 mixture (200 mg) of tert-butyl 6-bromo-2-[4-(1,3-oxazol-5-yl)phenyl]-3H-imidazo[4,5-b]pyridine-3-carboxylate and tert-butyl 6-bromo-2-[4-(1,3-oxazol-5-yl)phenyl]-1H-imidazo[4,5-b]pyridine-1-carboxylate.

Subsequently, a 1:1 mixture (71 mg) of tert-butyl 6-bromo-2-[4-(1,3-oxazol-5-yl)phenyl]-3H-imidazo[4,5-b]pyridine-3-carboxylate and tert-butyl 6-bromo-2-[4-(1,3-oxazol-5-yl)phenyl]-1H-imidazo[4,5-b]pyridine-1-carboxylate was dissolved in N,N-dimethylformamide (2 mL) and 1,4-dioxane (1 mL), and bis(tributyltin) (121 µL) and tetrakis(triphenylphosphine)palladium (catalytic amount) were added to the solution, followed by refluxing with heating under argon overnight. The reaction mixture was diluted with ethyl acetate. After filtration through Celite, the filtrate was concentrated under reduced pressure, and the residue was subjected to flash chromatography. Fractions eluted by n-hexane-ethyl acetate (1:1) were concentrated under reduced pressure, to thereby yield 5-{4-[6-(1,1,1-tributylstannyl)-3H-imidazo[4,5-b]pyridin-2-yl]phenyl}-1,3-oxazole (17 mg).

$^1$H-NMR (400 MHz, CDCl$_3$) δ: 0.90 (9H, t, J=7.3 Hz), 1.13-1.30 (6H, m), 1.38 (6H, q, J=7.3 Hz), 1.55-1.67 (6H, m), 7.50 (1H, s), 7.89 (2H, d, J=8.5 Hz), 8.00 (1H, s), 8.32 (1H, d, J=1.0 Hz), 8.42 (2H, d, J=8.5 Hz), 8.48 (1H, d, J=1.0 Hz).

EI-MS m/z: 552 (M)$^+$.

Subsequently, 5-{4-[6-(1,1,1-tributylstannyl)-3H-imidazo[4,5-b]pyridin-2-yl]phenyl}-1,3-oxazole (13 mg) was dissolved in tetrahydrofuran (1 mL), and a solution of iodine (28 mg) in tetrahydrofuran (1 mL) was added to the solution, followed by stirring at room temperature for 5 minutes. The reaction mixture was concentrated under reduced pressure, and the solid was recovered through filtration by use of methanol, followed by washing and then drying under reduced pressure, to thereby yield the title compound (8 mg).

$^1$H-NMR (400 MHz, DMSO-d$_6$) δ: 7.87 (1H, s), 7.95 (2H, d, J=8.5 Hz), 8.32 (2H, d, J=8.5 Hz), 8.42 (1H, brs), 8.53 (1H, s), 8.54 (1H, brs).

EI-MS m/z: 388 (M)$^+$.

Example 34

N1-(2-Methyl-2-sulfanylpropyl)-N-1-{2-[(2-methyl-2-sulfanylpropyl)amino]ethyl}-2-[3-(4-imidazo[1,2-a]pyridin-2-ylphenyl)-1H-1-pyrazolyl]acetamide 2-Aminopyridine (1.88 g) and 2-bromo-4'-cyanoacetophenone (4.48 g) were dissolved in ethanol (40 mL), and sodium hydrogencarbonate (1.85 g) was added to the solution, followed by refluxing for 10 hours. Water was added to the reaction mixture, and the mixture was extracted with chloroform, followed by drying over magnesium sulfate. The solvent was evaporated under reduced pressure, and the residue was subjected to flash column chromatography. Fractions eluted by dichloromethane-methanol (100:1) were concentrated under reduced pressure, and the solid was recovered through filtration by use of diethyl ether, to thereby yield 4-imidazo[1,2-a]pyridin-2-ylbenzonitrile (3.82 g).

$^1$H-NMR (400 MHz, DMSO-d$_6$) δ: 6.94 (1H, tt, J=1.0, 6.8 Hz), 7.30 (1H, ddt, J=1.0, 6.8, 9.0 Hz), 7.62 (1H, d, J=9.0 Hz), 7.90 (2H, d, J=8.5 Hz), 8.16 (2H, d, J=8.5 Hz), 8.56 (1H, ddd, J=1.0, 2.0, 6.8 Hz), 8.60 (1H, s).

Subsequently, 4-imidazo[1,2-a]pyridin-2-ylbenzonitrile (3.51 g) was dissolved in a mixture of tetrahydrofuran (70 mL) and dichloromethane (70 mL), followed by stirring under ice cooling. Diisobutylaluminum hydride (1.0M n-hexane solution, 35.2 mL) was added dropwise to the reaction mixture, followed by stirring at the same temperature for 15 minutes and then at room temperature for 2 hours. Saturated aqueous ammonium chloride solution (5 mL) was added dropwise to the reaction mixture, followed by stirring at room temperature for 1 hour. Magnesium sulfate and dichloromethane (200 mL) were added to the mixture, followed by further stirring for 1 hour. After filtration through Celite, the solvent was evaporated, and the solid was recovered through filtration by use of diethyl ether, to thereby yield 4-imidazo[1,2-a]pyridin-2-ylbenzaldehyde (2.79 g).

$^1$H-NMR (400 MHz, DMSO-$d_6$) δ: 6.94 (1H, dddd, J=1.0, 1.0, 6.8, 6.8 Hz) 7.29 (1H, dddd, J=1.0, 1.0, 6.8, 9.3 Hz), 7.62 (1H, ddd, J=1.0, 1.0, 9.3 Hz), 7.98 (2H, d, J=8.3 Hz), 8.20 (2H, d, J=8.3 Hz), 8.56 (1H, dddd, J=1.0, 1.0, 1.0, 6.8 Hz), 8.60 (1H, s), 10.02 (1H, s).

Subsequently, 4-imidazo[1,2-a]pyridin-2-ylbenzaldehyde g) was dissolved in tetrahydrofuran (100 mL), followed by stirring under ice cooling. Methyl magnesium bromide (3.0M diethyl ether solution, 4.4 mL) was added dropwise to the reaction mixture, followed by stirring at room temperature for 1 hour. Saturated aqueous ammonium chloride solution (5 mL) was added dropwise to the reaction mixture, followed by stirring at room temperature for 1 hour. Water was added to the reaction mixture, and the mixture was extracted with chloroform, followed by drying over magnesium sulfate. The solvent was evaporated, and the solid was recovered through filtration by use of dichloromethane-methanol (30:1) mixture. The filtrate was concentrated under reduced pressure, and the residue was subjected to flash chromatography. Fractions eluted by dichloromethane-methanol (30:1) were concentrated under reduced pressure, and the solid was recovered through filtration by use of diethyl ether. Through the above procedure, 1-(4-imidazo[1,2-a]pyridin-2-ylphenyl)-1-ethanol (2.43 g) was yielded.

$^1$H-NMR (400 MHz, DMSO-$d_6$) δ: 1.35 (3H, d, J=6.6 Hz), 4.75 (1H, dt, J=6.3, 10.7 Hz), 5.18 (1H, dd, J=1.2, 4.4 Hz), 6.89 (1H, dddd, J=1.2, 1.2, 6.8, 6.8 Hz), 7.24 (1H, dddd, J=1.2, 1.2, 6.6, 9.0 Hz), 7.41 (2H, d, J=8.3 Hz), 7.57 (1H, ddd, J=1.2, 1.2, 9.0 Hz), 7.91 (2H, d, J=8.3 Hz), 8.36 (1H, s), 8.52 (1H, dddd, J=1.2, 1.2, 1.2, 6.8 Hz).

Subsequently, manganese dioxide (4.35 g) was added to a solution of 1-(4-imidazo[1,2-a]pyridin-2-ylphenyl)-1-ethanol (2.38 g) in chloroform (100 mL), followed by refluxing under heating for 20 hours. Immediately after refluxing, the reaction mixture was filtered through Celite without being cooled, and the filtrate was concentrated under reduced pressure. The residue was subjected to silica gel chromatography, and fractions eluted by dichloromethane-methanol (100:1) were concentrated under reduced pressure. The solid was recovered through filtration by use of diethyl ether, to thereby yield 1-(4-imidazo[1,2-a]pyridin-2-ylphenyl)-1-ethanone (2.20 g).

$^1$H-NMR (400 MHz, DMSO-$d_6$) δ: 2.61 (3H, d, J=1.0 Hz), 6.93 (1H, dddd, J=1.0, 1.2, 6.8, 6.8 Hz), 7.29 (1H, dddd, J=1.0, 1.2, 6.8, 9.0 Hz), 7.61 (1H, d, J=9.0 Hz), 8.03 (2H, d, J=7.8 Hz), 8.12 (2H, d, J=7.8 Hz), 8.55 (1H, dd, J=1.2, 6.8 Hz), 8.56 (1H, s).

Subsequently, N,N-dimethylformamide dimethyl acetal (3.0 mL) was added to a solution of 1-(4-imidazo[1,2-a]pyridin-2-ylphenyl)-1-ethanone (2.13 g) in N,N-dimethylformamide (50 mL), followed by heating at 120° C. for 8 hours. The reaction mixture was cooled to room temperature, and the precipitated solid was recovered through filtration, followed by washing with ethanol. The filtrate was concentrated under reduced pressure. The thus-obtained solid and the residue were subjected to flash chromatography. Fractions eluted by dichloromethane-methanol (30:1) were concentrated under reduced pressure, and the solid was recovered through filtration by use of ethyl acetate. Through the above procedure, (E)-3-dimethylamino-1-(4-imidazo[1,2-a]pyridin-2-ylphenyl)-2-propen-1-one (2.38 g) was yielded.

$^1$H-NMR (400 MHz, DMSO-$d_6$) δ: 2.94 (3H, s), 3.16 (3H, s), 5.89 (1H, d, J=12.2 Hz), 6.91 (1H, dddd, J=1.0, 1.2, 6.8, 6.8 Hz), 7.26 (1H, dddd, J=1.0, 1.2, 6.8, 9.0 Hz), 7.60 (1H, d, J=9.0 Hz), 7.74 (1H, d, J=12.2 Hz), 7.97 (2H, d, J=8.3 Hz), 8.03 (2H, d, J=8.3 Hz), 8.49 (1H, s), 8.54 (1H, dd, J=1.2, 6.8 Hz).

Subsequently, hydrazine monohydrate (80%, 970 μL) was added to a solution of (E)-3-dimethylamino-1-(4-imidazo[1,2-a]pyridin-2-ylphenyl)-2-propen-1-one (2.33 g) in ethanol (40 mL), followed by refluxing under heating for 10 hours. The reaction mixture was left to cool, and the precipitated matter was recovered through filtration, followed by drying under reduced pressure, to thereby yield 2-[4-(1H-3-pyrazolyl)phenyl]imidazo[1,2-a]pyridine (1.91 g).

$^1$H-NMR (400 MHz, DMSO-$d_6$) δ: 6.72 (1H, d, J=2.0 Hz), 6.93 (1H, dt, J=1.0, 6.8 Hz), 7.33 (1H, ddd, J=1.2, 6.8, 9.0 Hz), 7.57 (1H, dd, J=1.0, 9.0 Hz), 7.68 (1H, brs), 7.85 (2H, d, J=8.3 Hz), 7.99 (2H, d, J=8.3 Hz), 8.24 (1H, s), 8.43 (1H, ddd, J=1.0, 1.2, 6.8 Hz).

Subsequently, under argon, sodium t-butoxide (481 mg) was added to a solution of 2-[4-(1H-3-pyrazolyl)phenyl]imidazo[1,2-a]pyridine (1.17 g) in anhydrous dioxane (50 mL), followed by stirring under ice cooling. A solution of chloroacetonitrile (316 μL) in anhydrous dioxane (5 mL) was added dropwise to the reaction mixture. The mixture was stirred at the same temperature for 15 minutes, followed by refluxing under heating for 45 hours. After the mixture had been left to cool, the reaction mixture was extracted with chloroform, followed by drying over magnesium sulfate. The solvent was evaporated under reduced pressure, and the residue was subjected to flash column chromatography. Fractions eluted by dichloromethane-methanol (50:1) were concentrated under reduced pressure, and the solid was recovered through filtration by use of diethyl ether, to thereby yield [3-(4-imidazo[1,2-a]pyridin-2-ylphenyl)-1H-1-pyrazolyl]methylcyanide (486 mg).

$^1$H-NMR (400 MHz, DMSO-$d_6$) δ: 5.56 (2H, s), 6.89 (1H, dd, J=1.2, 2.2 Hz), 6.91 (1H, tt, J=1.2, 6.8 Hz), 7.59 (1H, d, J=9.0 Hz), 7.90 (2H, d, J=8.3 Hz), 7.93 (1H, dd, J=1.2, 2.2 Hz), 8.03 (2H, d, J=8.3 Hz), 8.45 (1H, s), 8.54 (1H, ddd, J=1.2, 2.2, 6.8 Hz). ESI-MS m/z: 300 (M+H)$^+$.

Subsequently, [3-(4-imidazo[1,2-a]pyridin-2-ylphenyl)-1H-1-pyrazolyl]methylcyanide (479 mg) was suspended in ethanol (15 mL), and 25M aqueous sodium hydroxide solution (1.6 mL) was added to the suspension, followed by refluxing under heating for 14 hours. Water (20 mL) was added to the reaction mixture, and the mixture was left to cool. The pH of the reaction mixture was adjusted to about 3 with 3N hydrochloric acid. The precipitated solid was recovered through filtration, followed by washing with water and then drying under reduced pressure, to thereby yield 2-[3-(4-imidazo[1,2-a]pyridin-2-ylphenyl)-1H-1-pyrazolyl]acetic acid (489 mg).

$^1$H-NMR (400 MHz, DMSO-$d_6$) δ: 5.04 (2H, s), 6.88 (1H, d, J=2.2 Hz), 7.44 (1H, t, J=6.8 Hz), 7.84 (1H, d, J=2.2 Hz), 7.88 (1H, d, J=7.1 Hz), 7.94 (1H, d, J=8.6 Hz), 7.89 (2H, d,

J=8.3 Hz), 8.06 (2H, d, J=8.3 Hz), 8.82 (1H, s), 8.85 (1H, d, J=6.8 Hz), 12.90-13.50 (1H, br). ESI-MS m/z: 319 (M+H)$^+$.

Subsequently, 2-[3-(4-imidazo[1,2-a]pyridin-2-ylphenyl)-1H-1-pyrazolyl]acetic acid (255 mg), N1,N2-di{2-[(4-methoxybenzyl)sulfanyl]-2-methylpropyl}-1,2-ethanediamine (381 mg), and 1-hydroxybenzotriazole (135 mg) were dissolved in N,N-dimethylformamide (10 mL), and triethylamine (279 µL) and 1-ethyl-3-(3-dimethylaminopropyl)carbodiimide hydrochloride (192 mg) was added to the solution, followed by stirring at room temperature for 6 hours. Water was added to the reaction mixture, followed by extraction with dichloromethane and then drying over magnesium sulfate. The solvent was evaporated under reduced pressure, and the residue was subjected to flash column chromatography. Fractions eluted by dichloromethane-methanol (30:1) were concentrated under reduced pressure, to thereby yield N1-{2-[(4-methoxybenzyl)sulfanyl]-2-methylpropyl}-N1-[2-({2-[(4-methoxybenzyl)sulfanyl]-2-methylpropyl}amino)ethyl]-2-[3-(4-imidazo[1,2-a]pyridin-2-ylphenyl)-1H-1-pyrazolyl]acetamide (456 mg).

$^1$H-NMR (400 MHz, CD$_3$OD) δ: 1.32 (6H, s), 1.34 (6H, s), 2.56 (2H, s), 2.72 (2H, t, J=6.6 Hz), 3.57-3.85 (8H, m), 3.71 (6H, s), 5.30 (2H, s), 6.72 (1H, d, J=2.4 Hz), 6.78 (2H, d, J=8.6 Hz), 6.82 (2H, d, J=8.6 Hz), 6.91 (1H, dt, J=1.0, 6.8 Hz), 7.21 (2H, d, J=8.6 Hz), 7.24 (2H, d, J=8.6 Hz), 7.31 (1H, ddd, J=1.0, 2.4, 6.8 Hz), 7.56 (1H, d, J=9.0 Hz), 7.65 (1H, d, J=2.4 Hz), 7.87 (2H, d, J=8.5 Hz), 7.93 (2H, d, J=8.5 Hz), 8.20 (1H, s), 8.41 (1H, d, J=6.8 Hz).

ESI-MS m/z: 777 (M+H)$^+$.

Subsequently, N1-{2-[(4-methoxybenzyl)sulfanyl]-2-methylpropyl}-N1-[2-({2-[(4-methoxybenzyl)sulfanyl]-2-methylpropyl}amino)ethyl]-2-[3-(4-imidazo[1,2-a]pyridin-2-ylphenyl)-1H-1-pyrazolyl]acetamide (155 mg) was dissolved in trifluoroacetic acid (2 mL), followed by refluxing under heating for 4 hours. After the mixture had been left to cool, the mixture was concentrated under reduced pressure. Water was added to the residue, followed by washing with dichloromethane. The aqueous layer was concentrated under reduced pressure, to thereby yield the title compound (90 mg).

FAB-MS m/z: 537 (M+H)$^+$.

Example 35

N1,N1-Di(2-pyridylmethyl)-2-[3-(4-imidazo[1,2-a]pyridin-2-ylphenyl)-1H-1-pyrazolyl]acetamide 2-[3-(4-Imidazo[1,2-a]pyridin-2-ylphenyl)-1H-1-pyrazolyl]acetic acid (51 mg), 2,2'-dipicolylamine (32 mg), and 1-hydroxybenzotriazole (27 mg) were dissolved in N,N-dimethylformamide (1 mL), and triethylamine (56 µL) and 1-ethyl-3-(3-dimethylaminopropyl)carbodiimide hydrochloride (38 mg) were added to the solution, followed by stirring at room temperature for 2 hours. Water was added to the reaction mixture, followed by extraction with chloroform and then drying over magnesium sulfate. The solvent was evaporated under reduced pressure, and the residue was subjected to flash column chromatography. Fractions eluted by dichloromethane-methanol (20:1) were concentrated under reduced pressure, and the solid was recovered through filtration by use of diethyl ether, to thereby yield the title compound (58 mg).

$^1$H-NMR (400 MHz, DMSO-d$_6$) δ: 4.61 (2H, s), 4.87 (2H, s), 5.43 (2H, s), 6.78 (1H, dd, J=1.0, 2.4 Hz), 6.90 (1H, tt, J=1.0, 6.8 Hz), 7.23-7.29 (2H, m), 7.31 (1H, d, J=7.8 Hz), 7.37 (1H, ddt, J=1.0, 4.9, 6.8 Hz), 7.43 (1H, d, J=7.8 Hz), 7.58 (1H, d, J=9.0 Hz), 7.74 (1H, ddt, J=1.0, 1.7, 7.8 Hz), 7.79 (1H, dd, J=1.0, 2.4 Hz), 7.83 (1H, ddt, J=1.0, 1.7, 7.8 Hz), 7.86 (2H, d, J=8.3 Hz), 8.00 (2H, d, J=8.3 Hz), 8.45 (1H, s), 8.50 (1H, ddd, J=1.0, 1.0, 4.9 Hz), 8.53 (1H, dd, J=1.0, 6.8 Hz), 8.65 (1H, ddd, J=1.0, 1.0, 4.9 Hz).

ESI-MS m/z: 500 (M+H)$^+$.

Example 36

Method for producing [$^{123}$I]6-iodo-2-[4-(1H-3-pyrazolyl)phenyl]imidazo[1,2-a]pyridine injection liquid Sodium iodide (3.75 µg) was dissolved in 0.3-mol/L phosphate-sodium buffer (pH 5.5) (1,167 µL). To the solution, sodium iodide ($^{123}$I) solution (radioactivity concentration at the examination time: 12.33 GBq/mL) (500 µL), 1 mg/mL solution of the Example 25 compound in 2-propanol (333 µL), and 0.1 mg/mL aqueous chloramine T solution (333 µL) were added. The mixture was allowed to react at room temperature for five minutes. After completion of reaction, ethanol (1,667 µL) and hydrochloric acid (833 µL) were added to the reaction mixture. The product was placed in a reaction glass vial, which was closed with a rubber stopper and an aluminum stopper. The glass vial was placed on a heating block (70° C.) for 30 minutes for performing deprotection. After completion of deprotection, the stoppers were removed, and 12-mol/L aqueous sodium hydroxide solution (750 µL) and aqueous saturated sodium hydrogencarbonate solution (2,499 µL) were added in order to neutralize the reaction mixture, followed by further adding injection water (8,000 µL) thereto. The entirety of the resultant liquid was caused to pass through a solid-phase extraction column (Empore C18 HD, 3M), which had been activated in advance with anhydrous ethanol (5 mL) and injection water (5 mL), under reduced pressure (100 Torr). Similarly, the entirety of wash liquid (obtained through washing the reaction glass vial with injection water (5 mL)) was caused to pass through the same column under reduced pressure (100 Torr). Furthermore, injection water (5 mL) was also caused to pass through the same column under reduced pressure (100 Torr). Anhydrous ethanol (0.5 mL) and injection water (0.5 mL) were passed through the solid-phase extraction column under reduced pressure (500 Torr), whereby the title compound was recovered through extraction. Subsequently, the extract obtained through the solid-phase extraction column was injected to an HPLC, to thereby purify under the following conditions [mobile phase; line A: ethanol, line B: distilled water, A:B=50:50, flow rate: 2 mL/min, column temperature: 30° C., UV wavelength at measurement: 275 nm, and column: CAPCELL PAK C18 UG 120.5 µm].

After starting of injection, a fraction corresponding to an elution time range of about 18 minutes to about 22 minutes was collected over four minutes. To a fraction glass vial, 500-mmol/L aqueous ascorbic acid solution (50 µL) had been added in advance. Injection water (32 mL) was added to the HPLC fraction, and the entirety of the liquid was caused to pass through a solid-phase extraction column (Empore C18 HD, 3M), which had been activated in advance with anhydrous ethanol (5 mL) and injection water (5 mL), under reduced pressure (100 Torr). Similarly, the entirety of wash liquid (obtained through washing the reaction glass vial with injection water (5 mL)) was caused to pass through the same column under reduced pressure (100 Torr). Furthermore, injection water (5 mL) was also caused to pass through the same column under reduced pressure (100 Torr). Anhydrous ethanol (1 mL) was passed through the solid-phase extraction column under reduced pressure (500 Torr), whereby the title compound was recovered through extraction. Anhydrous ethanol (1 mL) was added to the extract, and an aliquot (180

µL) was collected, to which 500-mmol/L aqueous ascorbic acid solution (20 µL) was added. To the entirety of the liquid, 40-mmol/L ascorbic acid/0.1% Polysolvate 80 in physiological saline (3,800 µL) was added, to thereby prepare a standard compound injection liquid (radioactivity concentration at the examination time: 6477.2 Ci/mmol).

Referential Example 31

Method for Producing [$^{123}$I]6-iodo-2-(4'-dimethylamino-)phenyl-imidazo[1,2-a]pyridine ($^{123}$I-IMPY) Injection Liquid To a solution (150 µL) of 6-tributylstannyl-2-(4'-dimethylamino-)phenyl-imidazo[1,2a]pyridine in ethanol (concentration: adjusted to 1 mg/mL), sodium iodide ($^{123}$I) solution (radioactivity concentration at the examination time: 13.50 GBq/mL) (90 µL) and 1-mol/L aqueous hydrochloric acid solution/1% (w/v) aqueous hydrogen peroxide (10:3) mixture (195 µL) were added, and the mixture was allowed to react at room temperature for 60 minutes. The reaction was terminated by adding 100 mg/mL aqueous sodium hydrogensulfite solution (60 µL), and 1-mol/L aqueous sodium hydroxide solution (150 µL) and saturated sodium hydrogencarbonate solution (150 µL) were added in order to neutralize the reaction mixture. The neutralized reaction mixture was injected to an HPLC so as to purify under the following conditions [mobile phase; line A: ethanol, line B: 10-mmol/L aqueous disodium hydrogenphosphate solution, A:B=50:50, flow rate: 2 mL/min, column temperature: 30° C., UV wavelength at measurement: 280 nm, and column: CAPCELL PAK C18 UG 120, 10×250 mm, 5 µm].

After starting of injection, a fraction corresponding to an elution time range of about 11 minutes to about 12 minutes was collected. To a fraction glass vial, 500-mmol/L aqueous ascorbic acid solution (5 µL) was added in advance. Injection water (8 mL) was added to the HPLC fraction, and the entirety of the liquid was caused to pass through a solid-phase extraction column (Sep-Pak Light C18), which had been activated in advance with anhydrous ethanol (5 mL) and injection water (5 mL), under reduced pressure (100 Torr). Furthermore, injection water (5 mL) was also caused to pass through the same column under reduced pressure (100 Torr). Anhydrous ethanol (2.5 mL) was passed through the solid-phase extraction column under reduced pressure (500 Torr), whereby the title compound was recovered through extraction. To the extraction flask, 500-mmol/L aqueous ascorbic acid solution (5 µL) had been added in advance. The solvent was removed under reduced pressure, and the residue was dissolved in ethanol (0.2 mL). To the solution, 40-mmol/L ascorbic acid/ 0.1% Polysolvate 80 in physiological saline (3.8 mL) was added, followed by mixing. In order to attain a target radioactivity concentration at the examination time, ethanol (0.1 mL) and 40-mmol/L ascorbic acid/0.1% Polysolvate 80 in physiological saline (1.9 mL) were added, and the liquid (3 mL) was filtered by means of Millex-LG. The filtrate was employed as a title compound injection liquid (radioactivity concentration at the examination time: 236073.3 Ci/mmol).

In the following Test Examples, the reference numeral of a compound corresponds to the Example number. For example, the compound of Example 3 is referred to as "compound 3."

Test Example 1

Measurement of Liposolubility

In imaging by use of a radio-labeled derivative, liposolubility thereof is an important factor, and affects image contrast. Liposolubility (log $D_{o/w}$) at pH 7.4 was determined in accordance with a method employing high-performance liquid chromatograph (HPLC) equipped with a reverse phase column. Compounds shown in Table 1 have a known log $D_{o/w}$, and were employed as liposolubility standard substances. Through comparison with liposolubility standard substances, the log $D_{o/w}$ values of the compounds of the invention were calculated.

Each compound of the invention was dissolved in 60% methanol, to thereby prepare a 20-µmol/L sample solution. A liposolubility standard substance having a concentration of 20-µmol/L was also prepared in a similar manner.

The employed HPLC was a separation module Alliance 2690 connected to a 2487 Dual λ UV-detector, and detection was performed at a detection wavelength of 256 or 300 nm. Obtained data were analyzed by means of a Millennium 32 (these products are of Waters Corporation). A Symmetry C18, 3.9×150 mm column (product of Waters Corporation) was employed, and analysis was performed at a mobile phase flow rate of 1.0 mL/min. The employed mobile phase was a mixture of 20 mM 4-morpholine-propanesulfonate (MOPS) buffer (pH 7.4) and methanol of one of five proportions (40: 60 to 15:85). At each proportion, the retention time of a standard solution and that of a sample solution were calculated through the following formula.

The capacity factor (k') at each methanol concentration was calculated as follows.

$$k'=(t_R-t_O)/t_O \quad (F1)$$

k': Capacity factor
$t_R$: Retention time of sample
$t_O$: Column passage time of mobile phase The logarithmic values of the capacity factor at respective methanol concentrations were extrapolated to a methanol concentration of 0%, and the value obtained through extrapolation was employed as the log kw. On the basis of the relationship between log kw (measured) of a standard substance having a known log $D_{7.4}$ and log kw (reported in the literature), the log $D_{7.4}$ value of the test substance was calculated from the log kw value (measured).

FIG. 1 shows the correlation of log kw values of the liposolubility standard substance and log $D_{74}$ values thereof.

Table 2 shows liposolubility values of the compounds of the invention obtained from the correlating equation given in FIG. 1.

As is clear from FIG. 1 and Table 2, the compounds of the invention have an optimum liposolubility for allowing passage through the blood-brain barrier, and thus were found to be a class of compounds suitable for imaging.

TABLE 1

| Standard substances of liposolubility and liposolubility values reported in the literature | |
|---|---|
| Standard substances | LogD$_{7.4}$ |
| Acetaminophen | 0.51 |
| Allopurinol | −0.44 |
| Antipyrin | 0.38 |
| Bifonazole | 4.77 |
| Caffein | −0.07 |
| Chloramphenicol | 1.55 |
| Chlorpheniramine | 1.41 |
| Cimetidine | 0.35 |
| Clonidine | 0.62 |
| Clozapine | 3.13 |
| Haloperidol | 2.98 |
| Hydrocortisone | 1.55 |

TABLE 1-continued

Standard substances of liposolubility
and liposolubility values
reported in the literature

| Standard substances | LogD$_{7.4}$ |
|---|---|
| Naphtalene | 3.37 |
| Predonisolone | 1.60 |
| Risperidon | 2.04 |
| Teststeron | 3.29 |
| Triphenylene | 5.49 |
| Walfarine | 1.12 |
| β-estradiol | 4.01 |

Test Example 2

Inhibition of Binding to Amyloid β Protein Aggregates

Synthetic A β peptides in a solution form undergo spontaneous aggregation in a test tube, to thereby form aggregates having the same β-sheet structure as that of amyloid aggregates present in a brain suffering from Alzheimer's disease (hereinafter, such a brain is referred to as an "Alzheimer brain"). Thus, inhibitory activity on binding to amyloid β protein aggregates was determined by use of a $^{125}$I-labeled product of compound I (compound 23) as a sample, whereby the screening method for the compounds of the invention was carried out.

Specifically, amyloid β (1-40) peptide hydrochloric acid salt (product of PEPTIDE INSTITUTE, INC.) was dissolved in purified water so as to adjust the concentration to 200 mol/L. An equiamount of phosphate buffered saline (PBS(−)) of 2-fold concentration was added to the solution, followed by ultrasonication. After ultrasonication, the mixture was gently stirred at 37° C. for four days, to thereby produce synthetic amyloid β (1-40) aggregates.

Binding test was performed in the following manner. Firstly, PBS (500 μL) and 0.2% BSA/PBS solution (100 μL) were added to test tubes. A test substance was dissolved in an ascorbic acid solution (20% ethanol-containing 5 mmol/L ascorbic acid/PBS solution) and successively diluted, so as to establish a series of concentrations ranging from 0.038 (final) to 10,000 nmol/L. Each solution (100 μL) was added to the test tube, and 1-nmol/L compound 23 (100 μL) and ascorbic acid solution (100 μL) (1 mL at reaction) were added to the test tube. Reaction was initiated by adding a synthetic amyloid β (1-40) aggregates solution (concentration: 500 nmol/L, adjusted by PBS) (200 μL) to each test tube. Non-specific binding was estimated by adding a solution of compound 1 (concentration: 5 μmol/L, diluted by ascorbic acid solution) to a test tube instead of ascorbic acid solution (100 μL) (final concentration: 500 nmol/L).

These samples were incubated at room temperature for three hours, and each reaction mixture was filtered by means of a cell harvester (M-24R, product of Brandel) by use of a Whatman GF/B filter (product of Whatman). The filter was washed thrice with ice-cooled PBS solution (about 2 mL) containing 0.1-mmol/L ascorbic acid. An area where compound 23 had been captured was cut out, and radioactivity of the area was measured by means of a gamma-counter (product of Wallac).

Activity values were calculated by means of a GraphPad Prism Ver. 4.00 (product of GraphPad Software, Inc.) as a concentration at which inhibition to 50% can be attained (IC$_{50}$), wherein the count measured from a sample to which only ascorbic acid solution had been added was 100%. Table 2 shows the results.

TABLE 2

Inhibitory activity on binding to A β 1-40 aggregates and liposolubility

| Ref. compd. or Example No. | Inhibitory activity (n = 3) IC50 Mean ± S.D. nmol/L | Liposolubility LogD$_{7.4}$ |
|---|---|---|
| IMPY | 29.3 ± 12.8 | 4.03 |
| PIB | 42.9 ± 5.88 | 2.54 |
| FDDNP | 1050 ± 48.8 | 3.00 |
| Thioflavin T | 895 ± 121 | — |
| Congo Red | >5000 | — |
| 1 | 1.23 ± 0.0842 | 3.64 |
| 3 | 9.72 ± 1.44 | 3.20 |

Generally, amyloid aggregates each have several binding sites. Since binding of compound 23 to amyloid aggregates is more effectively inhibited by IMPY and PIB, having a structure similar to that of thioflavin T, and less effectively inhibited by Congo red and FDDNP, binding sites of amyloid aggregates with respect to compound 23 are conceivably the same as those with respect to IMPY and PIB.

The compounds of the present invention more strongly inhibit binding to β amyloid, as compared with known compounds such as IMPY and PIB, which are known to have inhibitory activity on binding to β amyloid, which forms senile plaques in Alzheimer's disease patients. Thus, the compounds of the present invention were found to have more strong binding activity to amyloid aggregates.

Test Example 3

Inhibitory Activity on Formation of Amyloid from Amyloid β Protein

Amyloid β (1-40) peptide hydrochloric acid salt (product of PEPTIDE INSTITUTE, INC.) (15 μmol/L) and a test substance (1.6, 8, or 40 μmol/L) were incubated in PBS(−) at room temperature for one day. Thereafter, the amount of formed amyloid was measured through the thioflavin T method. The measurements were reduced to relative values (%) with respect to the amyloid formation amount obtained from a control group (no test substance had been added), and 50%-amyloid-formation-inhibition concentrations (IC$_{50}$ values) were calculated. Similarly, the same procedure was repeated by use of amylin protein (product of Bachem) (10 μmol/L), and IC$_{50}$ values were calculated. Table 3 shows the results. As is clear from table 3, aggregation of amyloid β (1-40) can be prevented by the compound of the present invention.

TABLE 3

Amyloid β protein aggregation inhibitory activity

| Example No. | Aggregation inhibitory activity IC50 A β 1-40 μmol/L |
|---|---|
| 1 | 29.4 |
| 3 | 22.3 |

Test Example 4

Binding Experiment to Amyloid β Protein Aggregates

In order to confirm that specific binding of the compound of the present invention is promoted in accordance with the amount of amyloid aggregates and that the specific binding is not affected by a certain component in the brain, binding experiments were performed between amyloid β protein aggregates and a $^{123}$I-labeled product of compound 3 or $^{123}$I-IMPY, in the presence or absence of a normal rat brain homogenate.

Through a similar technique as employed in Test Example 2, synthetic amyloid β (1-40) aggregates were produced, and dissolved in PBS to a concentration of 500 nmol/L. From the solution, solutions of a twice-diluted series with PBS were prepared.

A brain tissue was removed from a normal rat, and a 5-fold amount of PBS was added to the tissue (wet state). A homogenate was produced from the mixture by use of a homogenizer. To test tubes, PBS (500 µL, in the presence of homogenate or 600 µL, in the absence of homogenate) was added. A rat brain homogenate (100 µL) was added under the presence condition of homogenate. To each test tube, an $^{123}$I-labeled product (1.1 µCi/mL, 100 µL) and ascorbic acid solution (100 µL) (1 mL at reaction) were added. Each (200 µL) of the Aβ aggregates solutions of twice-diluted series was added to each test tube, whereby reaction was initiated. Non-specific binding was estimated by adding a solution of compound 1 (concentration: 5 µmol/L, diluted with ascorbic acid solution to a test tube instead of ascorbic acid solution (100 µL) (final concentration: 500 nmol/L).

Thereafter, through a similar technique as employed in Test Example 2, filtration was performed by use of a filter, and radioactivity of a labeled substance trapped by the filter was counted.

Figure 2:
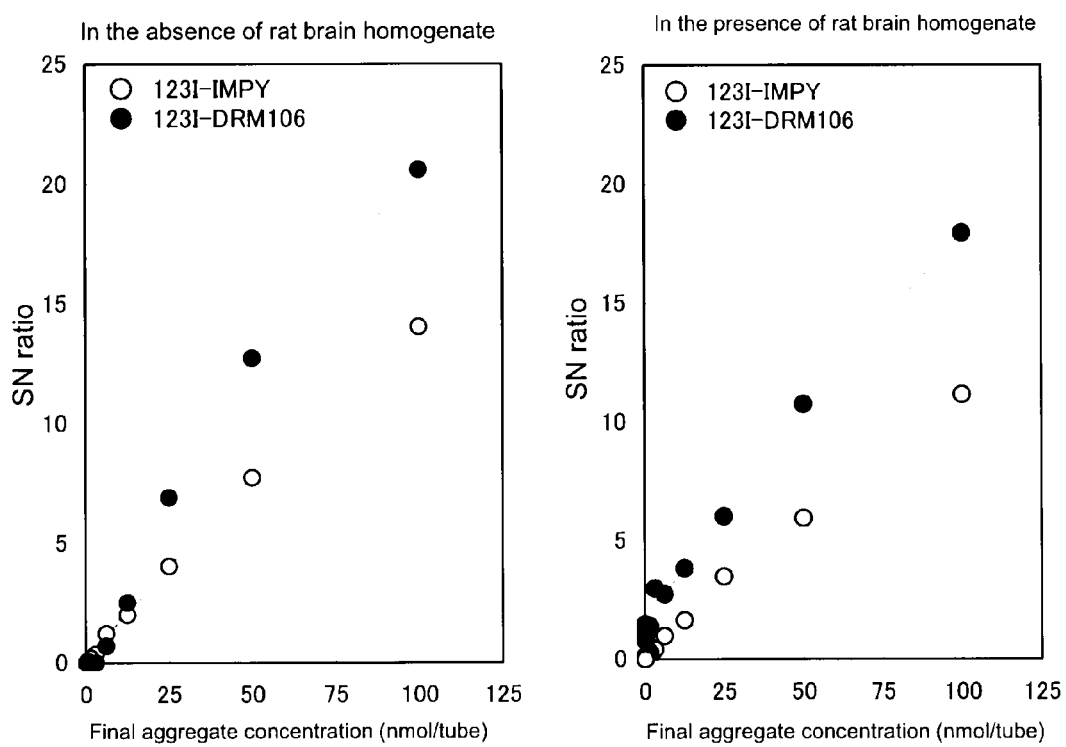
FIG. 2 Graphs showing the relationship between amyloid P (1-40) aggregate amount and SN ratio (left: in the absence of normal rat brain homogenate) and (right: in the presence of normal rat brain homogenate)

By subtracting a non-specific binding amount from the total binding amount and dividing the difference by the non-specific binding amount, an SN (Signal/Noise) ratio was calculated. The relationship between the SN ratio and amyloid β protein aggregate concentration was investigated (FIG. 2).

Both the $^{123}$I-labeled product of compound 3 and $^{123}$I-IMPY exhibited an increase in bonding amount in response to the amyloid β protein aggregate concentration. Since this phenomenon was observed both in the presence and absence of a normal rat homogenate, no normal brain component affected the binding, the bonding was promoted in response to the amyloid β protein aggregate concentration. As the $^{123}$I-labeled product of compound 3 exhibited high binding activity in Test Example 2, the compound exhibited a higher SN ratio.

Test Example 5

Analysis of Secondary Structure of Amyloid β Protein Aggregates

Secondary structure of amyloid β protein aggregates was analyzed through measurement of circular dichroism (CD).

In a manner similar to that of Test Example 2, synthetic amyloid β (1-40) aggregates were produced, and the concentration thereof was adjusted to 500 nmol/L by use of PBS. Separately, amyloid β (1-40) peptide HCl salt was dissolved in purified water, to thereby prepare a 100-µmol/L amyloid β (1-40) solution. A CD spectrum of each sample solution (twice diluted) was measured at room temperature (about 25° C.) in a wavelength range of 190 to 250 nm. PBS or purified water was measured as a blank. After measurement, a blank value was subtracted from a CD value of each sample, to thereby correct the base line. From the thus-corrected CD values, secondary structure analysis was performed by means of SELCON3.

Figure 3:
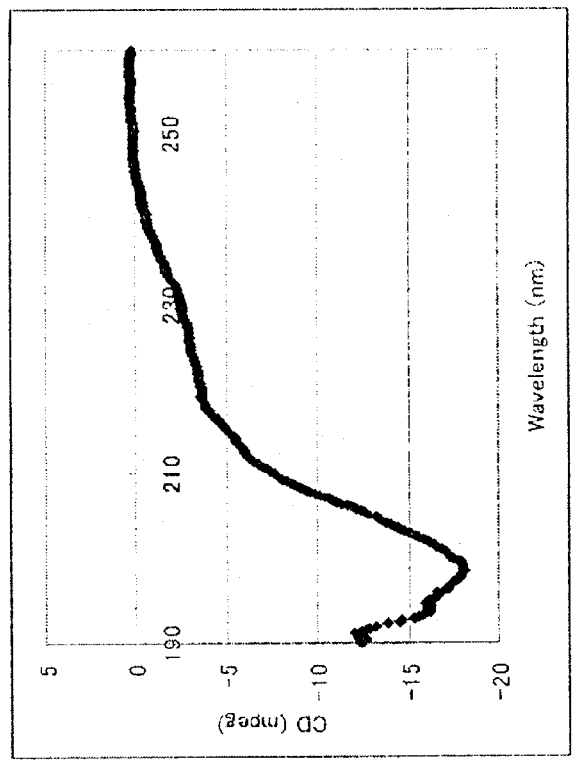
FIG. 3 CD spectrum charts of amyloid β (1-40) aggregate suspension and aqueous amyloid β (1-40) solution.
Figure 3:
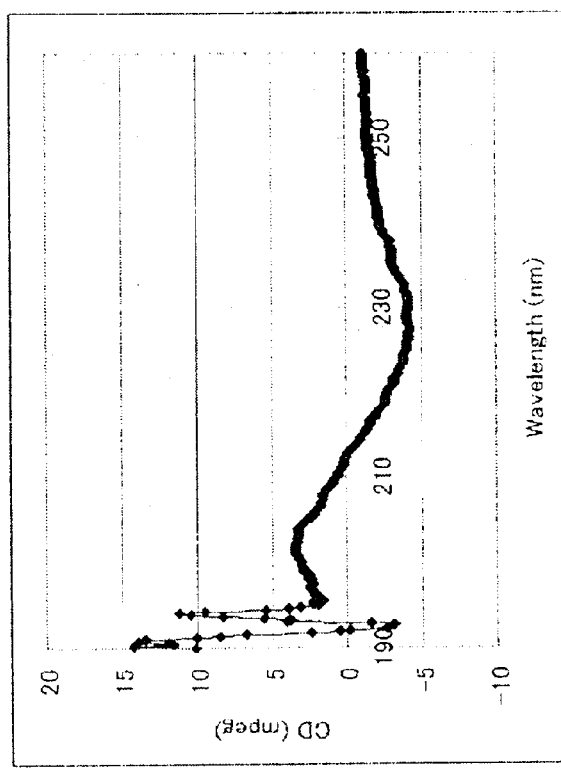

FIG. 3 shows a CD spectrum of an amyloid β (1-40) aggregate suspension and of amyloid β (1-40) peptide solution. The CD spectra were analyzed by means of an analysis software SELCON3 for secondary structure analysis (Table 4). Through the secondary structure analysis, β-sheet structure was found to increase during the course of aggregation in PBS.

TABLE 4

|  | Secondary structure proportion(%) | | | |
| --- | --- | --- | --- | --- |
|  | α-helix | β-sheet | Turn | Others |
| Suspension of amyloid β (1-40) aggregated in PBS | 12.2 | 31.3 | 13.2 | 43.3 |
| Solution of amyloid β (1-40) dissolved in purified water | 5.4 | 4.3 | 20.2 | 70.1 |

Subsequently, binding ability of the compound of the invention to amyloid β (1-40) peptide dissolved in purified water or aggregated in PBS was determined in a manner similar to that employed in Test Example 3. However, a $^{125}$I-labeled compound 24 was employed, and no rat bran homogenate was included. The employed amyloid β concentration was 50 nmol/L at reaction.

TABLE 5

|  | Specific binding radioactivity (cpm) |
| --- | --- |
| Suspension of amyloid β (1-40) aggregated in PBS | 125504.4 |
| Solution of amyloid β (1-40) dissolved in purified water | 6300.3 |

Specific binding of compound 24 to amyloid β (1-40) aggregates (suspension) formed in PBS was found to be about 20 times stronger than that to amyloid β (1-40) dissolved in purified water (solution). Therefore, compound 24 is conceived to bind to amyloid β aggregates having abundant β-sheet structure.

Test Example 6

Confirmation of Correlation of β Sheet Amount in Aggregates to Binding Amount of Compound 23

In order to confirm that binding of compound 23 is promoted in accordance with the β-sheet structure amount, binding amount was compared among amyloid β aggregates having different β-sheet contents.

It has already reported by Wood et al. that amyloid β (1-40) aggregated in an acidic medium assumes large aggregates having a small β-sheet structure content, and that the structure is unchanged even in a neutral pH medium (Wood S. J., J. Mol. Biol. 256(5): 870-877). According to this report, synthetic amyloid β (1-40) aggregates were prepared in PBS in a manner similar to that of Test Example 2, and such aggregates were also prepared in MES (2-morpholinoethansulfonate) buffer in a similar manner.

Upon experiment, these aggregate solutions were mixed such that the ratio of PBS aggregates to MES aggregates were adjusted to 3:1, 1:1, and 1:3 (PBS aggregates content: 75, 50, and 25%). These samples were further diluted with PBS to 40 µmol/L. Also a PBS aggregates sample and a MES aggregates sample were diluted with PBS to 40 µmol/L respectively.

The β-sheet content of aggregate mixture samples was determined through the thioflavin T method. Specifically, 40-µmol/L each aggregate solution (48.75 µL) and 2-mmol/L thioflavin T solution (1.25 µL) were added to a 96-well black half-area well plate (product of NUNC), and fluorescence intensity at a wavelength of 490 nm (excitation at 443 nm) was measured by means of a microplate reader (product of MOLECULAR DEVICES).

The binding amount of compound 23 to an aggregate mixture (aggregates formed in PBS and those formed in MES) was determined in a manner similar to that of Test Example 5 (binding to amyloid).

Figure 4:
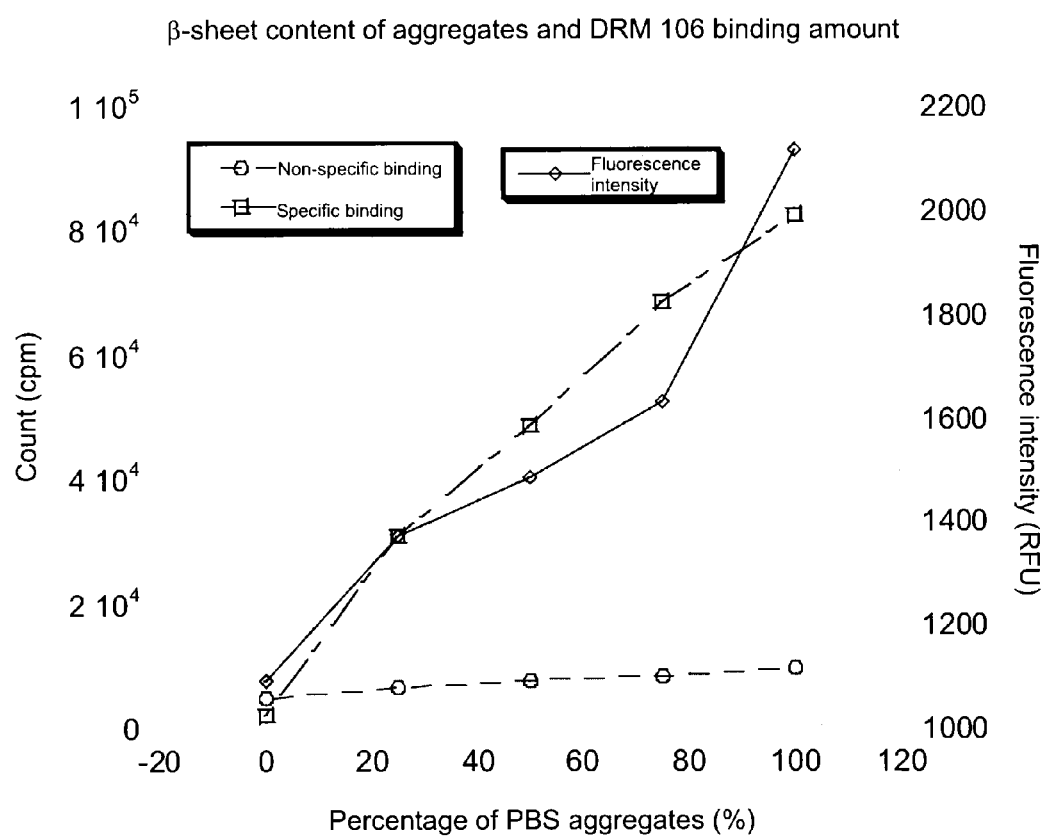
FIG. 4 A graph showing comparison β-sheet content of amyloid β(1-40) aggregate with binding amount of compound 24.

FIG. 4 is a graph showing the specific binding amount of compound 23 to an aggregate mixture and the non-specific binding amount thereof, together with the corresponding fluorescence intensity of the aggregate mixture. The fluorescence intensity of an aggregate mixture increased in response to an increase in amount of PBS aggregates having a large β-sheet structure content. The specific binding amount of compound 24 exhibited the same tendency. Therefore, specific binding of compound 23 was found to be promoted in accordance with an increase in β-sheet content, and binding of the compound to amyloid β aggregates was found to depend on β-sheet structure.

Test Example 7

Calculation of Binding Affinity by Use of Alzheimer Brain

Obtaining Alzheimer Brain

Whole protein of human Alzheimer lesion origin (temporal cortex), a commercial product of Biochain (US), was employed.

Binding experiment method: The binding experiment was performed in a manner similar to that of Test Example 2. A test compound was dissolved in and diluted with a 200-mmol/L ascorbic acid/PBS solution containing 20% ethanol, to thereby adjust the concentration in a reaction test tube to a 4-fold dilution series of 0.00019 nM to 200 nM. The $^{125}$I-labeled test compound concentration was adjusted with ascorbic acid solution to 0.5 nmol/L in a test tube. An Alzheimer brain homogenate diluted with PBS was added to each test tube, to thereby initiate reaction. Non-specific binding was estimated through performing a similar procedure in which compound 1 was added to adjust a concentration of 200 nmol/L in a test tube, and counting radioactivity.

Since the test substance and the $^{125}$I-labeled test substance has the same structure, both species are conceivably bound to amyloid aggregates in the same binding fashion. Therefore, the count data were corrected provided that the non-labeled test substance is regarded as the $^{125}$I-labeled test substance, and the corrected data were analyzed by means of GraphPad Prism Ver. 4.00 (GraphPad Software, Inc.), to thereby calculate binding parameters (Kd, Bmax). Table 6 shows the results.

As is clear from Table 6, the compound of the invention exhibited higher binding activity to the Alzheimer brain, as compared with a known compound $^{125}$I-IMPY.

TABLE 6

Binding affinity to Alzheimer brain

| Compound. No. or Reference compound | Kd nmol/L | Bmax pmol/mg protein |
|---|---|---|
| Compd. 23 ($^{125}$I-labeled compd. 1) | 1.86 | 1.66 |
| Compd. 24 ($^{125}$I-labeled compd. 3) | 4.05 | 1.59 |
| $^{125}$I-IMPY | 4.58 | 1.99 |

Test Example 8

In Vitro Specific Binding Experiment by Use of Alzheimer Brain

Whole protein of human Alzheimer lesion origin (temporal lobe), a commercial product of Biochain (US), was employed.

Figure 6:
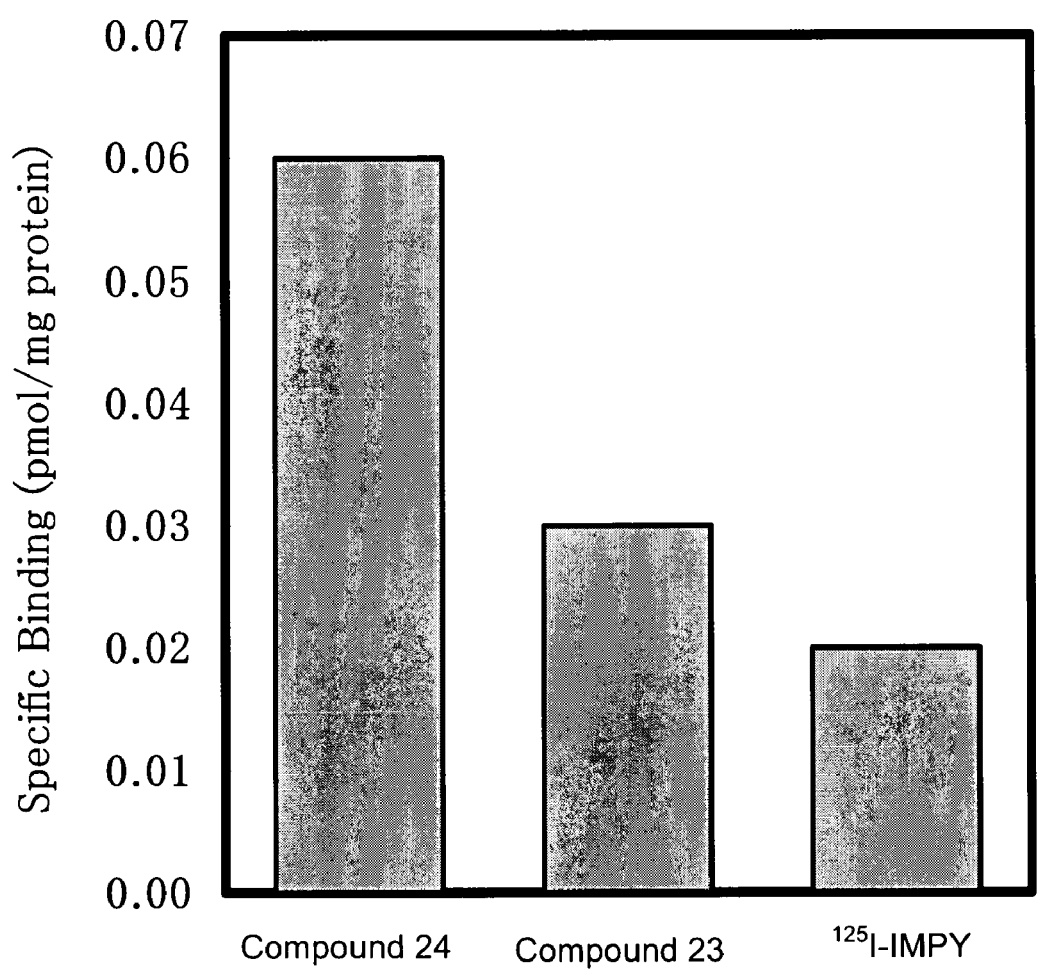
FIG. 6 A graph showing the experimental results of in vitro specific binding by use of Alzheimer brain.

Binding experiment method: The $^{125}$I-labeled test compound concentration was adjusted with the aforementioned ascorbic acid solution to 0.5 nmol/L in a reaction test tube. To the test tube, a whole protein sample of the Alzheimer lesion origin diluted with PBS was added to each test tube such that the concentration in the test tube was adjusted to 50 µg-protein/L, to thereby initiate reaction. After reaction at room temperature for 10 minutes, the reaction was terminated through filtration by means of suction, which is similar to the procedure of the aforementioned test method. Non-specific binding was estimated through performing a similar procedure in which compound 1 was added to adjust a concentration of 200 nmol/L in a test tube. FIG. 6 shows the results.

As is clear from FIG. 6, the compound of the present invention exhibited a large specific binding amount to the Alzheimer brain even in short-term incubation, and a higher binding rate, as compared with a known compound $^{125}$I-IMPY. These properties are advantageous for radioactive drugs, which must be incorporated into the brain within a short period of time after administration to the body, and must be rapidly discharged.

Test Example 9

Distribution in Rat Body

Wistar male rats (purchased from Japan SLC, Inc.) were conditioned for seven days, maintaining water and chow (commercial solid chow: F-2, product of Funabashi Farm) ad libitum, and the non-fasting rats were employed in the experiment (8-week-old at experiment).

Each of compound 23, compound 24, and [$^{125}$I]-IMPY was dissolved in a solution containing 40 mM ascorbic acid and 0.1% Tween80, to thereby adjust the concentration to 100 µCi/200 µL. Each sample was administered to each rat through the caudal vein under non-anesthetization. After administration, the rats were decapitated at minute 2, 5, 10, 20, 40, 60, or 120, under anesthetization with halothane, and the brain and blood were immediately collected from each rat.

The brain was cut into the left and right parts, and each part was weighed. The right brain was placed in a vial, and radioactivity was measured by means of a gamma counter. The radioactivity relative to the administration amount was calculated. Specifically, radioactivity of the tissue and that divided by the tissue weight were calculated as % I.D. and % I.D./g-tissue weight, respectively.

Table 7 shows change over time in radioactivity in the brain. All the labeled derivatives exhibited excellent incorporation to the rat brain and rapid clearance thereafter. Since these labeled compounds exhibit such behavior in the normal brain including no amyloid aggregates, when administered to an Alzheimer's disease patient, a radioactive ligand binds to amyloid and remains in the brain, but the radioactive ligand is rapidly cleared in a portion where no amyloid depositions are present. Therefore, a high-contrast amyloid distribution image can be obtained in a short period of time.

TABLE 7

Change over time in radioactivity in the rat brain after administration

| Time after administration (min) | $^{125}$I-IMPY Mean ± SD (% I.D./g) | Compound 23 ($^{125}$I-labeled compound 1) Mean ± SD (% I.D./g) | Compound 24 ($^{125}$I-labeled compound 3) Mean ± SD (% I.D./g) |
|---|---|---|---|
| 2 | 1.110 ± 0.027 | 1.268 ± 0.166 | 0.760 ± 0.036 |
| 5 | 0.713 ± 0.098 | 1.124 ± 0.032 | 0.656 ± 0.026 |
| 15 | 0.337 ± 0.019 | 0.584 ± 0.077 | 0.373 ± 0.047 |
| 30 | 0.144 ± 0.021 | 0.273 ± 0.015 | 0.176 ± 0.009 |
| 60 | 0.065 ± 0.002 | 0.139 ± 0.006 | 0.053 ± 0.003 |
| 120 | 0.027 ± 0.001 | 0.083 ± 0.002 | 0.015 ± 0.002 |

Test Example 10

Analysis of Radioactive Substance in the Rat Brain after Administration

Compounds which had been incorporated into the rat brain were investigated. The left part of the rat brain, obtained in the above experiment (distribution in the rat body) was homogenized by means of a Potter-type homogenizer with 40-mmol/L ascorbic acid-containing PBS (4-fold amount by mass). Acetonitrile (4-fold volume with respect to homogenate) was added to the homogenate, and the mixture was filtered, to thereby remove protein. The acetonitrile layer was developed by means of a reverse phase TLC (Whatman KC18F). The TLC was brought into contact with an imaging plate, and radioactivity was detected by means of BAS-1800 (product of Fuji Film Co., Ltd.). Each of the brain homogenate obtained 2, 5, 40, 60, and 120 minutes after administration was treated with acetonitrile so as to remove protein, and extracted radioactive substances were analyzed through thin-layer chromatography (KC18F, Whatman).

Figure 5:
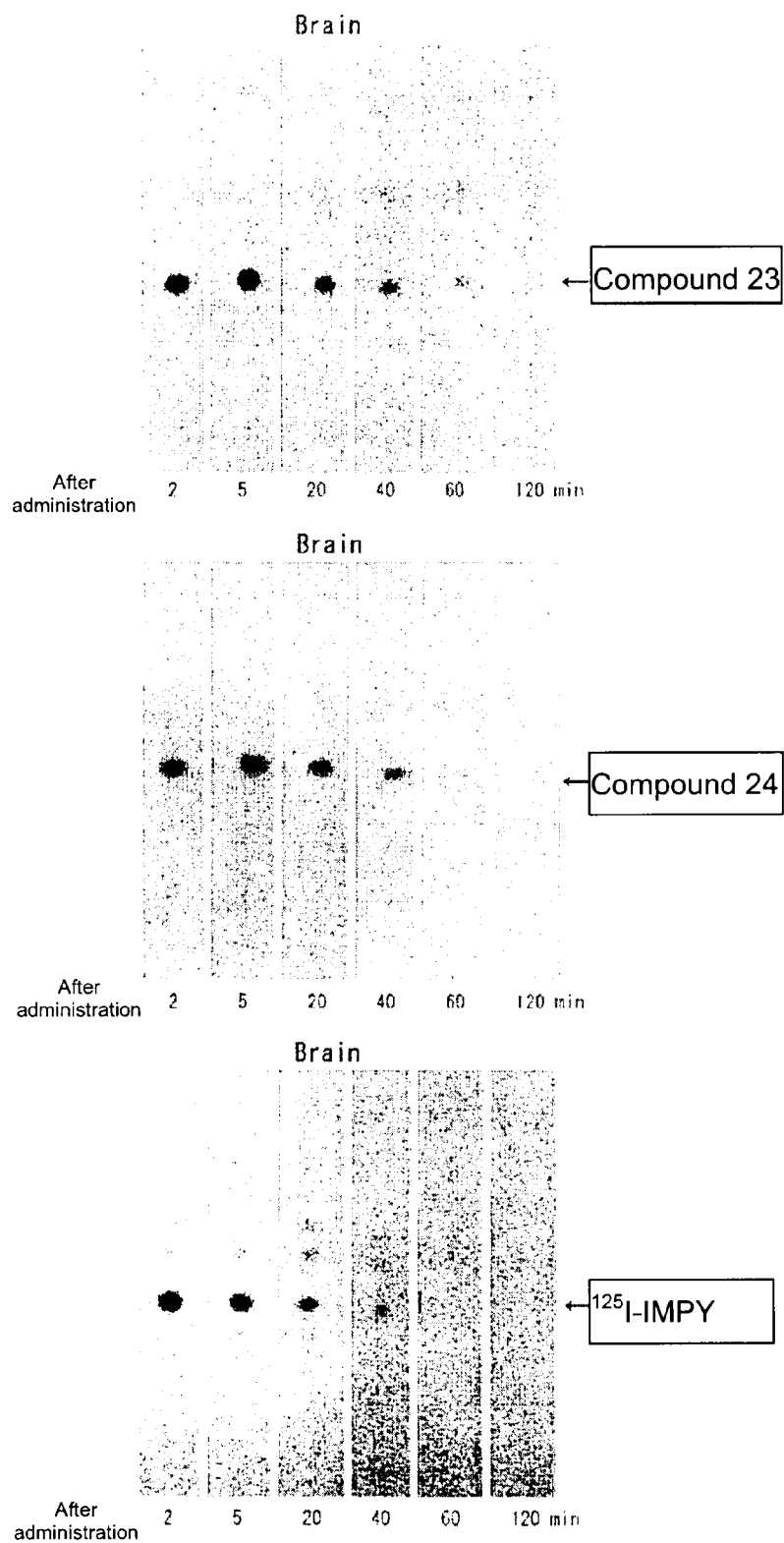
FIG. 5 Results of radioactive substance analysis in the brain of rat after administration.

FIG. 5 shows TLC analysis results of extracted radioactive substance, which has been accumulated in the brain. The compounds of the present invention did not provide observable metabolites in the brain, and were virtually unchanged. In contrast, $^{125}$I-IMPY provided a plurality of metabolites in the brain, and these metabolites increased over time after administration.

Test Example 11

Calculation of In Vitro Metabolism Rate by Use of Liver Microsomes

Obtaining Liver Microsomes

Liver microsomes (Pooled human Liver Microsomes, Male CD1 mouse, Male Wistar Rat), which is a commercial product of In Vitro Technologies, were employed.

Preparation of [$^{125}$I]-Labeled Compounds

Each of compound 23, compound 24, and [$^{125}$I]-IMPY was dissolved in Milli Q water, to thereby adjust the concentration to 11 μCi/mL (5 nmol/L).

Preparation of Reduced Nicotinamide Adenine Dinucleotide Phosphate (NADPH)-Generating System To a mixture of 100 mM glucose 6-phosphate and 10-nmol/L NADPH solution, an equal volume of 100-nmol/L magnesium chloride was added. Glucose 6-phosphate dehydrogenase was employed at a final concentration of 10 unit/mL. These components were reconstituted upon use.

Method: To each of the glass test tubes, 0.167-nmol/L EDTA/ 0.33M potassium phosphate buffer (150 μL), Milli Q water (200 μL), 0.005 or 0.5 mg protein/mL microsome suspension (50 μL), and a test substance solution (50 μL) were added. The mixture was preliminarily incubated at 37° C. for two minutes. The above-prepared NADPH-generating system (50 μL) was added, to thereby initiate reaction. At an arbitrary point of time, an equal volume of acetonitrile was added, to thereby terminate the reaction. The reaction mixture (50 μL) was sampled into a glass tube for determining the metabolism amount, and saturated ascorbic acid ethanol solution (25 μL) was added thereto. The sample was developed by means of a reverse phase TLC (Whatman KC18F) with 80% methanol. The TLC was brought into contact with an imaging plate, and radioactivity was detected by means of BAS-1800 (product of Fuji Film Co., Ltd.). The metabolism rate was calculated through analysis by means of GraphPad Prism Ver. 4.00 (GraphPad Software, Inc.). The results are shown in Table 8.

These feature of the compounds were found to be not different between animal species. Compound 24 exhibited a very low metabolism rate and thus exhibited high stability to metabolism. Therefore, the metabolism thereof is conceivably less affected by the difference of animal species, and the pharmacokinetics is conceivably less affected by variation of metabolism-related enzymes depending on the age and the type of disease. In addition, high stability to metabolism attains minimization of the effect of a metabolism-related enzyme induced through administration of a therapeutic drug. The aforementioned advantages attain the object of the present invention, which realizes monitoring an Alzheimer's disease therapeutic agent.

TABLE 8

Rate of metabolism by liver microsomes

| | Compound 23 | Compound 24 | $^{125}$I-IMPY |
|---|---|---|---|
| Mouse | 0.480 ± 0.139 | 0.229 ± 0.061 | 0.911 ± 0.331 |
| Rat | 0.632 ± 0.420 | 0.193 ± 0.058 | 2.164 ± 0.647 |
| Human | 0.944 ± 0.265 | 0.140 ± 0.057 | 0.510 ± 0.137 | pmol/min/mg protein

The invention claimed is:

1. A compound represented by formula (I):

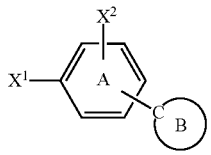

(1)

wherein
X¹ is an optionally substituted benzothiazolyl, benzoxazolyl, imidazopyridyl, imidazopyrimidyl, or benzimidazolyl group,
  wherein when X¹ is an imidazopyridyl the imidazopyridyl is substituted with one to three substituents and said substituent is selected from the group consisting of a halogen atom, a hydroxy group, an alkyl group, an alkyltin group, a halogenoalkyl group, a halogenoalkylcarbonylamino group, and a chelate-forming group,
X² represents a hydrogen atom, a halogen atom, or a chelate-forming group;
ring A represents a benzene ring or a pyridine ring; and
ring B represents an optionally substituted 5-membered aromatic heterocyclic group which is bonded to the benzene ring or the pyridine ring via a carbon atom of ring B,
wherein X¹ and ring B are in a para position, and
wherein X¹, X², or ring B has at least one radioactive nuclide, a salt thereof, or a transition metal coordination compound of any of these.

2. The compound, a salt thereof, or a transition metal coordination compound of any of these as described in claim 1, wherein X² is a halogen atom, X¹ is substituted with at least one halogen atom or halogen-containing group, and/or ring B is substituted with at least one halogen atom.

3. The compound, a salt thereof, or a transition metal coordination compound of any of these as described in claim 1, wherein X¹ has at least one radioactive nuclide.

4. The compound, a salt thereof, or a transition metal coordination compound of any of these as described in claim 1, wherein the radioactive nuclide is selected from a radioactive halogen atom and a radioactive transition metal atom.

5. The compound, a salt thereof, or a transition metal coordination compound of any of these as described in claim 1, wherein X¹ is substituted with one to three substituents and said substituent is selected from the group consisting of a halogen atom, a hydroxy group, an alkyl group, an alkyltin group, a halogenoalkyl group, a halogenoalkylcarbonylamino group, and a chelate-forming group.

6. The compound, a salt thereof, or a transition metal coordination compound of any of these as described in claim 1, wherein ring B is an optionally substituted 5-membered aromatic azo-heterocyclic group.

7. The compound, a salt thereof, or a transition metal coordination compound of any of these as described in claim 1, wherein ring B is an optionally substituted oxazolyl, isoxazolyl, thiazolyl, isothiazolyl, pyrazolyl, imidazolyl, triazolyl, thiadiazolyl, oxadiazolyl, or tetrazolyl group.

8. The compound, a salt thereof, or a transition metal coordination compound of any of these as described in claim 1, wherein the substituent of ring B is one to three substituents selected from among a halogen atom, an alkyl group, an alkoxy group, and a chelate-forming group.

9. A drug containing a compound, a salt thereof, or a transition metal coordination compound of any of these as recited in claim 1.

10. A pharmaceutical composition comprising a compound, a salt thereof, or a transition metal coordination compound of any of these as recited in claim 1, and a pharmaceutically acceptable carrier.

11. A method for imaging an amyloid deposit, wherein the method comprises administering, to a subject in need thereof, a labeled compound as recited in claim 1 in a detectable amount, allowing to pass a sufficient period of time for achieving binding between the labeled compound and the amyloid deposit, and detecting the labeled compound which has been bound to the amyloid deposit.

12. The compound, a salt thereof, or a transition metal coordination compound of any of these as described in claim 1, wherein X² has at least one radioactive nuclide.

13. The compound, a salt thereof, or a transition metal coordination compound of any of these as described in claim 1, wherein B has at least one radioactive nuclide.

14. [$^{123}$I]5-[4-(6-Iodoimidazo[1,2-a]pyridin-2-yl)phenyl]-1,3-oxazole.

15. [$^{123}$I]6-Iodo-2-[4-(1H-3-pyrazolyl)phenyl]imidazo[1,2-a]pyridine.

* * * * *